(12) United States Patent
Fujita et al.

(10) Patent No.: US 10,117,634 B2
(45) Date of Patent: Nov. 6, 2018

(54) ACOUSTIC AND VIBRATION INFORMATION ACCUMULATION MECHANISM, ACOUSTIC AND VIBRATION SENSING SYSTEM, AND COMPUTER PROGRAM

(71) Applicant: DELTA TOOLING CO., LTD., Hiroshima-shi (JP)

(72) Inventors: Etsunori Fujita, Higashihiroshima (JP); Shinichiro Maeda, Hatsukaichi (JP); Yumi Ogura, Higashihiroshima (JP); Kosuke Aoi, Hiroshima (JP); Ryuichi Uchikawa, Hiroshima (JP); Eiji Sugimoto, Higashihiroshima (JP); Kazuhiro Takenaka, Hiroshima (JP)

(73) Assignee: DELTA TOOLING CO., LTD., Hiroshima-shi (JP)

( * ) Notice: Subject to any disclaimer, the term of this patent is extended or adjusted under 35 U.S.C. 154(b) by 43 days.

(21) Appl. No.: 15/102,109

(22) PCT Filed: Jan. 6, 2015

(86) PCT No.: PCT/JP2015/050176
§ 371 (c)(1),
(2) Date: Jun. 6, 2016

(87) PCT Pub. No.: WO2015/083846
PCT Pub. Date: Jun. 11, 2015

(65) Prior Publication Data
US 2016/0367213 A1 Dec. 22, 2016

(30) Foreign Application Priority Data

Dec. 7, 2013 (JP) .................................. 2013-253715
Jul. 1, 2014 (JP) .................................. 2014-136353
Sep. 7, 2014 (JP) .................................. 2014-181814

(51) Int. Cl.
| | |
|---|---|
| A61B 7/02 | (2006.01) |
| A61B 5/00 | (2006.01) |
| A61B 5/02 | (2006.01) |
| G01H 1/00 | (2006.01) |
| A61B 5/024 | (2006.01) |

(52) U.S. Cl.
CPC .............. *A61B 7/02* (2013.01); *A61B 5/024* (2013.01); *A61B 5/02028* (2013.01);
(Continued)

(58) Field of Classification Search
CPC ......... A61B 7/02; A61B 5/024; A61B 5/6823; A61B 5/725
(Continued)

(56) References Cited

U.S. PATENT DOCUMENTS

| | | |
|---|---|---|
| 5,602,327 A | 2/1997 | Torizuka et al. |
| 2012/0101395 A1 | 4/2012 | Fujita et al. |
| 2013/0060164 A1 | 3/2013 | Fujita et al. |

FOREIGN PATENT DOCUMENTS

| | | |
|---|---|---|
| JP | 6-42373 U | 6/1994 |
| JP | 6-281530 A | 10/1994 |

(Continued)

OTHER PUBLICATIONS

International Search Report dated Mar. 31, 2015 in PCT/JP2015/050176 filed Jan. 6, 2015.
(Continued)

*Primary Examiner* — Carl H Layno
*Assistant Examiner* — Jon Eric C Morales
(74) *Attorney, Agent, or Firm* — Oblon, McClelland, Maier & Neustadt, L.L.P.

(57) ABSTRACT

There is provided a sound and vibration information collecting mechanism, which collects low-frequency sound and vibration information with a predetermined frequency or lower from a detection target, the mechanism including a resonance layer, which includes a natural oscillator having a
(Continued)

natural frequency within a frequency band of the sound and vibration information being a collection target, and generates a resonance carrier by the natural oscillator emphasizing the sound and vibration information; and a sensor, which detects the resonance carrier. The mechanism detects a bioacoustic signal and a biosignal more accurately than conventionally.

17 Claims, 42 Drawing Sheets

(52) U.S. Cl.
CPC .......... *A61B 5/4035* (2013.01); *A61B 5/6804* (2013.01); *A61B 5/6823* (2013.01); *A61B 5/6891* (2013.01); *A61B 5/725* (2013.01); *G01H 1/00* (2013.01)

(58) Field of Classification Search
USPC ........................................................ 600/586
See application file for complete search history.

(56) References Cited

FOREIGN PATENT DOCUMENTS

| JP | 2011-152242 A | 8/2011 |
|----|----|----|
| WO | 2010/123125 A1 | 10/2010 |
| WO | WO 2011/007886 A | 1/2011 |

OTHER PUBLICATIONS

Written Opinion of the International Search Authority dated Mar. 31, 2015 in international application No. PCT/JP2015/050176 (5 pages).

Fig. 5
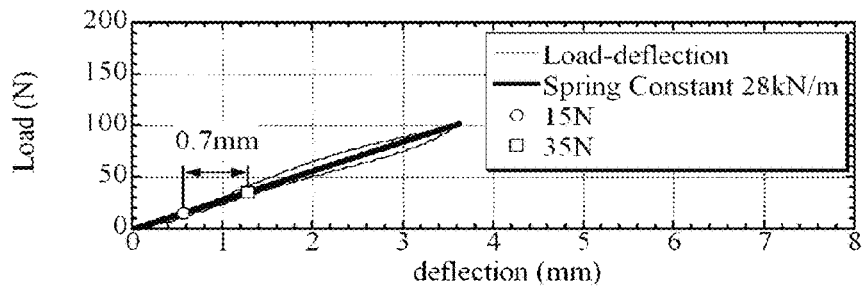
(a) 3D net of 10mm thickness (First and second layer)
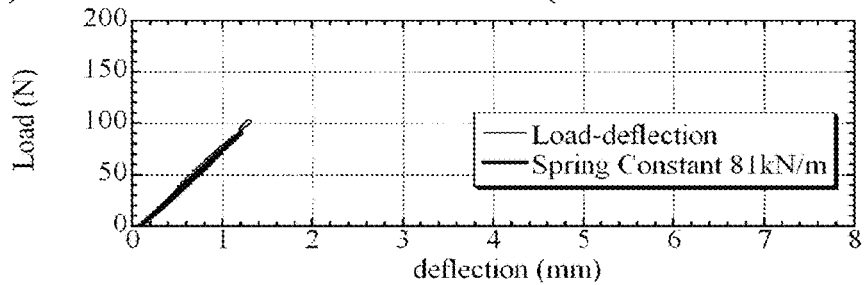
(b) 3D net of 7mm thickness (Third layer)
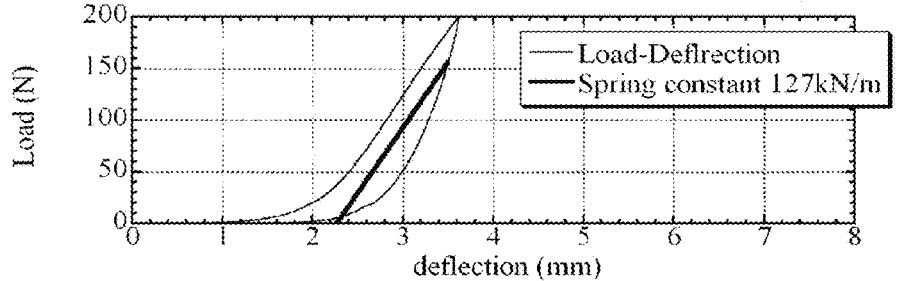
(c) Load-deflection characteristics of foamed beads
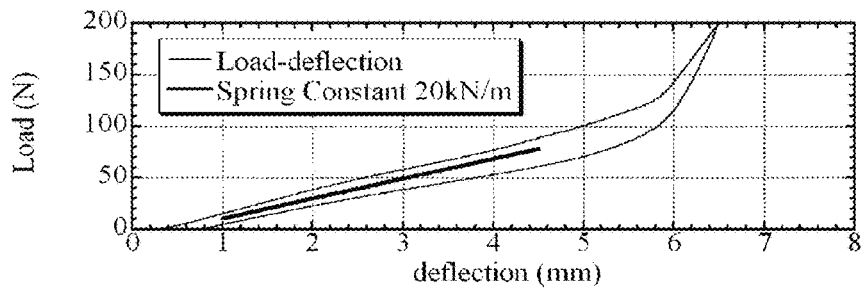
(d) 3S.R.

Fig. 6
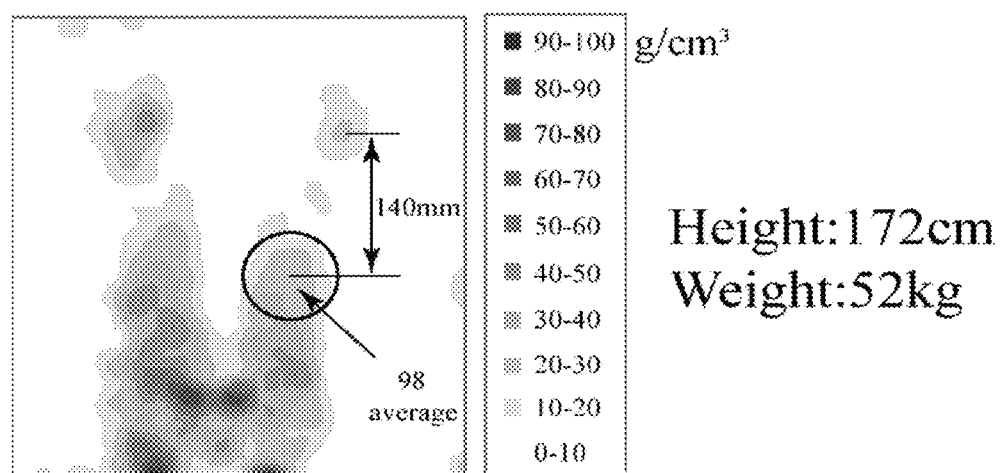
(a) Sitting position
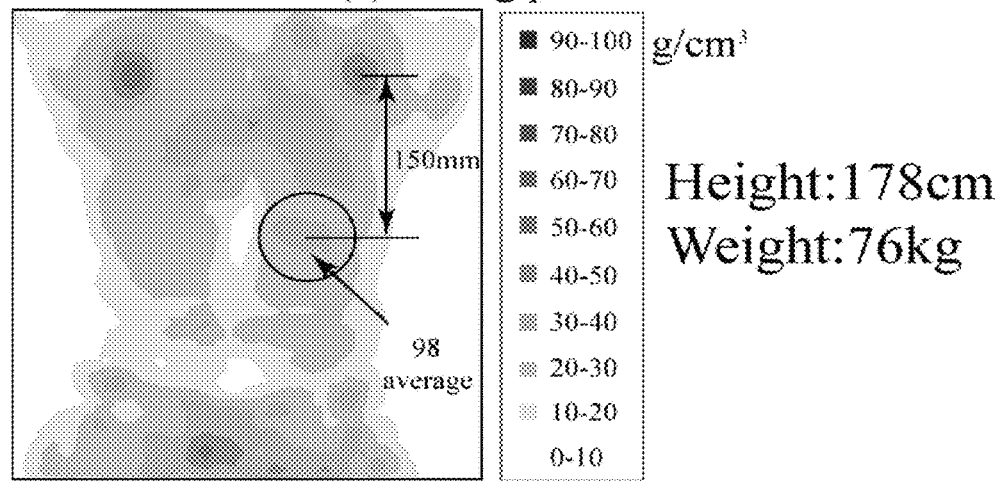
(b) Supine position

Fig. 9
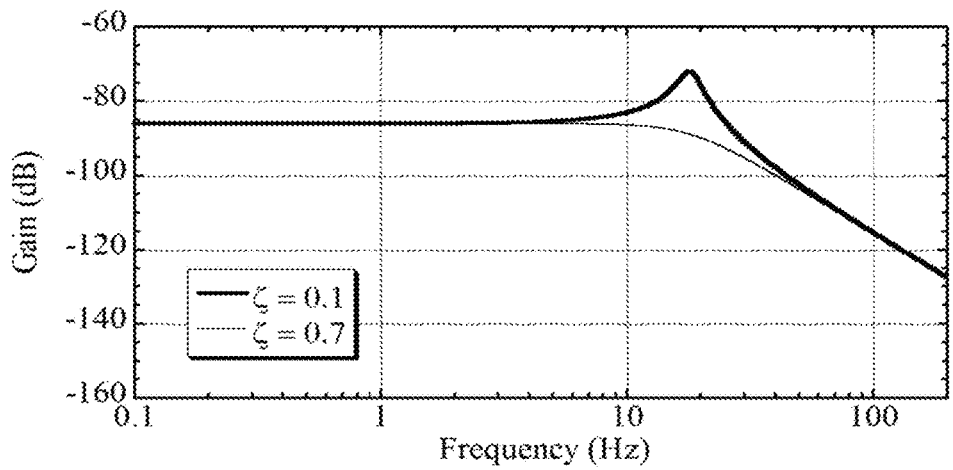
(a) Gain (3DNO)
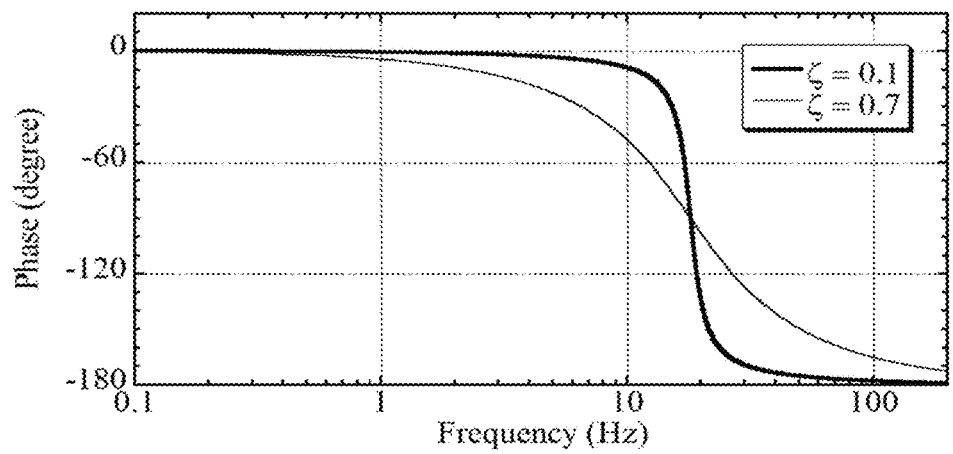
(b) Phase (3DNO)
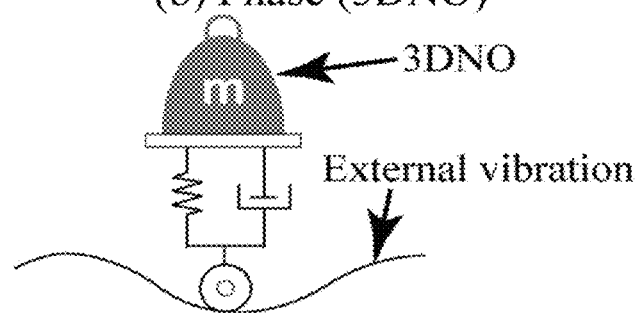
(c) Vibration model of 3DNO Fig. 11
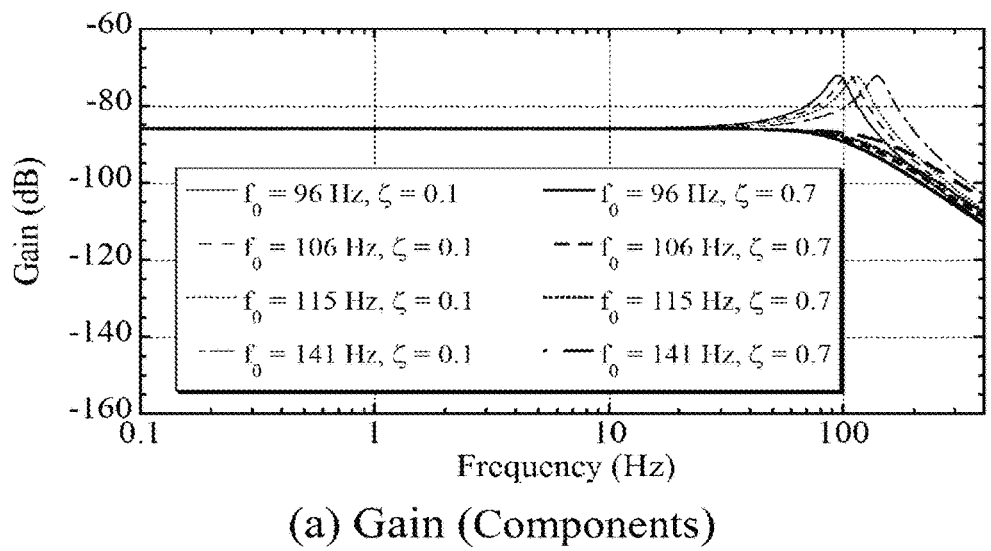
(a) Gain (Components)
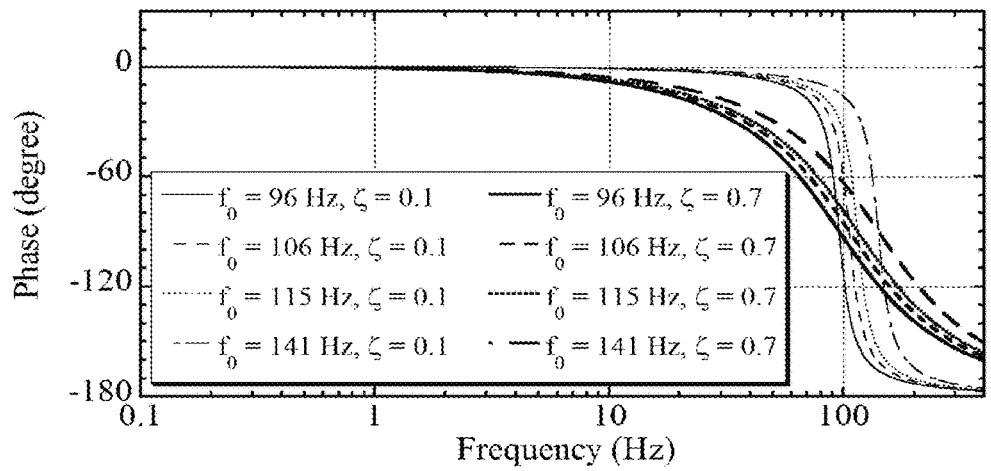
(b) Phase (Components)

Fig. 14
(a)
● 1/3 OCTAVE BAND FILTER
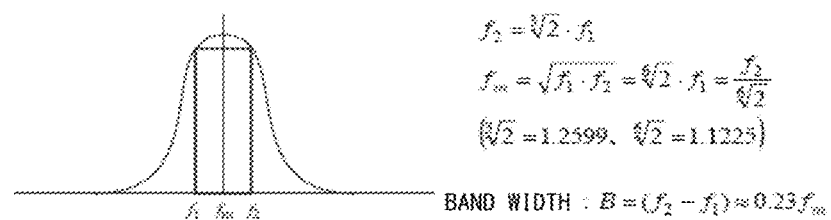
BAND WIDTH : $B = (f_2 - f_1) \approx 0.23 f_m$
(b)
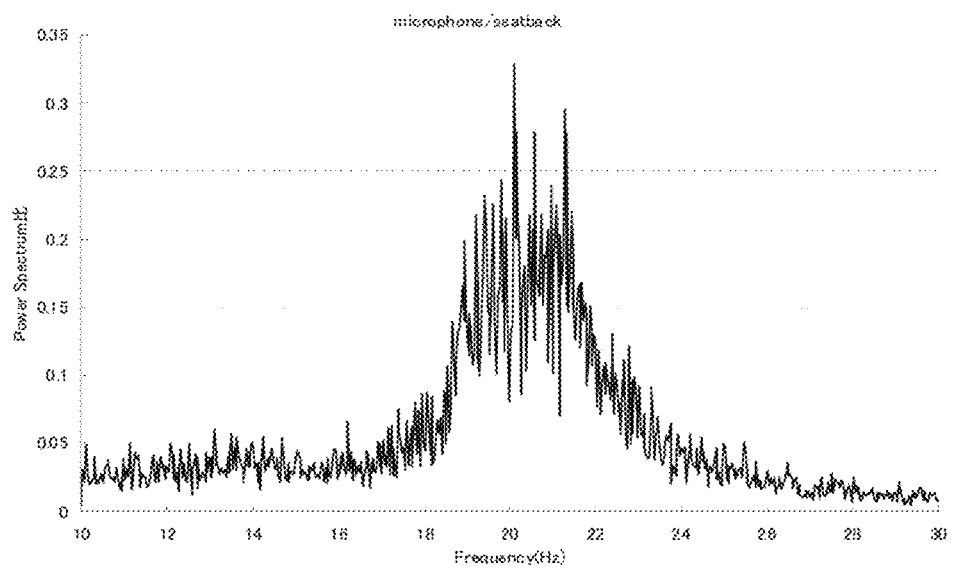

(a) Static (b) Dynamic (Power Spectrum max range 0.015)

(c) Dynamic (Power Spectrum max range 0.003)

(d) PCG (Static and Dynamic)

(a) Static (b) Dynamic

Fig. 23
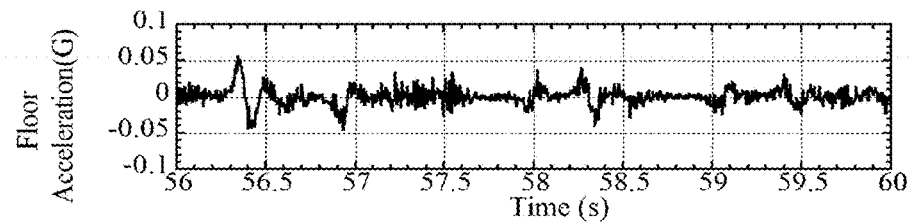
(a) Time series waveform of input acceleration
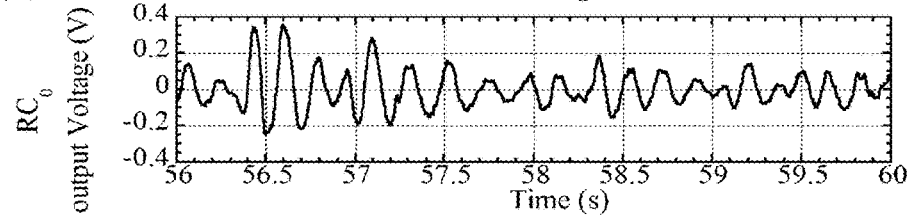
(b) Time series waveform of $RC_0$
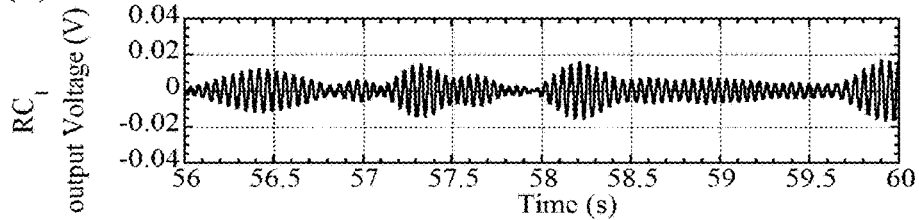
(c) Time series waveform of $RC_2$
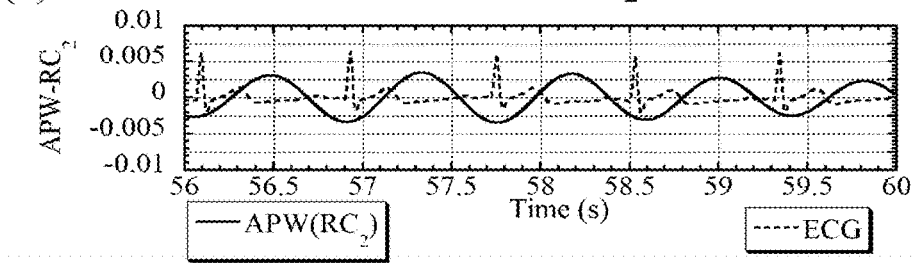
(d) Time series waveform of ECG and APW (a) The phase lag of RRI and APW Interval (b) Comparison of RRI and APW interval Fig. 30
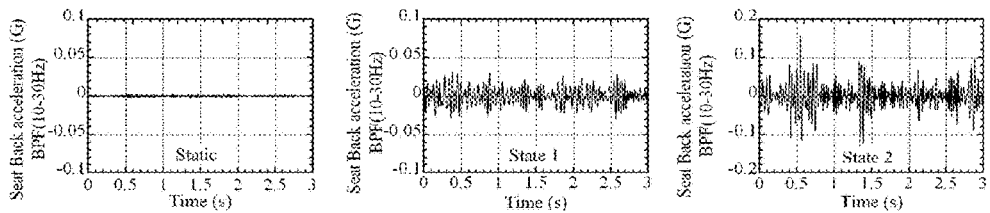
(a) Seat back acceleration
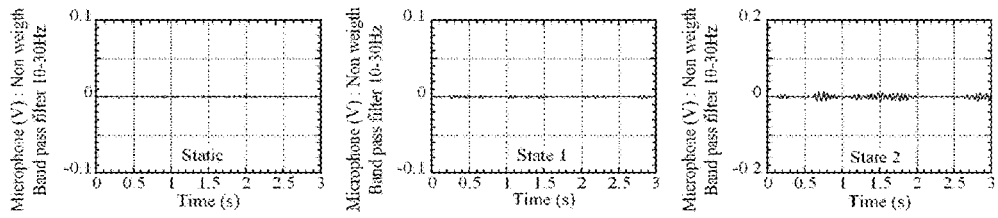
(b) Microphone from seat back acceleration
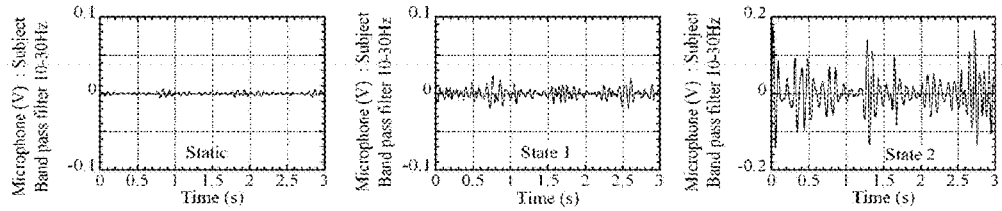
(c) Microphone with Subject
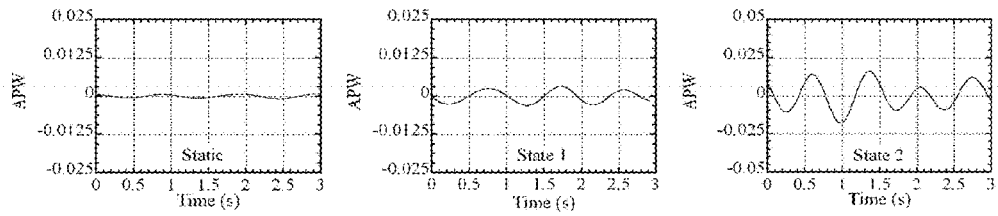
(d) APW

ACOUSTIC AND VIBRATION INFORMATION ACCUMULATION MECHANISM, ACOUSTIC AND VIBRATION SENSING SYSTEM, AND COMPUTER PROGRAM

TECHNICAL FIELD

The present invention relates to a sound and vibration information collecting mechanism, a sound and vibration information sensing system using the sound and vibration information collecting mechanism, and a computer program.

BACKGROUND ART

The present applicant discloses, in Patent Documents 1, 2, and so on, a means which captures a vibration waveform with around 1 Hz reflecting an autonomic nervous function (hereinafter, referred to as an aortic pulse wave (APW)), based on vibration generated on the body surface of the back, finds a frequency time series waveform from a time series waveform of the vibration, and further finds a time series waveform of frequency gradient and a time series waveform of frequency fluctuation, and analyzes their frequencies to determine a state of the person. This means is capable of detecting the aortic pulse wave (APW) in an unconstrained state, and thus, when applied to a vehicle seat, it is excellent as a means for obtaining bio-information of the driver while he/she is driving, and is capable of detecting a hypnagogic symptom phenomenon, an imminent sleep phenomenon, and so on of the driver.

Since the aforesaid APW, heartbeat, or the like is a biosignal reflecting the autonomic nervous function, analyzing this enables the determination of the state of the person as described above, but these biosignals reflecting the autonomic nervous function have very low frequencies of several Hz or lower, for example, belonging to a range from the ULF band (ultra low frequency band) to the VLF band (very low frequency band), and are likely to be buried in external vibration inputted from the floor of the vehicle. So, in extracting the biosignal, an influence of the external vibration has to be eliminated by, for example, the use of the aforesaid time series waveform of frequency gradient. Even if the biosignal can be extracted using the time series waveform of frequency gradient and the like, output signal data detected from a sensor is desirably more suitable for extracting the biosignal.

In consideration of the above, the present applicant proposes, in Patent Document 3, an apparatus which amplifies a biosignal by using string vibration of a three-dimensional knitted fabric disposed as a biosignal detection sensor and disposed in a hole portion formed in a bead foam and also by co-using membrane vibration of a bead foam stacked on one surface or both surfaces of the three-dimensional knitted fabric, to thereby detect the biosignal by a vibration sensor with as high sensitivity as possible.

PRIOR ART DOCUMENT

Patent Document

Patent Document 1: WO2010/123125
Patent Document 2: WO2011/007886
Patent Document 3: Japanese Patent Application Laid-open No. 2011-152242

SUMMARY OF THE INVENTION

Problems to be Solved by the Invention

In the detection of biosignals, however, higher-sensitivity detection is always desired for the purpose of more accurate determination of the state of a person.

Meanwhile, diagnosis with a stethoscope based on heart sound and cardiac murmur by distinguishing low-frequency sound, high-frequency sound, and noise has been developed as "present condition observation technology" performed by doctors. Further, the recent development of various kinds of high-technology devices has promoted detailed scientific inspection of an abnormal morbid condition and aging of the cardio-vascular system. In any case, however, these diagnosis and inspection should be carried out under instructions of doctors at hospitals, and require that even a healthy person should go to the hospital, and thus take a lot of trouble. For this reason, what are in widespread as easy-to-use tools for everyday health management are mainly weighing scales, body fat rate scales, and sphygmomanometers, but means for finding sound and vibration information of the cardio-vascular system (in this specification, information including biosound and vibration not reaching the audible spectrum which are generated due to the motion of the cardio-vascular system is referred to as "sound and vibration information") without depending on medical examination at hospitals have not been in widespread. Though heart rate meters and the like which are worn on an arm, a hand, or a finger for use are available on the market, to wear them itself is sometimes difficult due to the age, physical and mental conditions, and so on of a user.

Further, in, for example, a diesel engine of an automobile, sound and vibration information with a predetermined frequency or lower, for example, in a frequency band of several hundred Hz or lower, in particular 200 Hz or lower, and further 100 Hz or lower is generated. So, accurate detection of such sound and vibration information in such a low-frequency range, if possible, helps determine a trouble of the engine. The same thing can be said also for other machines and devices, not only for the diesel engine.

The present invention was made in consideration of the above and has an object to provide a sound and vibration information collecting mechanism capable of highly sensitively extracting a biosignal, in particular, sound and vibration information of the cardio-vascular system from the trunk in an unconstrained state, a sound and vibration information sensing system including the sound and vibration information collecting mechanism and capable of analyzing the biosignal with higher accuracy, and a computer program therefor. Another object is to provide a technique applicable also to the collection of low-frequency sound and vibration information other than the biosignal by utilizing the fact that the low-frequency sound and vibration information such as the biosignal can be extracted with high sensitivity.

Means for Solving the Problems

The present inventor repeated studious studies in order to solve the aforesaid problems and focused on using a natural oscillator to emphasize sound and vibration information of the cardio-vascular system which information is a biosignal with 100 Hz or lower (heart sound has mainly 25 to 50 Hz (first sound: 25 to 45 Hz, second sound: near 50 Hz)), though a conventional importance was put on eliminating an influence of external vibration as much as possible and amplifying only a biosignal. The present inventor also focused on more increasing an amplitude of a detected output waveform by taking external vibration capable of emphasizing the biosignal, and finally accomplished the present invention. The present inventor also thought that the technology to emphasize the low-frequency sound and vibration information such as the biosignal is applicable also to detection of small sound and vibration information in various kinds of detection targets.

That is, the present invention provides a sound and vibration information collecting mechanism which collects low-frequency sound and vibration information with a predetermined frequency or lower from a detection target, the mechanism including: a resonance layer which includes a natural oscillator having a natural frequency within a frequency band of the sound and vibration information being a collection target, and generates a resonance carrier by the natural oscillator emphasizing the sound and vibration information; and a sensor which detects the resonance carrier.

Preferably, the sound and vibration information collecting mechanism includes: a first layer which is disposed on the detection target side and to which the sound and vibration information propagates; and a second layer which includes: a casing for resonance having an arrangement space formed as a hole portion or a groove portion where to arrange the natural oscillator and the sensor; and a film covering the arrangement space, and which functions as the resonance layer.

Preferably, the detection target is a living body, and the sound and vibration information is a biosignal.

Preferably, the biosignal is sound and vibration information of a cardio-vascular system, and the natural frequency of the natural oscillator is within a frequency band including a frequency of first heart sound or second heart sound included in the sound and vibration information of the cardio-vascular system.

Preferably, the sound and vibration information collecting mechanism is disposed on a back side of a trunk of the living body and detects the first heart sound or the second heart sound included in the sound and vibration information of the cardio-vascular system, as sound and vibration information attenuated to a 10 to 40 Hz frequency band.

Preferably, the natural frequency of the natural oscillator is 20 to 30 Hz.

Preferably, the sound and vibration information collecting mechanism includes: a first layer which is disposed on the back side of the trunk of the living body and to which the sound and vibration information of the cardio-vascular system propagates; and a second layer which includes: a casing for resonance having an arrangement space formed as a hole portion or a groove portion where to arrange the natural oscillator and the sensor; and a film covering the arrangement space, and which functions as the resonance layer, and the second layer side is supported by a support layer which is provided in a body support means to damp externally inputted sound and vibration.

Preferably, the sound and vibration information collecting mechanism further includes a third layer which is disposed opposite to the first layer across the second layer to damp the externally inputted sound and vibration and is provided integrally.

Preferably, the third layer has a property of damping sound and vibration with a frequency not corresponding to the natural frequency of the natural oscillator.

Preferably, the casing for resonance of the second layer is formed of a bead foam.

Preferably, the natural oscillator of the second layer and the first layer are each formed of a three-dimensional fabric.

Preferably, the third layer is formed of a three-dimensional fabric.

Preferably, the three-dimensional fabric is a three-dimensional knitted fabric.

Preferably, a spring constant of the first layer and a spring constant of the natural oscillator of the second layer approximate a spring constant of muscle of a human body.

Preferably, a spring constant of the first layer and a spring constant of the natural oscillator of the second layer approximate a spring constant of muscle of a human body, and a spring constant of the third layer is higher than the spring constants of the first layer and the natural oscillator of the second layer.

Preferably, a cutoff frequency as a mechanical filter, of the second layer is set twice as high as a frequency of the biosignal being the collection target or higher.

Preferably, the sound and vibration information collecting mechanism is attached to the body support means which supports the trunk of a person, when in use.

The present invention further provides a sound and vibration information sensing system which collects and analyzes low-frequency sound and vibration information with a predetermined frequency or lower from a detection target, the system including: any one of the above-described sound and vibration information collecting mechanisms; and an arithmetic means which receives a resonance carrier generated in the resonance layer of the sound and vibration information collecting mechanism, via the sensor provided in the sound and vibration information collecting mechanism and includes a filtering means which filters the received resonance carrier, with a predetermined filtering frequency.

Preferably, a cutoff frequency of the filtering means set in the arithmetic means is set within a pass band width including the natural frequency of the natural oscillator in the sound and vibration information collecting mechanism.

Preferably, the filtering means is a band pass filter with a predetermined pass band width, and when the detection target by the sound and vibration information collecting mechanism is the living body and the sound and vibration information being the collection target is the sound and vibration information of the cardio-vascular system, a center frequency of the pass band width is set within a 20 to 30 Hz range.

Preferably, the arithmetic means includes a state analyzing means which analyzes a state of the detection target by using a signal waveform of a resonance carrier generated as a result of the filtering of the resonance carrier by the filtering means.

Preferably, when the detection target by the sound and vibration information collecting mechanism is the living body and the sound and vibration information being the collection target is the sound and vibration information of the cardio-vascular system, the state analyzing means includes a means which rectifies, by detection, a signal waveform of the resonance carrier generated as a result of the filtering by the filtering means, and finds a low-frequency biosignal with 5 Hz or lower which reflects an autonomic nervous function.

Preferably, the state analyzing means further includes a means which, after the low-frequency biosignal with 5 Hz or lower is found, filters a time series waveform of the biosignal by a band pass filter whose pass band width is 0.1 to 1 Hz.

Preferably, the sound and vibration information sensing system further includes an audible sound reproduction part which reproduces, as audible sound, the resonance carrier generated in the resonance layer of the sound and vibration information collecting mechanism or the resonance carrier generated as a result of the filtering by the filtering means. In this case, preferably, a predetermined amplitude threshold is set in the resonance carrier, shaping processing to cut a waveform component at or exceeding the threshold is applied to the resonance carrier, a waveform generated as a result of the shaping processing is filtered by a high pass filter, and the audible sound reproduction part uses a waveform generated as a result of the filtering by the high pass filter, for the reproduction.

The present invention further provides a computer program causing a computer in a sound and vibration information sensing system which collects and analyzes the biosignal from the trunk, to execute a procedure, the computer receiving the resonance carrier generated in the resonance layer of any one of the sound and vibration information collecting mechanisms, via the sensor provided in the sound and vibration information collecting mechanism, and the procedure being a filtering procedure to filter the received resonance carrier, with a predetermined filtering frequency.

Preferably, in the filtering procedure, the computer is caused to execute a procedure to perform the filtering so that a pass band width includes the natural frequency of the natural oscillator of the sound and vibration information collecting mechanism.

Preferably, the computer is caused to further execute a state analyzing procedure to analyze a state of the detection target by using a signal waveform of a resonance carrier generated as a result of the filtering of the resonance carrier by the execution of the filtering procedure.

Preferably, when the detection target by the sound and vibration information collecting mechanism is the living body and the sound and vibration information being the collection target is the sound and vibration information of the cardio-vascular system, in the state analyzing procedure, the computer is caused to execute a procedure to rectify, by detection, a signal waveform of the resonance carrier generated as a result of the filtering by the filtering procedure, and find a low-frequency biosignal with 5 Hz or lower which reflects an autonomic nervous function.

Preferably, in the state analyzing procedure, the computer is caused to further execute a procedure to, after the low-frequency biosignal with 5 Hz or lower is found, filter a time series waveform of the biosignal by a band pass filter whose pass band width is 0.1 to 1 Hz.

Effect of the Invention

According to the present invention, the resonance layer forming the sound and vibration information collecting mechanism has the natural oscillator. The natural frequency of the natural oscillator is set within the frequency band of the sound and vibration information of the detection target. When the detection target is a living body, this natural frequency is set within the frequency band of the biosignal collected from, for example, the trunk. Accordingly, when the sound and vibration information of the detection target is inputted, or if the detection target is a living body, when the biosignal, in particular the sound and vibration information of the cardio-vascular system, is inputted, the inputted sound and vibration information is combined with a vibration waveform of the natural oscillator due to a resonance phenomenon and a beat phenomenon, and consequently, the emphasized resonance carrier is outputted. The detection of the emphasized resonance carrier allows the sensor to detect the low-frequency sound and vibration information being an analysis target, typically the biosignal, with higher sensitivity than conventionally. Further, under a dynamic environment in which external vibration is inputted, external vibration in a predetermined frequency band corresponding to the natural frequency of the natural oscillator is taken and thus the natural oscillator is vibrated by the external input, so that a composite wave (resonance carrier) of the vibration waveform of the natural oscillator and the low-frequency sound and vibration information such as the biosignal of the detection target comes to have a larger amplitude due to the resonance phenomenon and the beat phenomenon, making it possible to more distinctly detect the low-frequency sound and vibration information of the detection target, such as the biosignal from the trunk, in particular, the sound and vibration information of the cardio-vascular system. As a result, it is possible to more accurately find the biosignal with several Hz or lower, such as APW and heartbeat, reflecting the autonomic nervous function, which biosignal is found after the resonance carrier is filtered with a predetermined filtering frequency and then the resultant is subjected to a predetermined analysis.

In addition, the sound and vibration information collecting mechanism of the present invention is capable of detecting the sound and vibration information in an unconstrained state, that is, it only needs to be disposed so as to come into contact with the detection target, or if the detection target is the biosignal, it only needs to be disposed so as to come into contact with the back of the trunk of the person. Thus, in order to enable the detection of the sound and vibration information of the cardio-vascular system, it is only necessary that the sound and vibration information collecting mechanism is attached to a body support means such as a bed or a chair (including chairs for furniture and office and a seat of a vehicle such as an automobile), specifically, to a trunk corresponding part of the bed, a seat back rest of the chair, or the like and the person lies or sits on the bed or the chair.

It is of course possible that the sound and vibration information collecting mechanism and the arithmetic means constituted by the computer to analyze the sound and vibration information collecting mechanism, which are included in the sound and vibration information sensing system, are set at a physically short distance from each other and the arithmetic means directly analyzes the sound and vibration information of the detection target, such as the biosignal, at a site where the sound and vibration information is measured, but the both, even if set distant from each other, may be connected via a wired or wireless communication means (including the communication through a mobile wireless terminal such as a mobile phone, a smartphone, a wearable terminal, and so on) to exchange data with each other. This enables to obtain, from a remote place, the sound and vibration information of the cardio-vascular system of for example, a bedridden elderly person or a patient having a difficulty in going out, contributing to distance medicine. Further, by attaching the sound and vibration information collecting mechanism to a driver's seat of a vehicle such as an automobile, it is possible to easily obtain the sound and vibration information of the cardio-vascular system during driving. In this case as well, adoptable is a structure in which the arithmetic means is set in the vehicle and the analysis result is displayed on a display (not only a specialized display but also a display of a navigation system or a display of a mobile wireless terminal such as a mobile phone, a smartphone, or a wearable terminal held by an occupant) in the vehicle so as to enable a driver to see the analysis result in the vehicle. Alternatively or in combination with the above structure, the sound and vibration information collecting mechanism and the arithmetic means may be connected via a wired or wireless communication means (including the communication through a mobile wireless terminal such as a mobile phone, a smartphone, and a wearable terminal) to enable a manager of a driving state to see and analyze the sound and vibration information of the cardio-vascular system of the driver in real time. Further, in such cases where the detection target is an engine or other machine or device of an automobile, a real-time analysis of troubles and the like of these during driving or activation is possible.

BRIEF DESCRIPTION OF DRAWINGS

FIG. 5(a) is a chart illustrating a load-deflection characteristic of a three-dimensional knitted fabric of a first layer and a three-dimensional knitted fabric forming a natural oscillator of a second layer, (b) is a chart illustrating a load-deflection characteristic of a three-dimensional knitted fabric of a third layer, (c) is a chart illustrating a load-deflection characteristic of a bead foam, and (d) is a chart illustrating a load-deflection characteristic of the sound and vibration information collecting mechanism (3S.R.).

FIG. 6(a) is a chart illustrating an example of body pressure distribution of a sitting position and (b) is a chart illustrating an example of body pressure distribution of a supine position.

FIGS. 9(a), (b) illustrate Bode plots used to find a frequency response of the three-dimensional knitted fabric (3DNO) forming the natural oscillator, and (c) is a view illustrating a vibration model of the three-dimensional knitted fabric (3DNO) forming the natural oscillator.

FIGS. 11(a), (b) illustrate Bode plots of components forming the sound and vibration information collecting mechanism.

FIG. 14 are explanatory charts of a ⅓ octave band filter, (a) being a chart illustrating calculation equations for finding a center frequency, upper and lower limit frequencies, and a band width, and (b) being a chart illustrating a frequency characteristic of the ⅓ octave band filter used in the embodiment.

FIGS. 23(a) to (d) are charts illustrating processes where the natural oscillator functions in response to an external vibration input to generate a composite wave.

FIGS. 30(a) to (d) are charts illustrating experiment results used for more detailed explanation of a relation between external vibration and the resonance carrier under the static environment and two dynamic environments.

MODES FOR CARRYING OUT THE INVENTION

Figure 1:
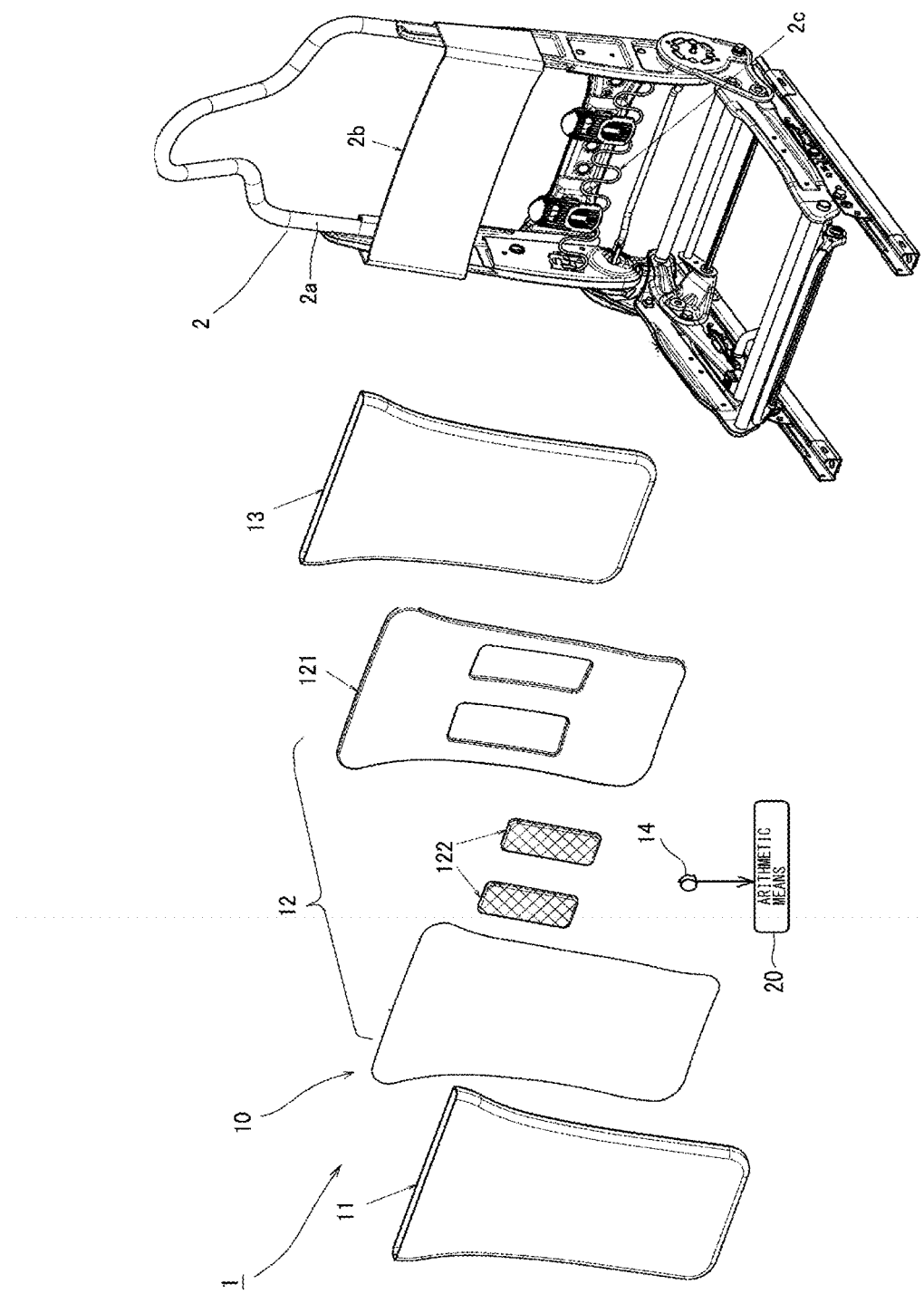
FIG. 1 is an explanatory view of the structure of a sound and vibration information sensing system according to one embodiment of the present invention.

The present invention will be hereinafter described in more detail based on embodiments of the present invention illustrated in the drawings. FIG. 1 is a view illustrating the structure of a sound and vibration information sensing system 1 according to this embodiment. FIG. 1 illustrates an image where a sound and vibration information collecting mechanism 10 is installed on a seat back part of an automobile seat 2 and this is analyzed by an arithmetic means 20. That is, this embodiment is an example where a detection target is a living body (person) and a biosignal is detected from his/her trunk.

The sound and vibration information collecting mechanism 10 has a three-layer structure in which a first layer 11, a second layer 12, and a third layer 13 are stacked in order from the top layer side as illustrated in FIGS. 2(a), (b), and is used with the first layer 11 being located on a person's body side from which the biosignal is to be detected. Accordingly, the biosignal from the trunk of the person, in particular, sound and vibration information of the cardio-vascular system, including biosound (trunk direct sound or a bioacoustic signal) generated in accordance with the vibration of the ventricles, the atria, or the great vessels propagates first to the first layer 11 which is a biosignal input system.

The first layer 11, which is a bioacoustic signal propagation layer, plays a role of widening a contact area with the human body and is formed of a three-dimensional fabric having a predetermined area. The three-dimensional fabric can be formed of a woven fabric, a knitted fabric, or the like, but is preferably formed of a three-dimensional knitted fabric. The three-dimensional knitted fabric is composed of a pair of ground knitted fabrics which are disposed apart from each other and coupled to each other with a connecting yarn. The ground knitted fabrics each can be formed to have a flat knitted fabric structure (fine mesh) continuous both in a course direction and a wale direction, or a knitted fabric structure having honeycomb-shaped (hexagonal) meshes, by using yarns of twisted fibers, for instance. The connecting yarn imparts predetermined rigidity to the three-dimensional knitted fabric so that one of the ground knitted fabrics and the other ground knitted fabric are kept apart from each other by a predetermined distance. Accordingly, applying tension in a surface direction makes it possible to cause string vibration of the yarns of the facing ground knitted fabrics constituting the three-dimensional knitted fabric or the connecting yarn connecting the facing ground knitted fabrics.

Accordingly, the string vibration is generated due to sound and vibration of the cardio-vascular system, which is the biosignal, and propagates in the surface direction of the three-dimensional knitted fabric. At this time, the three-dimensional knitted fabric forming the first layer 11 is given a load of the person to be given the tension, so that its connecting yarn becomes easily vibratable. The first layer 11, which is intended to increase the contact area with the trunk, preferably has such a size that its width is about equal to the width of the trunk of the person or narrower than this by several cm at each of the left and right sides, and its length covers an area corresponding to the chest position up the vicinity of the lumbar part. For example, it can have a size of a 300 to 350 mm width and a 400 to 550 mm length.

As a material of the yarns forming the ground knitted fabrics or the connecting yarn of the three-dimensional knitted fabric, those of various kinds are usable, and examples thereof include synthetic fibers and regenerated fibers such as polypropylene, polyester, polyamide, polyacrylonitrile, and rayon, and natural fibers such as wool, silk, and cotton. The above materials each may be used independently, or an arbitrary combination of these is also usable. The material is preferably a thermoplastic polyester-based fiber represented by polyethylene terephthalate (PET), polybutylene terephthalate (PBT), or the like, a polyamide-based fiber represented by nylon 6, nylon 66, or the like, a polyolefin-based fiber represented by polyethylene, polypropylene, or the like, or a combination of two kinds of these fibers or more. Further, the shape of the ground yarns or the connecting yarn is not limited either, and they each may be any of a round cross-section yarn, a modified cross-section yarn, a hollow yarn, and so on. Further, a carbon yarn, a metallic yarn, or the like is also usable.

A property of the three-dimensional knitted fabric forming the first layer 11 to propagate the sound and vibration of the cardio-vascular system utilizing the aforesaid string vibration can be variously adjusted by the thickness of the three-dimensional knitted fabric, the knitted fabric structure of the ground knitted fabrics, a way the connecting yarn is knitted to the ground knitted fabrics, the thickness and materials of the yarns forming the ground knitted fabrics and the connecting yarn, and so on.

The following three-dimensional knitted fabrics are usable, for instance.

(a) product number: 49013D (manufactured by Suminoe Textile Co., Ltd.), 10 mm thickness
material:
front-side ground knitted fabric . . . twisted yarn of two polyethylene terephthalate fiber false twisted yarns with 450 decitexes/108 f
rear-side ground knitted fabric . . . twisted yarn of two polyethylene terephthalate fiber false twisted yarns with 450 decitexes/108 f
connecting yarn . . . polytrimethylene terephthalate monofilament with 350 decitexes/1 f (b) product number: AKE70042 (manufactured by Asahi Kasei Corporation), 7 mm thickness (c) product number: T28019C8G (manufactured by Asahi Kasei Corporation), 7 mm thickness The second layer 12 functions as a resonance layer which emphasizes the biosignal, in particular, the sound and vibration of the cardio-vascular system, propagated from the first layer 11, by a resonance phenomenon or a beat phenomenon. The second layer 12 includes a casing 121 as a resonance box, natural oscillators 122, and films 123. The casing 121 is preferably formed of a bead foam. As the bead foam, usable is a foam molded body formed by a bead method of resin including at least one of polystyrene, polypropylene, and polyethylene, for instance. The casing 121 formed of the bead foam propagates sound and vibration having a small amplitude as membrane vibration owing to properties of spherical resin films forming individual small beads and formed as a result of foaming.

In a case where the casing 121 is formed of the bead foam, it is preferable that its expansion ratio is within a range of 20 to 50 times and the casing 121 is formed with a thickness equal to or lower than an average diameter of the beads. For example, in a case where the average diameter of the beads whose expansion ratio is 30 times is about 4 to 6 mm, the casing 121 is slice-cut to an about 3 to 5 mm thickness. Consequently, the casing 121 is given soft elasticity and thus easily generates solid vibration resonant with small-amplitude vibration.

The natural oscillators (harmonic oscillators) 122 are each formed of a three-dimensional fabric, preferably, a three-dimensional knitted fabric. The same three-dimensional knitted fabric as that forming the aforesaid first layer 11 is usable. For example, a strip-shaped one whose width is within a 40 to 100 mm range and whose length is within a 100 to 300 mm range is used. The three-dimensional knitted fabrics forming the natural oscillators 122 are each preferably worked by vibration welding or the like so that an end portion thereof becomes thin. Consequently, tension acts in the surface direction to facilitate the generation of string vibration. In the three-dimensional knitted fabric forming the aforesaid first layer 11 as well, it is preferable that its end portion is similarly worked in this manner. In this embodiment, two pieces of the natural oscillators 122 are disposed symmetrically with respect to a portion corresponding to the backbone to reduce an uncomfortable feeling when the back comes into contact therewith. The casing 121 formed of the bead foam is formed in a substantially rectangular shape with a predetermined area and has two arrangement spaces which are formed as vertically long hole portions or grooves, in this embodiment two arrangement through holes 121a, 121a, at the symmetric positions with respect to the portion corresponding to the backbone, and the two natural oscillators 122, 122 are inserted and arranged in the arrangement through holes 121a, 121a.

On front and rear sides of the natural oscillators 122, 122, the films 123, 123 are stacked. That is, the films 123, 123 are stacked, with their peripheral edge portions pasted on peripheral edge portions of the arrangement through holes 121a, 121a. As a result, the natural oscillators 122, 122 formed of the three-dimensional knitted fabrics are housed in inner parts surrounded by the arrangement through holes 121a, 121a of the casing 121 and the films 123, 123, and they function as the resonance layers. Incidentally, instead of the films 123, 123 disposed for the respective natural oscillators 122, 122, a film large enough to cover both of the two natural oscillators 122, 122 may be used. Further, as the films 123, 123, plastic films made of polyurethane elastomer (for example, product number "DUS605-CDR" manufactured by Sheedom Co., Ltd.) is usable, for instance.

Further, as the natural oscillators 122, 122, those thicker than the casing 121 are preferably used. Consequently, when the peripheral edge portions of the films 123, 123 are pasted on the peripheral edge portions of the arrangement through holes 121a, 121a, the natural oscillators 122, 122 are pressed in the thickness direction, so that tension is generated in the films 123, 123 due to reactive forces to easily cause membrane vibration of the films 123, 123. At the same time, pre-compression also occurs in the natural oscillators 122, 122 and tension due to the reactive forces is generated also in the connecting yarns retaining the thickness and shape of the three-dimensional knitted fabrics, so that the string vibration is easily generated.

Here, the natural frequency of each of the natural oscillators 122, 122 is set so as to be within a frequency band including a frequency of the biosignal which is a collection target from the trunk, in this embodiment, the sound and vibration information of the cardio-vascular system. Specifically, the biosignal collected from the trunk is in a frequency band of 100 Hz or lower and thus the natural oscillators 122, 122 are each structured so as to have a natural frequency of 100 Hz or lower. Heart sound included in the sound and vibration information of the cardio-vascular system out of the biosignals has 25 to 50 Hz (first sound: 25 to 45 Hz, second sound: around 50 Hz), but as is apparent from later-described test examples, in the case where the sound and vibration information is collected from the back of the trunk, the sound and vibration information is attenuated by bones, muscle, skin, and so on, and comes to have a signal waveform in a frequency band of 10 to 40 Hz, in particular, around 20 Hz. Accordingly, the natural frequency of each of the natural oscillators 122, 122 is preferably set within a range of 20 to 30 Hz, and more preferably set to especially around 20 Hz. Further, in recent automobiles, due to improvement of suspension, body rigidity, seat rigidity, and so on of vehicles, high-frequency vibration with 10 Hz or higher inputted from the vehicle body to a person on the seat to cause visceral resonance is generated in a band of 40 Hz or higher. Vibration in a 20 to 30 Hz frequency band is also more suppressed than in conventional vehicles and these vibrations are also prevented from being inputted as noise that is so big as to make the biosignal buried therein. In particular, vibration with around 20 Hz giving a rattling feeling to a person in the vehicle is not easily generated. So, if a natural oscillator having a natural frequency in this 20 to 30 Hz range, preferably around 20 Hz is used, the natural oscillator does not act too much even if it acts in response to the input of external vibration in this frequency band, and on the contrary, the sound and vibration information of the cardio-vascular system in the 10 to 40 Hz frequency band is combined with the natural vibration of the natural oscillator 122 in the 20 to 30 Hz range due to a resonant phenomenon or a beat phenomenon, so that the biosignal is emphasized.

When the sound and vibration information with around the natural frequency of the natural oscillators 122, 122 is inputted to the natural oscillators 122, 122, the sound and vibration information is emphasized due to the resonance phenomenon or the beat phenomenon. Consequently, the sound and vibration information of the cardio-vascular system propagated from the back of the trunk via the first layer 11 is emphasized owing to the operation of the natural oscillators 122, 122 (in this specification, this emphasized signal waveform is called a "resonance carrier"). Further, external vibration is inputted to the natural oscillators 122, 122 via the later-described third layer 13. In a static environment as when the sound and vibration information collecting mechanism 10 of this embodiment is disposed on a bed, which is a body support means, at a position corresponding to the back of the trunk, an influence of the external vibration is small, but vibration of the bed in accordance with body motion of the person is inputted as external vibration. In the case of the automobile seat 2, vibration during driving is inputted as the external vibration as described above. Such external vibration, when inputted via the third layer 13, acts on the natural oscillators 122, 122, which makes it possible to capture the resonance carrier with a larger amplitude (refer to later-described test examples).

A microphone sensor 14 is disposed in the second layer 12, in this embodiment, between one of the natural oscillators 122 and the film 123. The microphone sensor 14 functions as a sensor which detects the aforesaid resonance carrier.

The third layer 13 is stacked opposite to the first layer 11 across the second layer 12 and damps the sound and vibration inputted from the outside. For example, in the case where the sound and vibration information collecting mechanism 10 is assembled in the seat back of the automobile seat 2 as in this embodiment, the external vibration is vibration inputted from the vehicle floor via a back frame 2a, and with the third layer 13 being disposed on the back frame 2a side, space is formed between the back frame 2a and the second layer 12, which is the resonance layer, to mechanically filter the external vibration, making it difficult for sound and vibration information in a band of a predetermined high frequency or higher to propagate. The third layer 13 is an external vibration input system (external vibration propagation layer) having a function of thus isolating external vibration in the band of a predetermined high frequency or higher, preferably a high frequency over 100 Hz, and the third layer 13 preferably uses a three-dimensional knitted fabric similarly to the first layer 11 in order to achieve such a filtering function. Incidentally, it is possible to impart a necessary vibration isolating property to the three-dimensional knitted fabric by adjusting the mesh density of the ground knitted fabrics, the thickness and material of the ground yarns, the arrangement density of the connecting yarn, the thickness and material of the connecting yarn, and the like. In this embodiment, as the third layer 13, a three-dimensional knitted fabric whose connecting yarn has a higher arrangement density than those in any of the three-dimensional knitted fabric used as the first layer 11 and the three-dimensional knitted fabrics used as the natural oscillators 122 of the second layer 12 is used, making it difficult for the vibration with the predetermined high frequency or higher to propagate. The third layer 13 isolates the sound and vibration information in a frequency band of a higher frequency than that of the biosignal being the detection target as described above, and preferably damps external sound and vibration with a frequency not corresponding to the natural frequency of the natural oscillators 122. In the above-described example, the natural frequency of the natural oscillators 122 is set to any frequency in the 20 to 30 Hz frequency band, preferably set to around 20 Hz, and accordingly the natural oscillators 122 are preferably adjusted so as to be capable of attenuating (including blocking off) sound and vibration information with 30 Hz or higher.

Here, the properties of the three-dimensional knitted fabrics used as the first layer 11, the third layer 13, and the natural oscillators 122 of the second layer 12 which form the sound and vibration information collecting mechanism 10 of this embodiment and the property of the casing 121 of the second layer 12 will be more specifically described. The three-dimensional knitted fabric forming the first layer 11 and the three-dimensional knitted fabrics forming the natural oscillators 122 of the second layer 12 which are used in this embodiment each have a 10 mm thickness (product number: 49013D (manufactured by Suminoe Textile Co., Ltd.) mentioned above), and the third layer 13 is formed of the three-dimensional knitted fabric having a 7 mm thickness (product number: AKE70042 (manufactured by Asahi Kasei Corporation) mentioned above). FIGS. 5(a), (b) illustrate their load-deflection characteristics. In the measurement, AUTOGRAPH manufactured by Shimadzu Corporation was used and a load up to 100 N was applied in a Z direction in FIG. 2(b) at a moving speed of 50 mm/min by a pressure plate having a 98 mm diameter. FIG. 5(a) illustrates the load-deflection characteristic of the 10 mm thick three-dimensional knitted fabrics forming the first layer 11 and the natural oscillators 122 of the second layer 12, and their spring constants are 28 kN/m. FIG. 5(b) illustrates the load-deflection characteristic of the 7 mm thick three-dimensional knitted fabric of the third layer 13, and its spring constant is 81 kN/m. FIG. 5(c) illustrates the load-deflection characteristic obtained when a load up to 200 N is applied in the Z direction in FIG. 2(b) to a stack of ten pieces of the 5 mm thick casing 121 formed of the bead foam, which is used in the second layer 12, and a spring constant of the 10-piece stack was 127 kN/m, and a spring constant per piece was 1270 kN/m. The casing 121 formed of the bead foam thus has a high spring constant and accordingly achieves functions of restricting the deflection of the natural oscillators 122 formed of the three-dimensional knitted fabrics and preventing bottom touch when a load of the person is applied thereto. FIG. 5(d) illustrates the load-deflection characteristic of the whole sound and vibration information collecting mechanism 10 having the three-layer combination of the first layer 11, the second layer 12, and the third layer 13. The three-layer structure comes to have a 20 kN/m spring constant, and it is seen that the three spring elements function in series arrangement.

FIG. 6 illustrate body pressure distributions of the back of the trunk at the time of a sitting state and a supine state. A pressure distribution measurement system (brand name: BIG-MAT) manufactured by Nitta Corporation was used to measure the body pressure distribution. Subjects are a healthy male who is 172 cm tall and weighs 52 kg (the sitting state in FIG. 6(a)) and a healthy male who is 178 cm tall and weighs 76 kg (the supine state in FIG. 6(b)), and the measurement time is one minute. The positions indicated by the circles in the drawings are each the vicinity of the left fifth intercostal space of the subject, which corresponds to the apex of the heart. A pressure value in a 98 mm diameter range indicated by each of the circles is a load applied to a portion to which the microphone sensor 14 is inserted, and was 15 N at the sitting position and 35 N at the supine position in the case of these subjects. The first heart sound is sound generated due to the closure of the mitral valve and the tricuspid valve in an initial systolic period of the heart and it sounds biggest at the apex of the heart and thus the microphone sensor 14 is preferably provided near this part.

Figure 7:
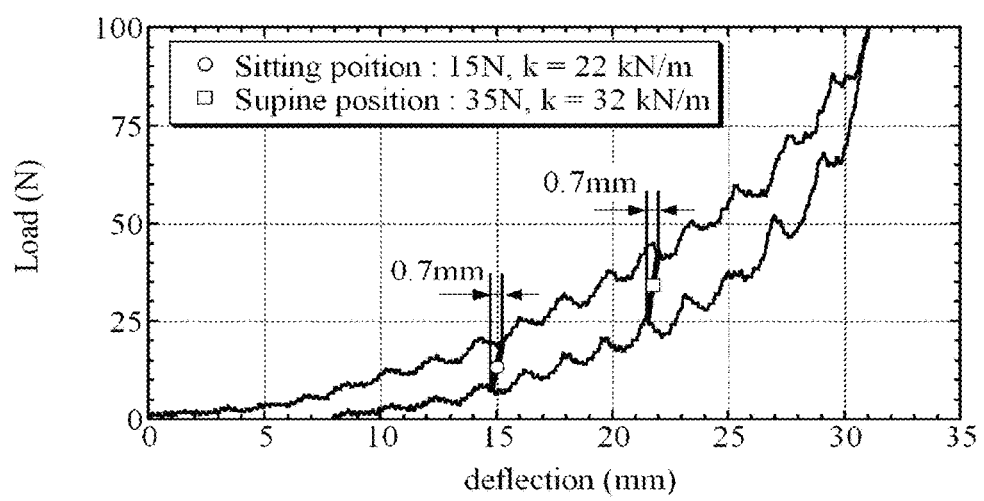
FIG. 7 is a chart illustrating load-deflection characteristics which are measured when a load is applied to the buttocks of a person.

FIG. 7 illustrates measurement results when the pressure plate having a 98 mm diameter is attached to AUTOGRAPH and a load up to 100 N is applied to the buttocks of a person at a moving speed of 50 mm/min. It is known that reactive forces generated due to the deformation of the buttocks at the sitting position and the supine position approximate the values indicated in FIG. 7. As an amplitude value used for finding a dynamic spring constant of the muscle of the person, a variation amount of the person due to body motion is used. So, it is supposed that the reactive forces generated in the person in the sitting and supine states correspond to the minimum value and the maximum value at the time of a posture change respectively and the person side also deflects by the same amount as a deflection amount of the first layer 11. Then, the deflection amount of the first layer 11 when 15 N at the sitting position varies to 35 N at the supine position is 0.7 mm as is found from FIG. 5(a), and it is supposed that this 0.7 mm is a variation value of the deflection of the person side due to the body motion. When the dynamic spring constants of the muscle are found from FIG. 7 at the 15 N point of the sitting position and the 35 N point of the supine position by using this variation value 0.7 mm, they are 22 kN/m and 32 kN/m respectively, and thus it is seen that they approximate the spring constant 28 kN/m of the three-dimensional knitted fabric of the first layer 11. Therefore, the sound and vibration information collecting mechanism 10 of this embodiment including the stacked structure of the three-dimensional knitted fabrics having the 28 kN/m and 81 kN/m spring constants has the function of preventing the bottom touch owing to the three-dimensional knitted fabric of the third layer 13 both in the sitting posture and the supine posture while giving a soft feeling to the person.

In the second layer 12 as the resonance layer, its cutoff frequency as a mechanical filter is preferably set to 100 Hz or higher which is slightly higher than twice the frequencies of the first heart sound (25 to 40 Hz) and the second heart sound (around 50 Hz), in order to capture the sound and vibration information of the cardio-vascular system which is a weak signal, from the back of the trunk. For example, the cutoff frequency is preferably set to a value between 105 to 130 Hz (in this embodiment, 115 Hz). Consequently, a measurement environment of the sound and vibration information with 100 Hz or lower from the trunk is established.

Figure 8:
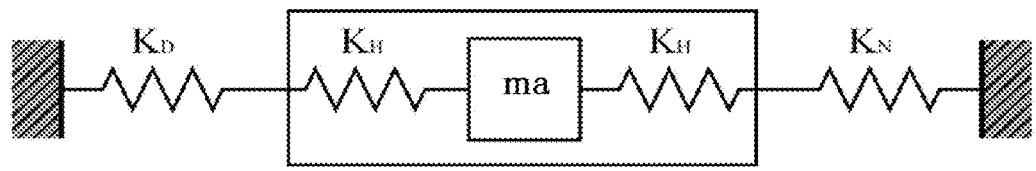
FIG. 8 is a diagram illustrating a vibration model of a resonance layer.

FIG. 8 is a diagram illustrating a vibration model of the second layer 12 which is the resonance layer. In the second layer 12, the air "ma" in the resonance box (in the space surrounded by the casing 121 formed of the bead foam and by the films 123) is vibrated through a spring $K_D$ which causes the string vibration of the connection yarns of the three-dimensional knitted fabrics forming the natural oscillators 122 and through air springs $K_H$.

The cutoff frequency of the bead foam forming the casing 121 being the resonance box is given by substituting the aforesaid spring constant k (1270 kN/m) found from FIG. 5(c) and a mass "m" (3.4 g) of the casing 121 formed of the bead foam, in the following expression (1), and is 96 Hz.

[expression 1]

$$f_0 = \frac{1}{2\pi}\sqrt{\frac{k}{m}} \quad (1)$$

Figure 10:
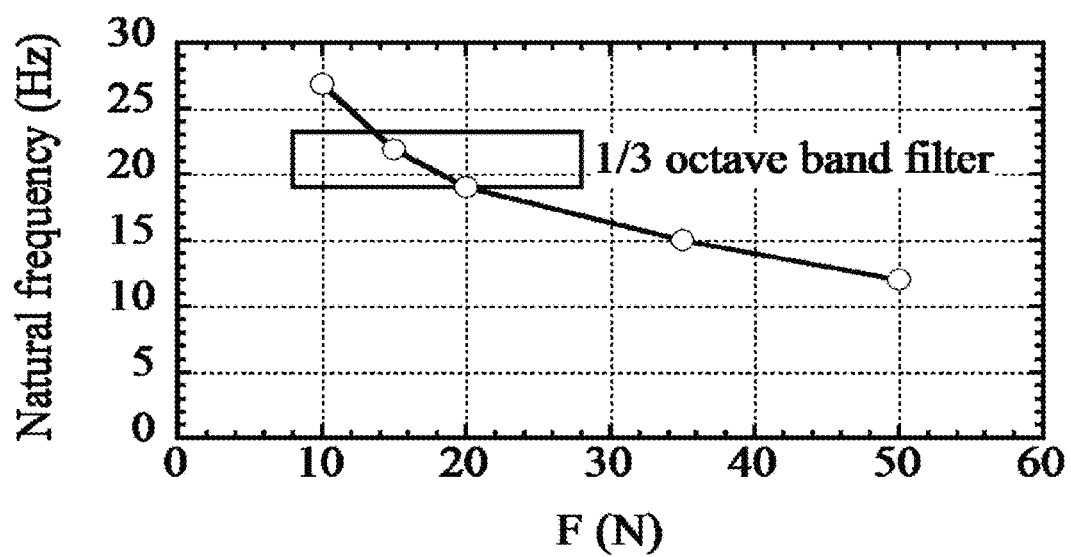
FIG. 10 is a chart illustrating a relation between a natural frequency of the three-dimensional knitted fabric and a load.

The three-dimensional knitted fabrics forming the natural oscillators 122 cause a variation in an air pressure in the resonance box, and their frequency response is found from FIG. 9 which illustrate Bode plots when sinusoidal deflection vibration is applied. As an attenuation ratio, ξ=0.7 and 0.1 obtained from experimental values and analytical values of a prior study (KANEKO Shigehiko, MIYOSHI Ryusuke: "Modeling of air pack sensor equipped with seat for measuring pulse wave", 2008 Japan Society of Mechanical Engineers Symposium on Welfare Engineering, Lecture Proceedings, 08-28 (2008), 185-188) were used, and it was supposed that the attenuation ratio varies between 0.1 and 0.7 depending on how the weight of the subject was applied. The expression (1) gives the natural frequency $f_0$ of the natural oscillators 122 formed of the three-dimensional knitted fabrics. FIG. 10 illustrates the natural frequency corresponding to a load. A load mass "m" varies depending on how the weight of the subject is applied, and it is seen that the natural frequency $f_0$ also varies depending on the load mass "m". The load mass "m" at this time refers to the pressure value illustrated in FIG. 6.

A later-described filtering means 210 of the arithmetic means 20 filters the signal waveform emphasized by the operation of the natural oscillators 122, with a predetermined frequency band to simplify the signal waveform. The filtering means 210 is preferably a band pass filter with a predetermined pass band width having a center frequency within a 20 to 30 Hz range since, as described above, the sound and vibration information collected from the back of the trunk is attenuated by the bones, muscle, skin, and so on to have a signal waveform with around 20 Hz. More preferably, the predetermined band width is set to have the center frequency around 20 Hz. For example, the pass band width can be set to 10 to 30 Hz with its center frequency being 20 Hz. Further, when, for example, the load at the sitting position is 15 N (refer to FIG. 6(a)), the band width can be set narrower with its center frequency being the natural frequency of the natural oscillators 122 at this time. For example, the filtering with a 19 to 23 Hz band width is possible by a ⅓ octave band pass filter. Note that the pass band width of the filtering means 210 differs depending on an applied load, and is sometimes 18 to 24 Hz or the like, for instance.

The following expression (2) gives a frequency (fs) n times as high as that of a string, that causes the string vibration of the connecting yarns of the three-dimensional knitted fabrics forming the natural oscillators 122.

[expression 2]

$$f_S = \frac{v}{\lambda} = \frac{n}{2\ell}\sqrt{\frac{T}{\rho}} \quad (2)$$

(n=1, 2, 3 . . . , "l" is the length of the string of a string structure (10 mm), T is tension of the string structure (0.9 to 1.6 kg), and ρ=line density of the string ($0.2 \times 10^{-6}$ kg/m))

When the load value varies from 15 N to 35 N, the tensions of the three-dimensional knitted fabric of the first layer 11 and the three-dimensional knitted fabrics forming the natural oscillators 122 of the second layers 12 change, and the cutoff frequency of the sound and vibration information collecting mechanism 10 in which the natural oscillators 122 forming the second layer 12 serve as the strings becomes 106 to 141 Hz according to the expression (2).

A cutoff frequency (fv) of the air in the second layer 12 is given by the following expression (3).

[expression 3]

$$f_v = \frac{1}{2\pi}\sqrt{\frac{\gamma \cdot P_0 \cdot S^2}{m \cdot V_0}} \quad (3)$$

(γ: specific heat ratio (1.4), $P_0$: pressure (0.101325 MPa), S: sectional area ($0.35 \times 10^2$), m: air density (1.293 kg/m$^3$)×$V_0$, $V_0$: volume ($5.95 \times 10^{-6}$ m$^3$))

FIG. 11 illustrate Bode plots of the components forming the sound and vibration information collecting mechanism 10. As attenuation ratios, ξ=0.7 and 0.1 obtained from the experimental values and the analytical values of the aforesaid prior study are used. FIG. 11 show that the sound and vibration information collecting mechanism 10 of this embodiment is suitable for collecting the biosignal with 100 Hz or lower, in particular, the sound and vibration information of the cardio-vascular system, which is transmitted through the bones, muscle, skin, and clothes. When the Bode plots of the natural oscillators 122 illustrated in FIG. 9 are overlapped on the Bode plots in FIG. 11, it is seen that the sound and vibration information collecting mechanism 10 has properties, as the mechanical filter, enabling the easy extraction of the sound and vibration information with around 20 Hz of the cardio-vascular system. When the biosignal with 100 Hz or lower (in this embodiment, the 10 to 40 Hz sound and vibration information of the cardio-vascular system) is inputted to the sound and vibration information collecting mechanism 10 having such mechanical properties, the vibration waveforms of the natural oscillators 122 formed of the three-dimensional knitted fabrics are combined with the vibration waveforms generated by the string vibration of the three-dimensional knitted fabric forming the first layer 11, the membrane vibration of the bead foam forming the casing 121 of the second layer 12, and the vibration of the air inside the resonance box surrounded by the casing 121. That is, the sound and vibration information collecting mechanism 10 is a mechanical low pass filter suitable for observing a frequency component with 100 Hz or lower, and with this, the operation of the natural oscillators 122 whose natural frequency is set to around 20 Hz is combined to emphasize the input signal with around 20 Hz, and the microphone sensor 14 detects the resultant as the aforesaid resonance carrier. The microphone sensor 14 adopted in this embodiment has a measurable range of a low-frequency band widened to about 0.1 Hz in order to measure the biosignal highly accurately.

Figure 3:
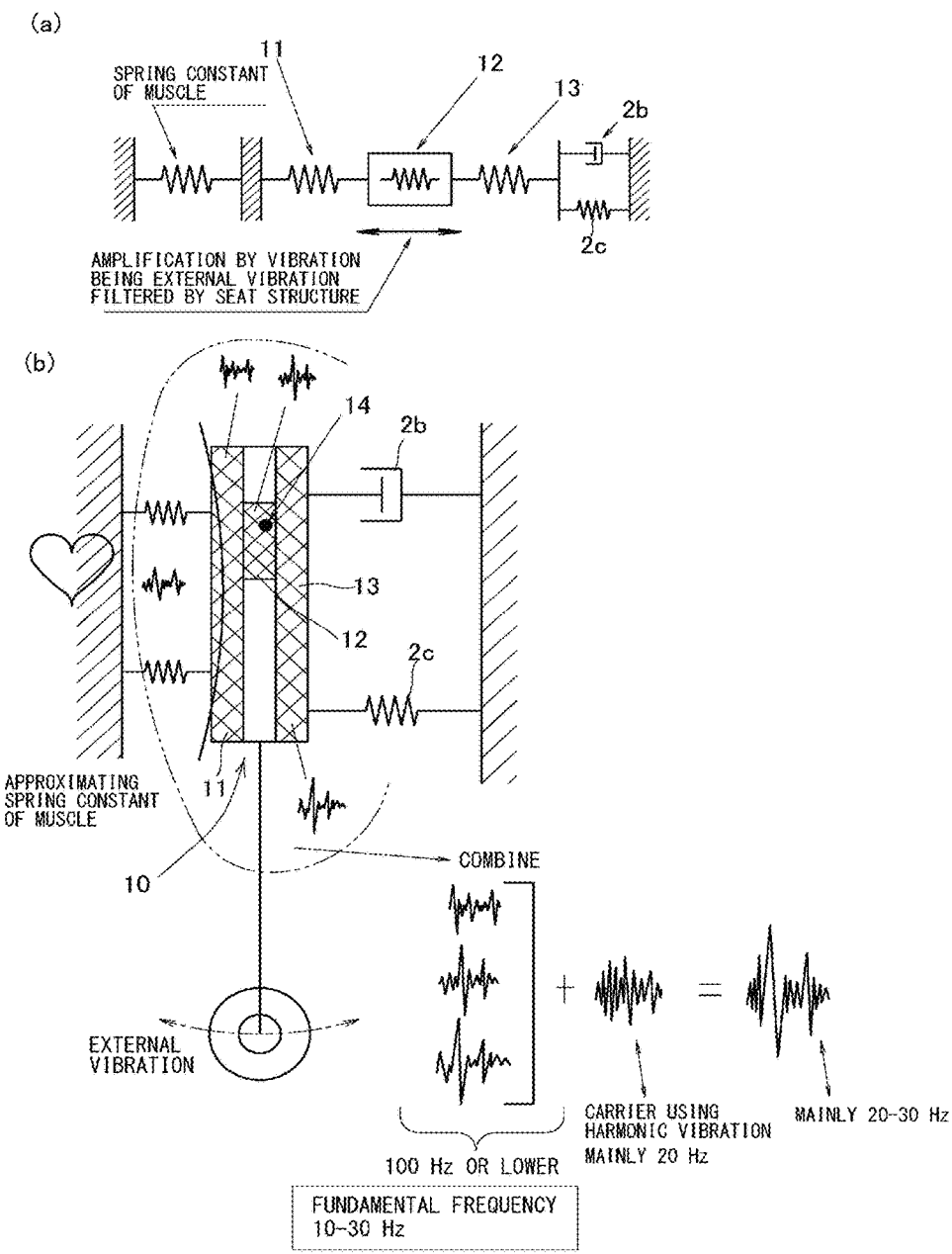
FIGS. 3(a), (b) are explanatory views of the operation of the sound and vibration information collecting mechanism.
Figure 4:
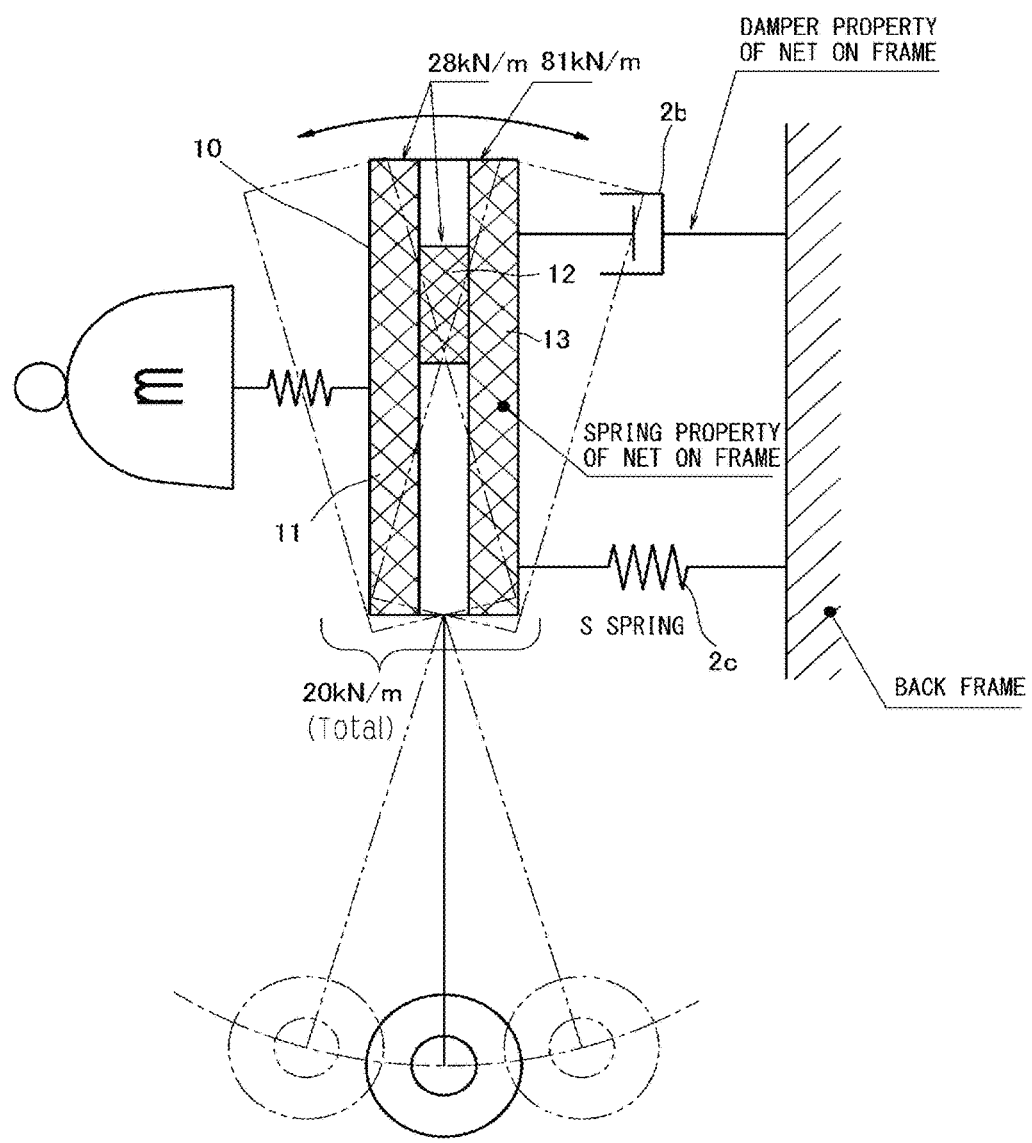
FIG. 4 is an explanatory view of the operation of the sound and vibration information collecting mechanism.
Figure 12:
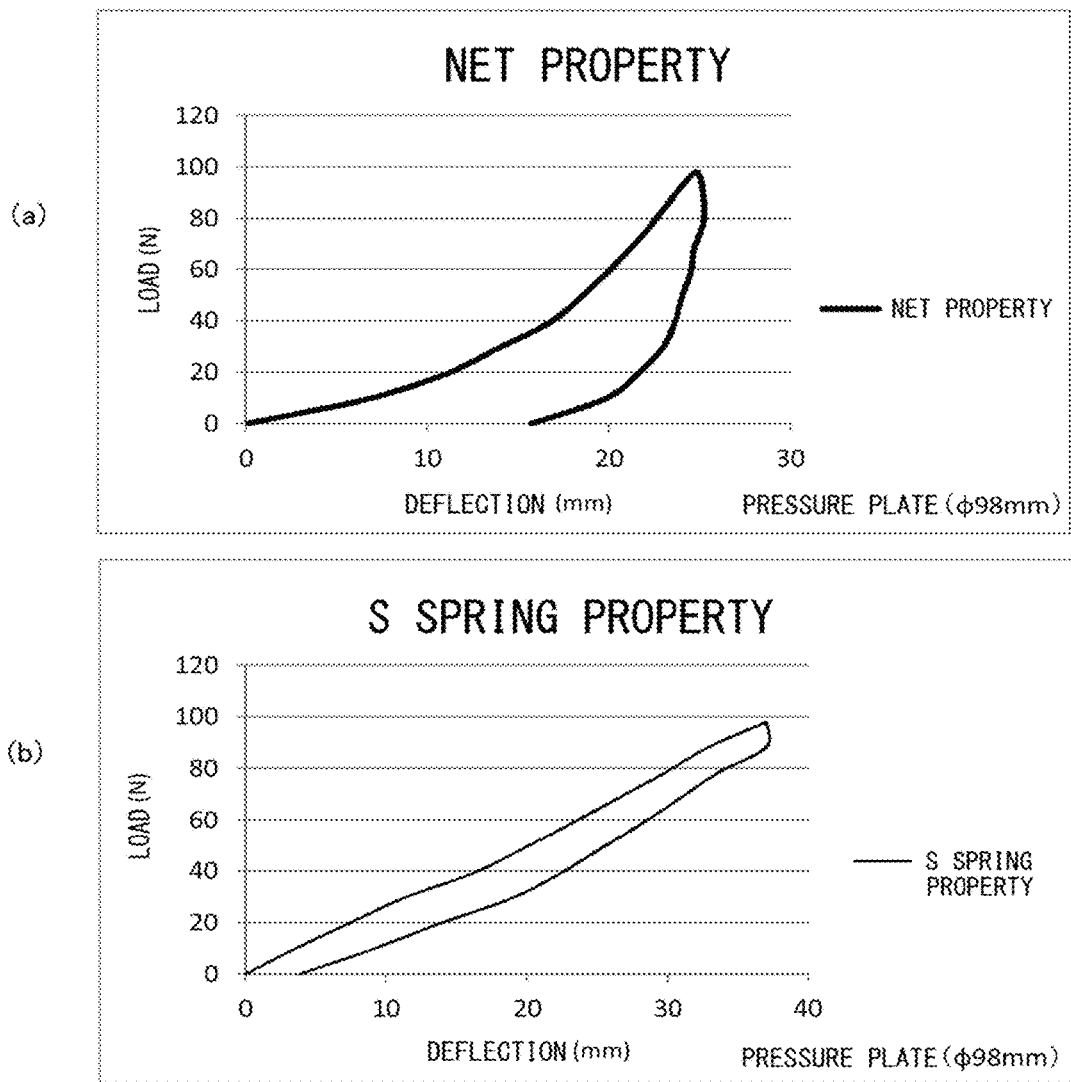
FIG. 12(a) is a chart illustrating a load-deflection characteristic of a back support net.
FIG. 12(b) is a chart illustrating a load-deflection characteristic of an S spring.

Here, FIG. 3 and FIG. 4 are schematic explanatory views of the operation when the external vibration is inputted to the above-described sound and vibration information collecting mechanism 10 through the third layer 13. The three-dimensional knitted fabrics forming the first layer 11 and the second layer 12 each have the spring constant approximating the spring constant of the muscle, and the third layer 13 has a higher spring constant as described above. On the other hand, as the whole sound and vibration information collecting mechanism 10, the spring constant is still lower than that of each of the three-dimensional knitted fabrics since it is composed of the series arrangement of the spring elements each formed of the three-dimensional knitted fabric. When the external vibration is inputted via the back frame 2a, the whole sound and vibration information collecting mechanism 10 is vibrated, but it blocks off high-frequency sound well since the spring constant of the third layer 13 is higher than the spring constants of the first layer 11 and the second layer 12 which are disposed on the person's body side. Further, on the back frame 2a, a back support net 2b extends near a position corresponding to the chest, and an S spring 2c extends along a position corresponding to the lumbar part as illustrated in FIG. 1. FIG. 12(a) illustrates a load-deflection characteristic of the back support net 2b, and FIG. 12(b) illustrates a load-deflection characteristic of the S spring 2c. As is seen, the both have spring constants lower than that of the third layer 13 and are structured to be capable of damping the vibration inputted via the back frame 2a. The back support net 2b, the S spring 2c, and the third layer 13 constitute an external vibration input system, and owing to the operation of these, mainly of the third layer 13, the external vibration to be inputted to the second layer 12 is filtered to a predetermined frequency.

Figure 13:
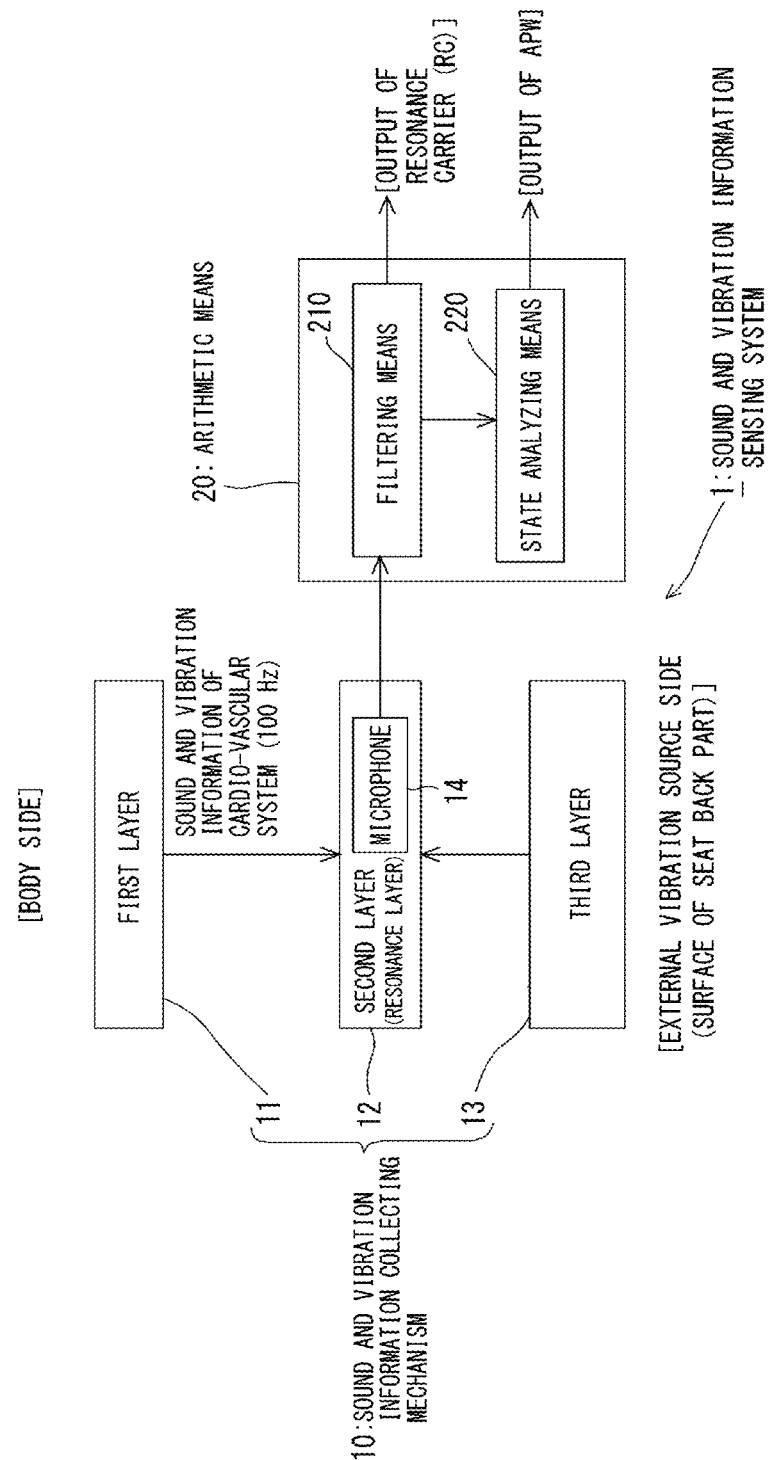
FIG. 13 is a diagram schematically illustrating the structure of the sound and vibration information sensing system.

As illustrated in FIG. 13, the arithmetic means 20 is a means to receive the signal waveform including the resonance carrier which is generated as a result of the emphasizing of the biosignal, in particular, the sound and vibration information of the cardio-vascular system as described above and collected by the microphone sensor 14 of the sound and vibration information collecting mechanism 10, and to arithmetically process the received signal waveform. The arithmetic means 20 is constituted by a computer and includes the filtering means 210 and a state analyzing means 220.

The filtering means 210 realized by a computer program of the arithmetic means 20 executing a filtering procedure filters a microphone sensor output signal including the aforesaid resonance carrier. Here, the first heart sound which differs depending on the heart rate and has an interval of 25 to 45 Hz and the second sound which sounds strong due to a high diastolic pressure of the aorta or the pulmonary artery and has an interval of around 50 Hz both come to have signal waveforms with around 20 Hz after passing through the muscle, bones, skin, and clothes. Since the sound and vibration information, which is the collection target, including the first heart sound and the second heart sound thus comes to have the signal waveform whose frequency is around 20 Hz, the upper limit and lower limit cutoff frequencies of the filtering means 210, which is constituted by a band pass filter, can be set within, for example, 10 to 30 Hz, and further can be set within a narrower band width of 19 to 23 Hz by, for example, the use of the ⅓ octave band pass filter (refer to FIGS. 14(a), (b)). Filtering with the narrower band width also makes it possible to capture the sound and vibration information of the first heart sound and the second heart sound with a distincter interval.

Figure 15:
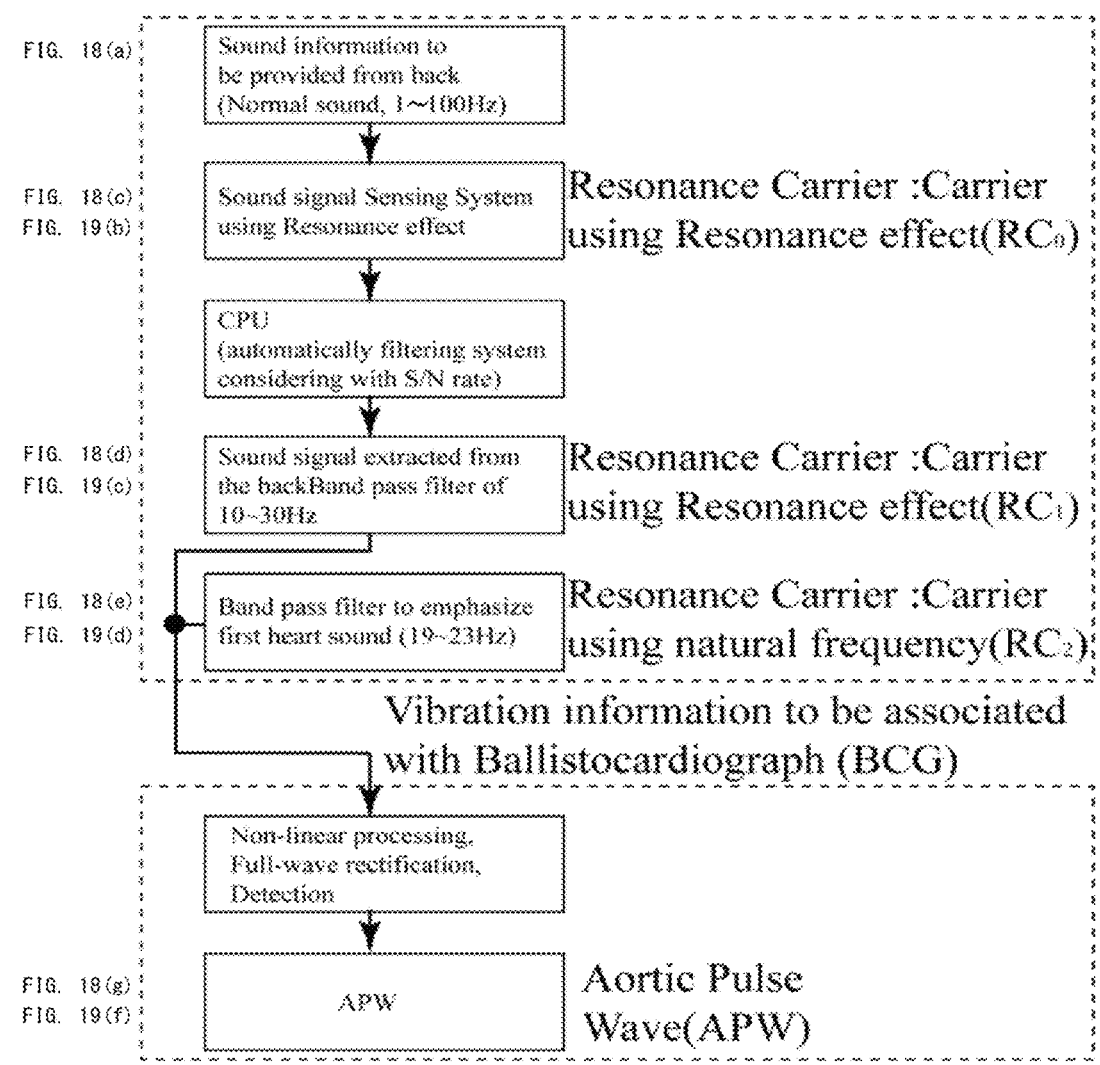
FIG. 15 is an explanatory block diagram of a resonance carrier generated from sound and vibration information from a living body and the vibration of the natural oscillator.

FIG. 15 is a block diagram illustrating signal processing processes in the sound and vibration information sensing system 1. Owing to the mechanical filtering function of the sound and vibration information collecting mechanism 10, the collected biosignal with 100 Hz or lower including the sound and vibration information of the cardio-vascular system is combined with and emphasized by the vibration of the natural oscillators 122 in the second layer 12 as the resonance layer to become the resonance carrier (carrier using resonance effect, hereinafter referred to as "RC" in some case) as described above, and this resonance carrier is detected by the microphone sensor 14 (the resonance carrier detected by the microphone sensor 14 is referred to as "RC0"). RC0 is filtered by a 10 to 30 Hz band pass filter whose center frequency is 20 Hz in the filtering means 210 (a resonance carrier generated as a result of the filtering by the 10 to 30 Hz band pass filter is referred to as "RC1"). Further, in the filtering means 210, RC0 or RC1 is filtered by a 19 to 23 Hz ⅓ octave band pass filter to be found as a resonance carrier "RC2", whereby it is possible to markedly exhibit the combining operation with the biosignal by the natural oscillators 122 having the natural frequency of around 20 Hz.

Incidentally, when an S/N ratio, which is a difference from noise, of the signal based on the sound and vibration information of the trunk which passes through the filtering means 210 to be outputted is small, the center frequency is shifted so that the frequency of the signal is adjusted to an appropriate value.

The state analyzing means 220 realized by the computer program of the arithmetic means 20 executing a state analyzing procedure performs arithmetic processing of a time series waveform of the aforesaid resonance carrier RC0, RC1, or RC2 generated as a result of the filtering by the filtering means 210, finds a vibration waveform (called an aortic pulse wave (APW)) with, for example, around 1 Hz reflecting the autonomic nervous function, and captures cardiac cycle information based on this APW. APW includes information that approximates a ballistocardiogram (hereinafter, referred to as BCG). More specifically, since the resonance carrier RC0, RC1, or RC2 is the carrier including the low-frequency vibration waveform reflecting the autonomic nervous function, the state analyzing means 220 subjects the carrier to full-wave rectification by a detector circuit, demodulates the resultant by finding an envelope by connecting peak values thereof, and extracts APW being the low-frequency biosignal. The extracted APW, which is the biosignal reflecting the autonomic nervous function, is used when, for example, the means described in Patent Documents 1 and 2 described in the section of "Background Art" determines the state of a person (an onset period of a hypnagogic symptom, imminent sleep, or the like, a fatigue degree, under the influence of alcohol or not) and so on by finding a time series waveform of frequency gradient and a time series waveform of frequency fluctuation and analyzing their frequencies.

(Verification Experiments)

Figure 16:
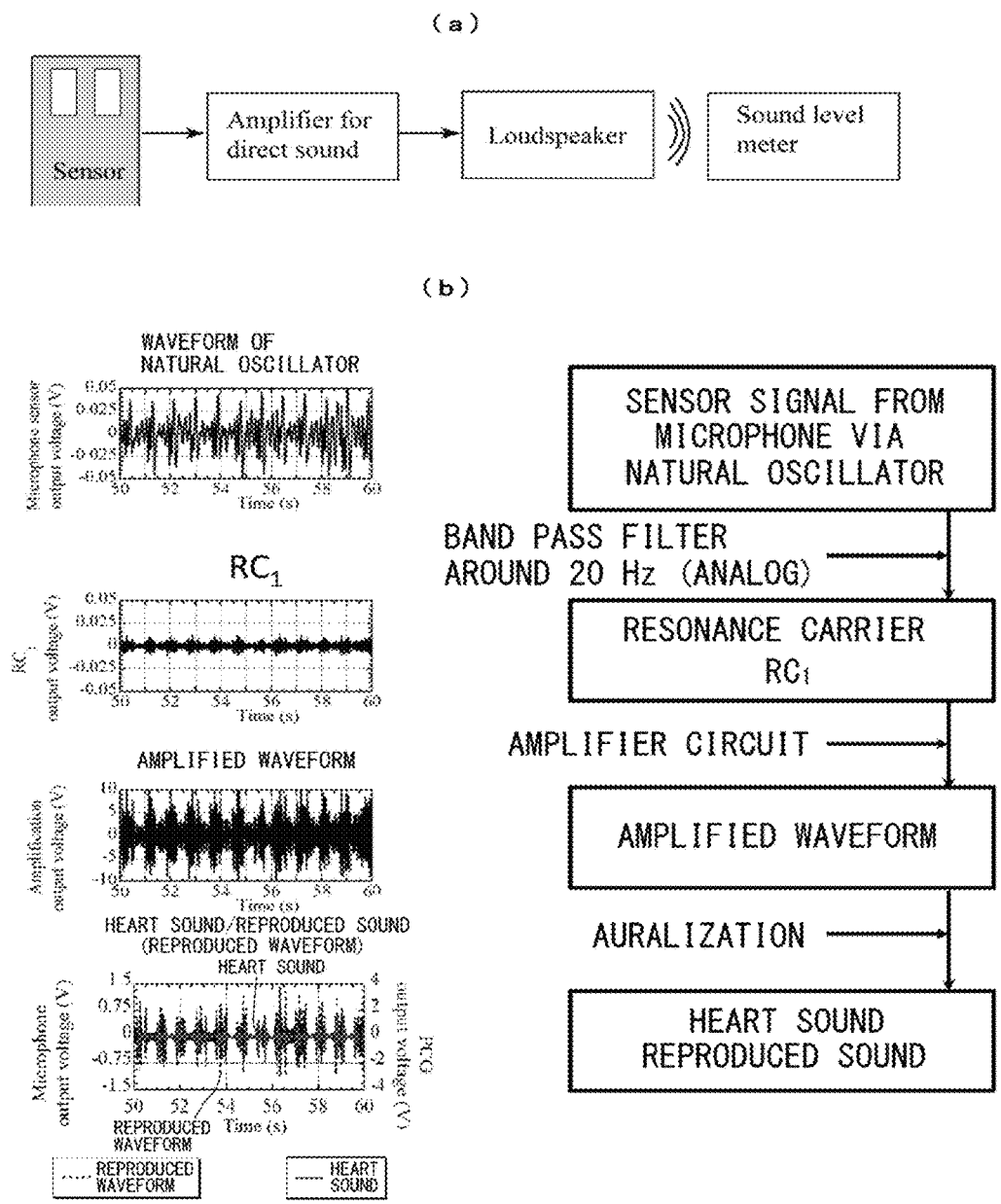
FIG. 16(a) is a diagram schematically illustrating the structure of an audible sound reproduction part including an amplifier and a speaker.
FIG. 16(b) is an explanatory chart of shaping processing and high pass filter processing of the resonance carrier.

Heart sound, an electrocardiogram, a finger plethysmogram, a resonance carrier (RC), and APW were measured and compared under an environment with a small stress, using the sound and vibration information sensing system 1 of this embodiment. The sound and vibration information sensing system 1 can have a structure including an audible sound reproduction part including an amplifier and a speaker as illustrated in FIG. 16(*a*) (for example, Companion 5 multimedia speaker system manufactured by BOSE Corporation). Consequently, the resonance carrier (RC) can be measured as audible sound by being inputted to the amplifier to be amplified and outputted from the speaker. As the resonance carrier (RC) inputted to the amplifier, RC which is an output signal of the microphone sensor 14 may be used, but the use of RC1 or RC2 generated as a result of the filtering of RC by the filtering means 210 can produce more easily audible sound.

However, if the resonance carrier is reproduced as it is by the audible sound reproduction part including the amplifier and the speaker, the reproduced sound becomes sound mainly with 20 Hz attenuated by the muscle, body fluids, and so on of the trunk whichever of RC0, RC1, and RC2 is used, and thus sounds unclear as compared with the heart sound mainly with 25 to 50 Hz heard from the chest side of the person, which involves a possibility that the reproduced sound is recognized as different sound from normally audible heart sound. Even the use of an amplifier and a speaker that have higher performance and are capable of reproducing a low-register results in unclear reproduced sound and does not change the situation much, even though making the reproduced sound easily audible.

So, the resonance carrier (RC0, RC1, or RC2) is subjected to waveform shaping processing and high pass filter processing as illustrated in FIG. 16(*b*). Preferably, the resonance carrier is amplified by an amplifier circuit and an amplified waveform is found, and then the shaping processing is applied to this amplified waveform. Specifically, thresholds are appropriately set on both positive-side and negative-side amplitudes of the amplified waveform, and waveforms at or exceeding the thresholds are cut off, with the peaks of the amplitudes being their centers. Since the resonance carrier has a waveform of a continuous input with mainly 20 Hz, when the waveforms near the peaks are cut, a high-frequency waveform component is generated between the cut waveform components. In the case of the resonance carrier with mainly 20 Hz, a high-frequency component with about 40 Hz or higher which is about twice 20 Hz is superimposed, resulting in a composite wave of the waveform with mainly 20 Hz and the waveform with 40 Hz or higher. The composite wave is filtered by the high pass filter. The high pass filter, whose cutoff frequency is set to, for example, 40 Hz, cuts a low-frequency component with lower than 40 Hz to generate a waveform whose main component is the high-frequency component with 40 Hz or higher (heart sound reproduced waveform). As is apparent from FIG. 16(*b*), this heart sound reproduced waveform (the broken line in the lowest drawing in FIG. 16(*b*) has an interval coinciding with that of the heart sound (the solid line in FIG. 16(*b*)). Then, when this heart sound reproduced waveform is reproduced by the audible sound reproduction part including the amplifier and the speaker as illustrated in FIG. 16(*a*), quasi-heart sound can be heard. The quasi-heart sound mainly includes the frequency component with 40 Hz or higher and thus can be heard as clear sound close to the heart sound heard from the chest side. Further, since its main component is the frequency component with 40 Hz or higher, the amplifier and the speaker used need not have high performance, as compared with a case where a waveform with mainly 20 Hz is reproduced as sound.

A. Methods of Experiments (1) Experiments at the Time of a Sitting Posture Under Static and Dynamic Environments (Active State)

Figure 17:
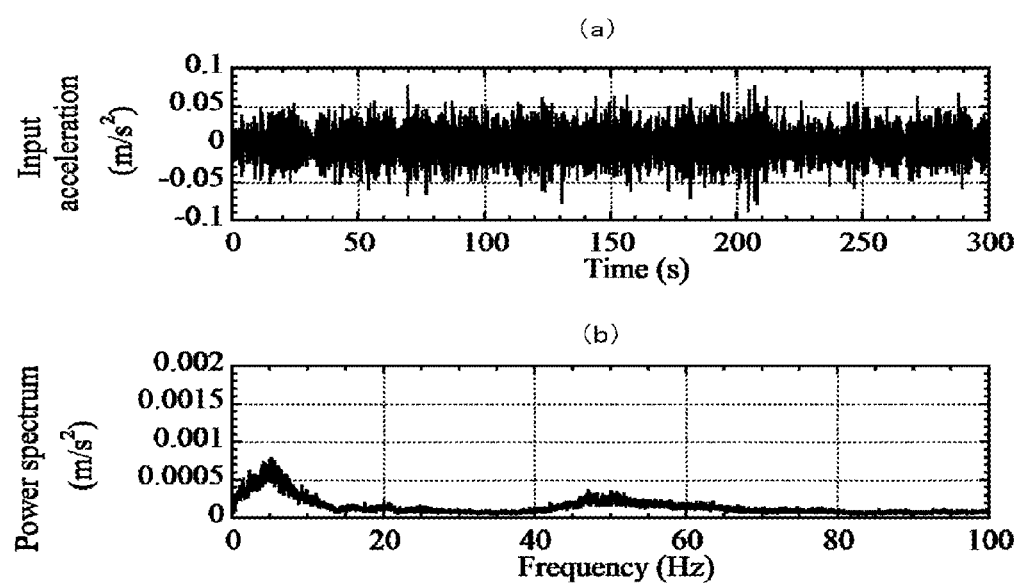
FIG. 17(a) is a chart illustrating a time series signal representing an excitation waveform of a vibrator in an experiment at the time of a sitting posture under a dynamic environment, and (b) is a chart illustrating a frequency analysis result of the time series signal.

The sound and vibration information collecting mechanism 10 was attached to a seat back part of an automobile seat set on a 6-axis vibrator manufactured by DELTA TOOLING Co., Ltd. Each subject was seated, and sound and vibration information which is a biosignal from the back of the trunk of the subject was measured. In order to verify that the sound and vibration information collecting mechanism 10 is little susceptible to noise, the measurement is conducted under a static environment and a dynamic environment. Under the dynamic environment, an up-down direction acceleration waveform which is generated in a floor being a seat attachment part of a standard-sized car when the car travels on the Sanyo Expressway at 80 to 100 km/h was used as an excitation waveform of the vibrator. FIGS. 17(a), (b) illustrate an excitation waveform time series signal and its frequency analysis result. To capture the sound and vibration information from the back of the trunk, an output of the microphone sensor 14 equipped in the sound and vibration information collecting mechanism 10 is used and this output is subjected to the signal processing illustrated as the block diagram in FIG. 15. The subjects are healthy males in their twenties to forties.

As medical indexes for comparison, heart sound (PCG), electrocardiograms (ECG), and finger plethysmograms (PPG) were measured. In the measurement, TA-701T and AS-101D manufactured by Nihon Kohden Corporation were used as a heart sound sensor and a heart sound/pulse wave amplifier, the electrocardiogram was measured from the chest of each of the subjects, using BSM-2301 manufactured by Nihon Kohden Corporation, and Finger Clip Probe SR-5C manufactured by AMCO Inc. was used as a finger plethysmogram sensor. The biosignals were recorded in a data logger at a 200 Hz sampling frequency for five minutes.

(2) Experiment at the Time of a Supine Posture (Resting State)

In order to verify applicability as a simple screening apparatus for determining a biological state, subjects were each made to lie on a bed in a supine state, the sound and vibration information collecting mechanism 10 of this embodiment was in contact with the subject's back when in use, and a biosignal was detected from the back of the trunk under a quiet environment. Further, detection results of the biosignals were compared with heart sound, electrocardiograms, and finger plethysmograms as in the above case of the sitting posture. The biosignals were recorded in a data logger at a 200 Hz sampling frequency for five minutes. An S/N ratio was found based on comparison between a state where a weight corresponding to a pressure value applied to a part corresponding to the microphone sensor 14 equipped in the vibration information collecting mechanism 10 was placed and the state where the subject was supine. The subjects are fifteen healthy males in their twenties to thirties. The height, weight, and BMI of each of the fifteen subjects were as follows.

Subject A . . . height: 1.53 m, weight: 52 kg, BMI: 22.2
Subject B . . . height: 1.72 m, weight: 59 kg, BMI: 19.9
Subject C . . . height: 1.74 m, weight: 70 kg, BMI: 23.1
Subject D . . . height: 1.74 m, weight: 65 kg, BMI: 21.5
Subject E . . . height: 1.75 m, weight: 78 kg, BMI: 25.5
Subject F . . . height: 1.74 m, weight: 60 kg, BMI: 19.8
Subject G . . . height: 1.67 m, weight: 64 kg, BMI: 22.9
Subject H . . . height: 1.73 m, weight: 70 kg, BMI: 23.4
Subject I . . . height: 1.70 m, weight: 63 kg, BMI: 21.8
Subject J . . . height: 1.71 m, weight: 57 kg, BMI: 19.5
Subject K . . . height: 1.70 m, weight: 55 kg, BMI: 19.0
Subject L . . . height: 1.69 m, weight: 60 kg, BMI: 21.0
Subject M . . . height: 1.67 m, weight: 58 kg, BMI: 20.8
Subject N . . . height: 1.79 m, weight: 69 kg, BMI: 21.5
Subject O . . . height: 1.65 m, weight: 75 kg, BMI: 27.5

B. Results of Experiments and Discussion (1) The Experiments at the Time of the Sitting Posture Under the Static and Dynamic Environments (Active State)

Figure 18:
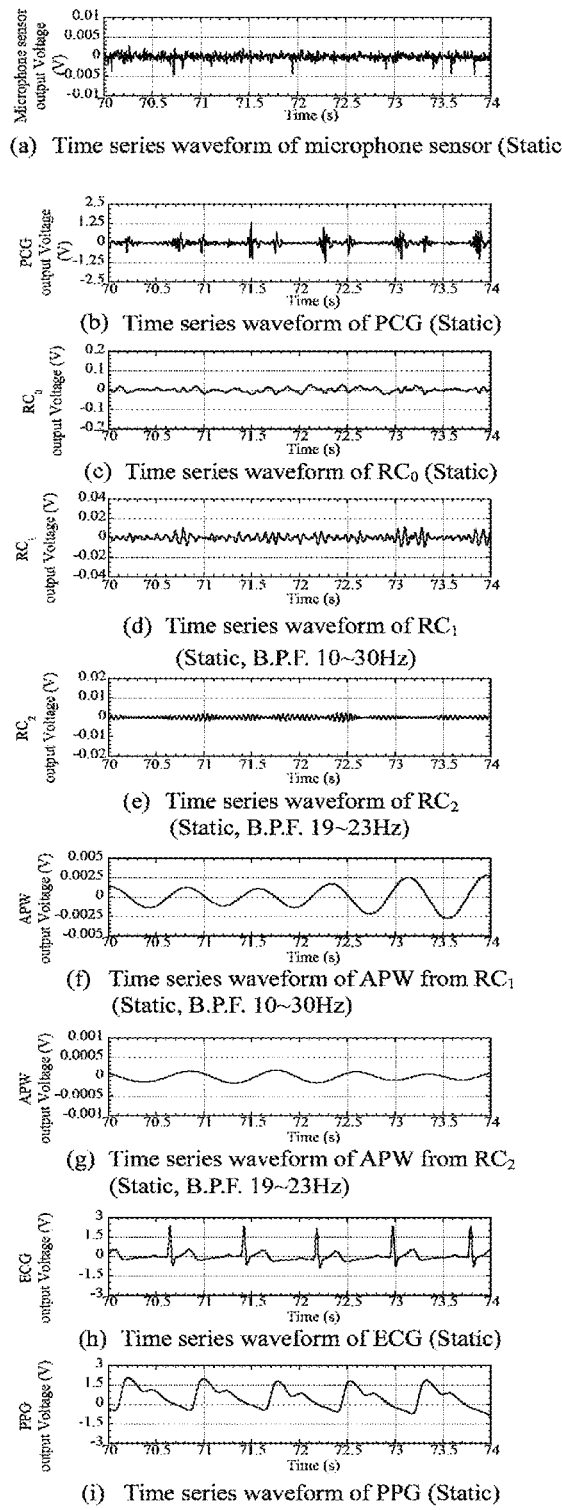
FIGS. 18(a) to (i) are charts illustrating time series signals outputted at respective stages of the block diagram in FIG. 15, in an experiment at the time of the sitting posture under a static environment.
Figure 19:
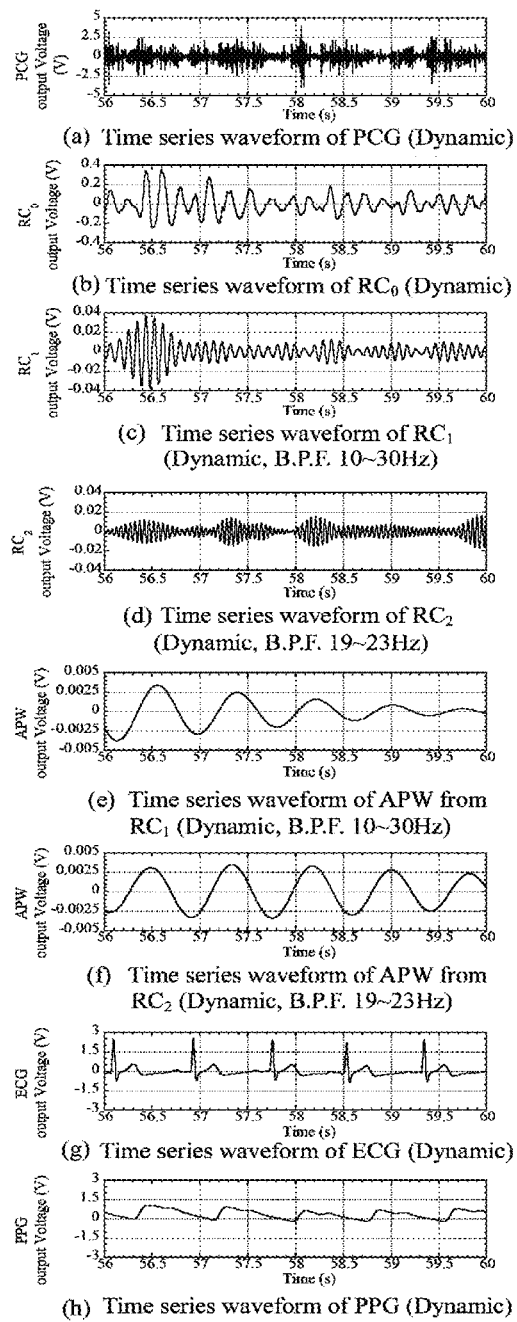
FIGS. 19(a) to (h) are charts illustrating time series signals outputted at the respective stages of the block diagram in FIG. 15, in the experiment at the time of the sitting posture under the dynamic environment.
Figure 20:
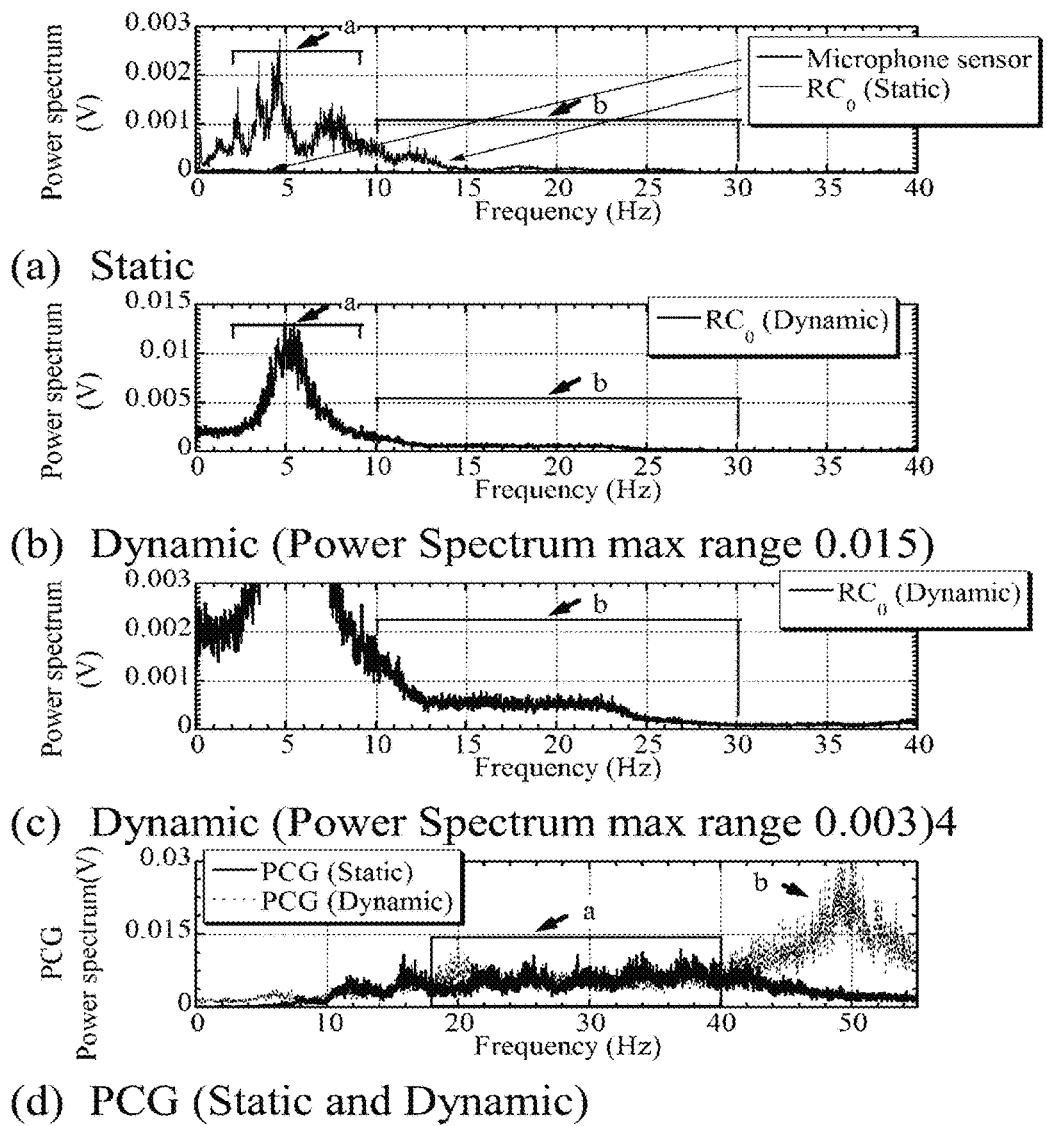
FIG. 20(a) is a chart illustrating frequency analysis results of FIG. 18(a) and FIG. 18(c)
FIG. 20(b) is a chart illustrating a frequency analysis result of FIG. 19(b)
FIG. 20(c) is an enlarged chart of FIG. 20(b), in a different range of the vertical axis from that in FIG. 20(b).
FIG. 20(d) is a chart illustrating frequency analysis results of PCGs captured under the static and dynamic environments during the same time zone as that in FIGS. 20(a), (b), (c).
Figure 21:
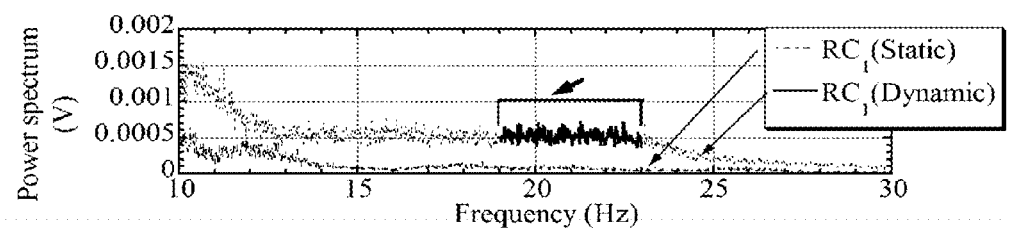
FIG. 21 is a chart illustrating frequency analysis results of time series signals RC1 illustrated in FIG. 18(d) and FIG. 19(c).
Figure 22:
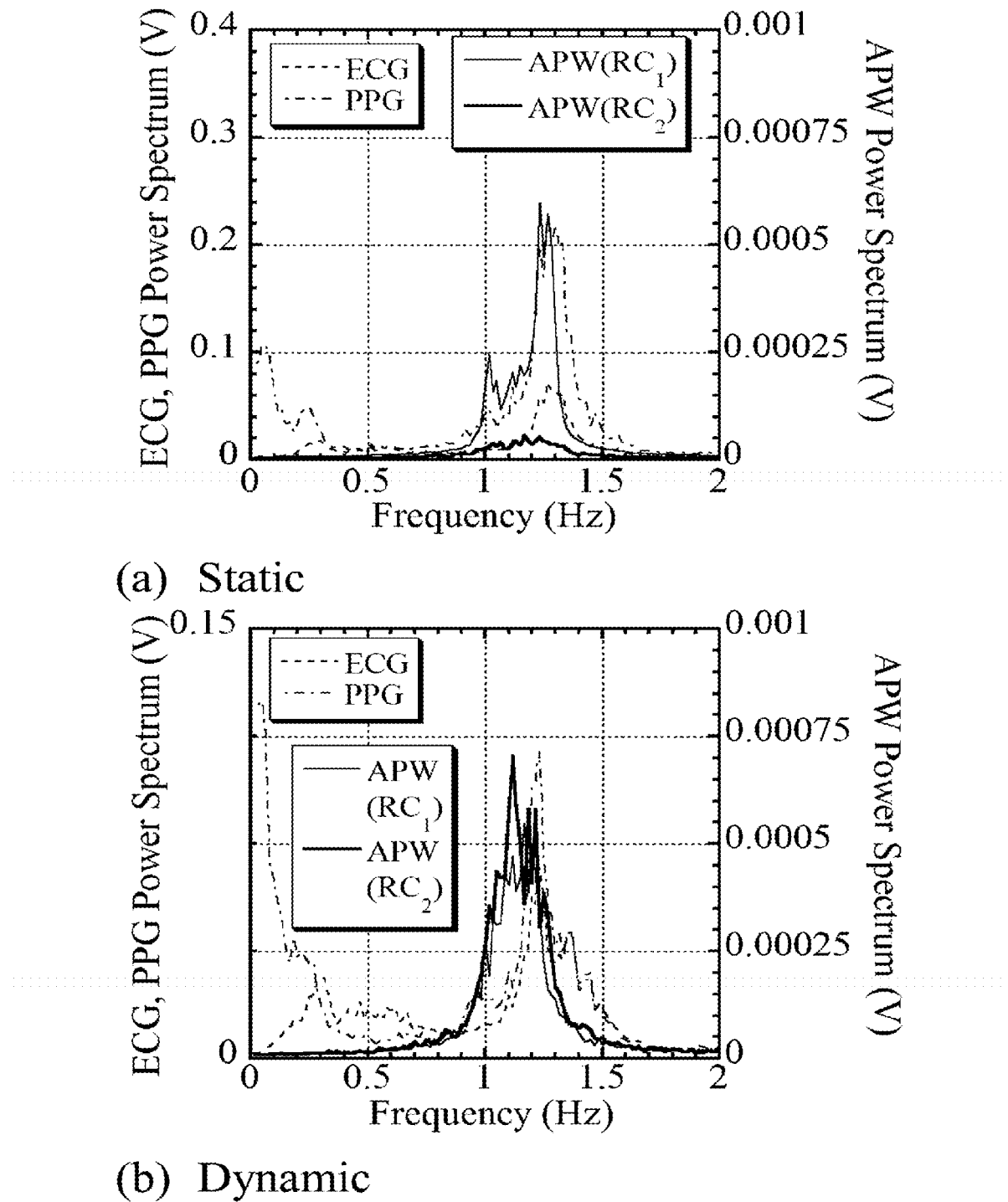
FIG. 22(a) is a chart illustrating frequency analysis results of time series waveforms of APWs which are found using RC1 and RC2 under the static environment.
FIG. 22(b) is a chart illustrating frequency analysis results of time series waveforms of APWs which are found using RC1 and RC2 under the dynamic environment.

FIG. 18 and FIG. 19 illustrate time series signals outputted at the respective stages of the block diagram in FIG. 15. Among these, FIG. 18 illustrate the time series signals under the static environment, and FIG. 19 illustrate the time series signals under the dynamic environment. FIG. 20 to FIG. 22 illustrate results of frequency analysis of the time series signals.

The biosignal illustrated in FIG. 18(a) is data measured when the microphone sensor is directly pasted on the body of the subject, and the biosignals illustrated in FIG. 18(b) and FIG. 19(a) are data measured when the heart sound sensor is directly pasted on the body of the subject. The sensitivity of the microphone sensor used here can achieve only a small power spectrum and does not enable to completely capture the heart sound component as illustrated in FIG. 20(a).

On the other hand, the frequency analysis of the time series waveforms of the resonance carriers (RC0) of the sound and vibration information collecting mechanism 10 of this embodiment shows that pressure variation components with around 1 Hz corresponding to BCG are not easily discriminated due to noise which is generated in a frequency band of 5 Hz or lower as indicated by the arrows "a" in FIGS. 20(a), (b) due to body motion and an external vibration input. However, when frequency components with 10 Hz or higher are analysis targets, it is understood that components corresponding to signals measured by the heart sound sensor are captured as indicated by the arrows "b" in FIGS. 20(a), (b), (c). FIG. 20(d) illustrates PCGs captured under the static and dynamic environments during the same time zone as that in FIGS. 20(a), (b), (c). From frequency analysis results of these PCGs, it is seen that the first heart sound with 25 to 45 Hz and the second heart sound with around 50 Hz are captured (frequency band indicated by the arrows "a" in FIG. 20). Therefore, a difference in frequency between PCG and RC0 indicates that the first heart sound with 25 to 45 Hz and the second heart sound with around 50 Hz in PCG, after passing through the muscle, bones, skin, and clothes, can be captured as the signal (RC0) with around 20 Hz. Incidentally, the waveform indicated by the arrow "b" in FIG. 20(d) is thought to be that of noise generated under the dynamic environment. Data on the other two subjects also presented the same tendency.

The data in FIG. 18 and FIG. 19 will be further discussed on the premise of the above points. First, the time series signals RC0 illustrated in FIG. 18(c) and FIG. 19(b) capture the sound and vibration information corresponding to the heart sound components as indicated by the arrows "b" in FIGS. 20(a), (c), but when RC0s emphasized by the natural oscillators 122, which are the output signals from the microphone sensor 14, are simply used as they are, the heart sound components are buried in the time series waveforms in FIG. 18(c) and FIG. 19(b) due to the low-frequency noise and external vibration input, which are indicated by the arrows "a" in FIGS. 20(a) to (c), appearing in 5 Hz or lower ascribable to respiratory components, a temperature drift amount, and a measurement error.

FIG. 18(d) and FIG. 19(c) illustrate the time series signals RC1 generated as a result of the filtering of RC0s by the 10 to 30 Hz band pass filter in the filtering means 210, and FIG. 21 illustrates frequency analysis results thereof. Comparison of the time series waveforms of RC1s with the time series waveforms of the heart sound sensor in FIG. 18(b) and FIG. 19(a) shows that the amplitudes of the time series waveforms vary to increase and decrease at almost the same timing, and thus it is understood that the signals corresponding to the first and second heart sounds are captured as signals having a frequency band of around 10 to 30 Hz as a result of the filtering by the 10 to 30 Hz band pass filter.

FIG. 18(e) and FIG. 19(d) each illustrate the resonance carrier RC2, which is indicated by the arrow in FIG. 21, generated as a result of the filtering of RC1 by the 19 to 23 Hz band pass filter in the filtering means 210. It is seen that RC2 becomes close to simple sound with only a little distortion. In particular, under an environment having large noise, when the range of the band pass filter is narrowed to around 20 Hz in which the natural oscillators 122 function and RC2 is captured, its waveform has only a little distortion.

FIG. 18(f) and FIG. 19(e) each illustrate a time series waveform of APW that the state analyzing means 220 obtains by using RC1. FIG. 18(g) and FIG. 19(f) each illustrate a time series waveform of APW obtained using RC2. The intervals of these time series waveforms of APWs exist around 1 Hz as illustrated in FIG. 22, and it is seen that these time series waveforms are highly correlated with heartbeat fluctuations captured from the electrocardiograms and the finger plethysmograms, irrespective of whether the environment is the static environment or the dynamic environment. When the time series waveforms in the static state in FIG. 18 and the dynamic state in FIG. 19 are compared, the amplitudes of the time series waveforms of RC1 and RC2 having undergone the respective band pass filters and the amplitudes of the time series waveforms of APWs found from these are both larger in the dynamic state than in the static state, which shows that the external vibration increases the operation of the natural oscillators 122.

FIG. 23 illustrate processes where the natural oscillators 122 function in response to the external vibration input to generate the composite wave. FIG. 23(a) illustrates a time series waveform of the inputted external vibration, and FIG. 23(b) illustrates a time series waveform of RC0 which is the composite wave of the waveform generated by the natural oscillators 122 which function in response to the external vibration input and the sound and vibration waveform of the cardio-vascular system. It is seen that, in a time zone when the external vibration input is large, that is, a time zone when the amplitude of the time series waveform of the external vibration is large, the amplitude of the composite wave also becomes large. FIG. 23(c) illustrates a time series waveform of RC2 generated as a result of the filtering by the 19 to 23 Hz band pass filter in the filtering means 210, and RC2 also has the same tendency as that of RC1. FIG. 23(d) illustrates APW found from RC2, and its interval coincides with an R-R interval (RRI) of the electrocardiogram.

Next, a description will be given of processes of generating the time series waveform, which is illustrated in FIG. 19(d), generated as a result of the filtering of the output signal from the microphone sensor 14 by the 19 to 23 Hz band pass filter under the dynamic environment. First, let us suppose that two simple harmonic oscillations "x1=a cos ω1t", "x2=b cos ω2t" different in amplitude and frequency are combined. The following expression (4) is the result of the combination.

[expression 4]

$$x = \sqrt{a^2 + b^2 + 2ab \cdot \cos(\omega_2 - \omega_1)t} \cdot \cos\frac{\omega_1 - \omega_2}{2}t \cdot \cos\frac{\omega_1 + \omega_2}{2}t \quad (4)$$

If the expression (4) is transformed, supposing that "ω2=ω1+Δω", the expression (5) is obtained, and the composite wave expressed by the expression (5) is the time series waveform in FIG. 19(d).

[expression 5]

$$x = \sqrt{a^2 + b^2 + 2ab \cdot \cos\Delta\omega t} \cdot \cos\frac{\Delta\omega}{2}t \cdot \cos\left(\omega_1 + \frac{\Delta\omega}{2}\right)t \quad (5)$$

Figure 24:
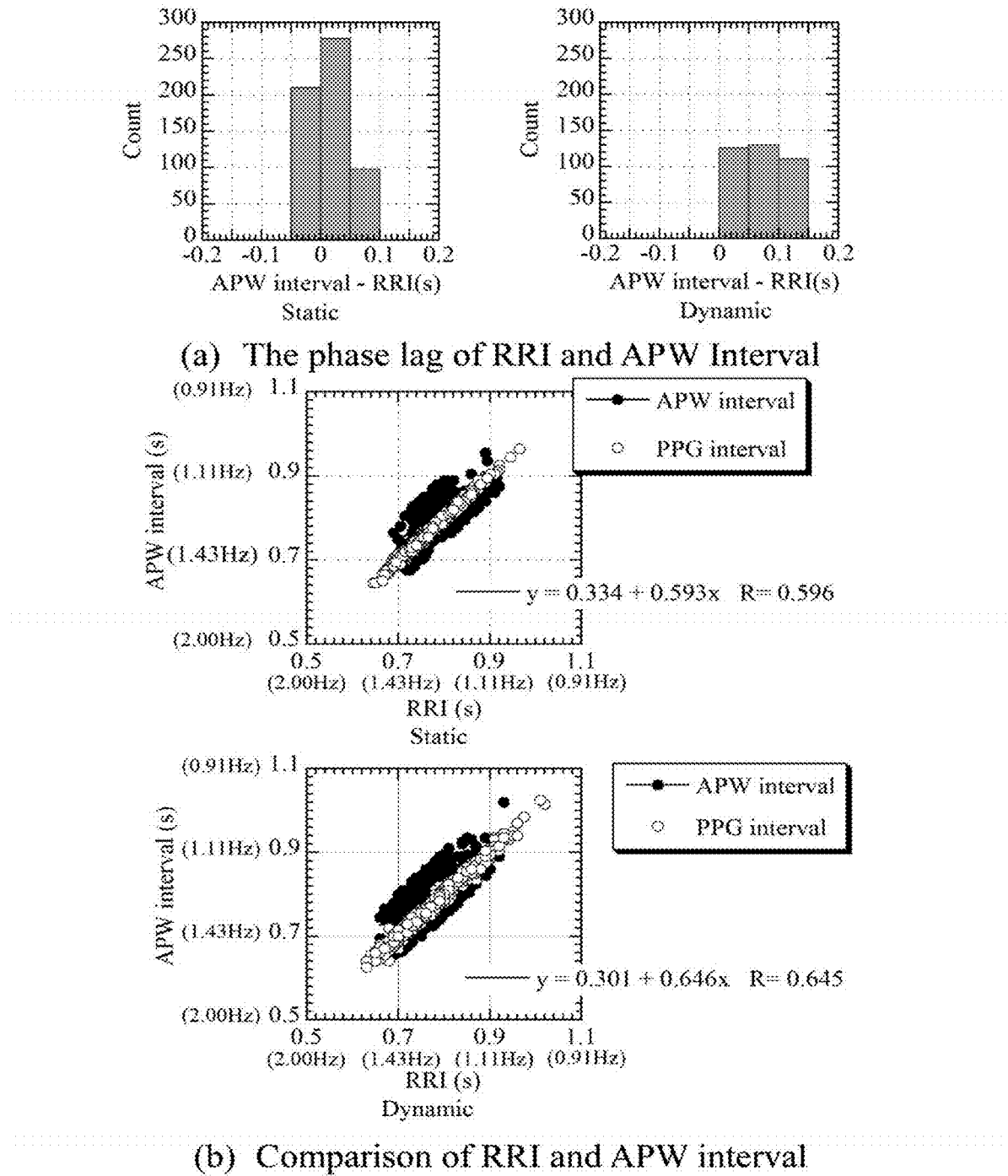
FIGS. 24(a) and (b) are charts illustrating phase lag amounts of intervals of APWs from intervals of electrocardiograms, and correlations between the intervals, respectively.

The intervals of APWs, which are illustrated in FIG. 18(g) and FIG. 19(f), found from RC2s by the arithmetic processing have phase lags from the intervals obtained from the electrocardiograms and the phonocardiograms illustrated in FIGS. 18(h), (i) and FIGS. 19(g), (h) due to deviation in an interval of "Δω/2" and a phase lag due to the filtering operation. FIG. 24 illustrate phase lag amounts and interval correlations.

From FIG. 24(a), the phase lag amounts of RRIs in the electrocardiograms and APWs in the wakeful state at the time of the sitting posture under the static and dynamic environments are within 0.15 seconds, and from FIG. 24(b), a correlation coefficient between RRI in the electrocardiogram and the interval of APW is Rs=0.596 in the static state and Rd=0.645 in the dynamic state, and thus APWs presented a high correlation as the biosignals.

(2) Experiment at the Time of the Supine Posture (Resting State)

Figure 25:
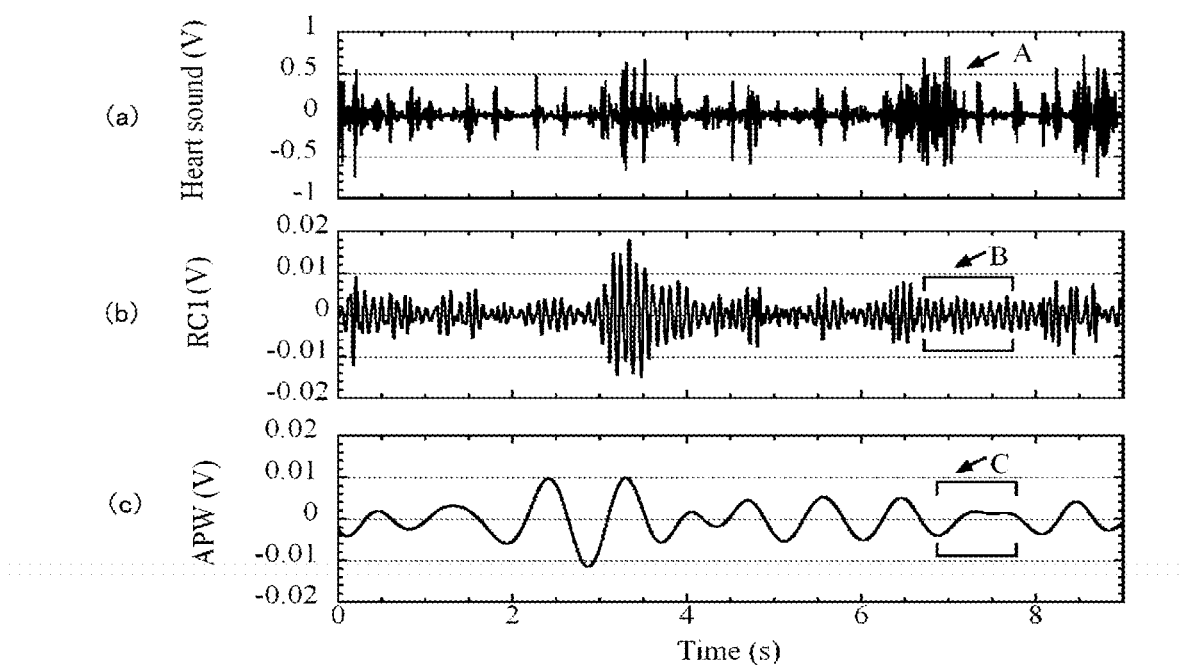
FIG. 25 illustrate results of experiments at the time of a supine posture, (a) illustrating a time series waveform of heart sound, (b) illustrating a time series waveform of RC1, and (c) illustrating a time series waveform of APW.

FIG. 25 illustrate typical examples of measurement results in the resting supine state where disturbance does not easily enter. It has been found out that a time series waveform of RC1 generated as a result of the filtering of an output waveform of the sound and vibration information collecting mechanism 10 by the 10 to 30 Hz band pass filter in the filtering means 210 of the arithmetic means 20 (FIG. 25(b)) is synchronous with a waveform of first and second heart sounds collected by the heart sound sensor (FIG. 25(a)). FIG. 25(c) illustrates a waveform of APW which is obtained when the state analyzing means 220 of the arithmetic means 20 further subjects RC1, which is generated as a result of the processing by the filtering means 210, to the arithmetic operation by full rectification and detection. The obtained waveform of APW is a waveform with around 1 Hz and approximates that of a ballistocardiogram (BCG) which indicates the motion of the heart and blood vessels. Incidentally, the waveform indicated by the arrow A in FIG. 25(a) is thought to be that of extrasystole, and at an instant when this waveform appears, the waveform of RC1 and the waveform of APW both changed as indicated by the sign B in FIG. 25(b) and the sign C in FIG. 25(c). Incidentally, it was possible to output an output signal of RC1 as 72.8 dB sound via the amplifier and the speaker illustrated in FIG. 16.

Figure 26:
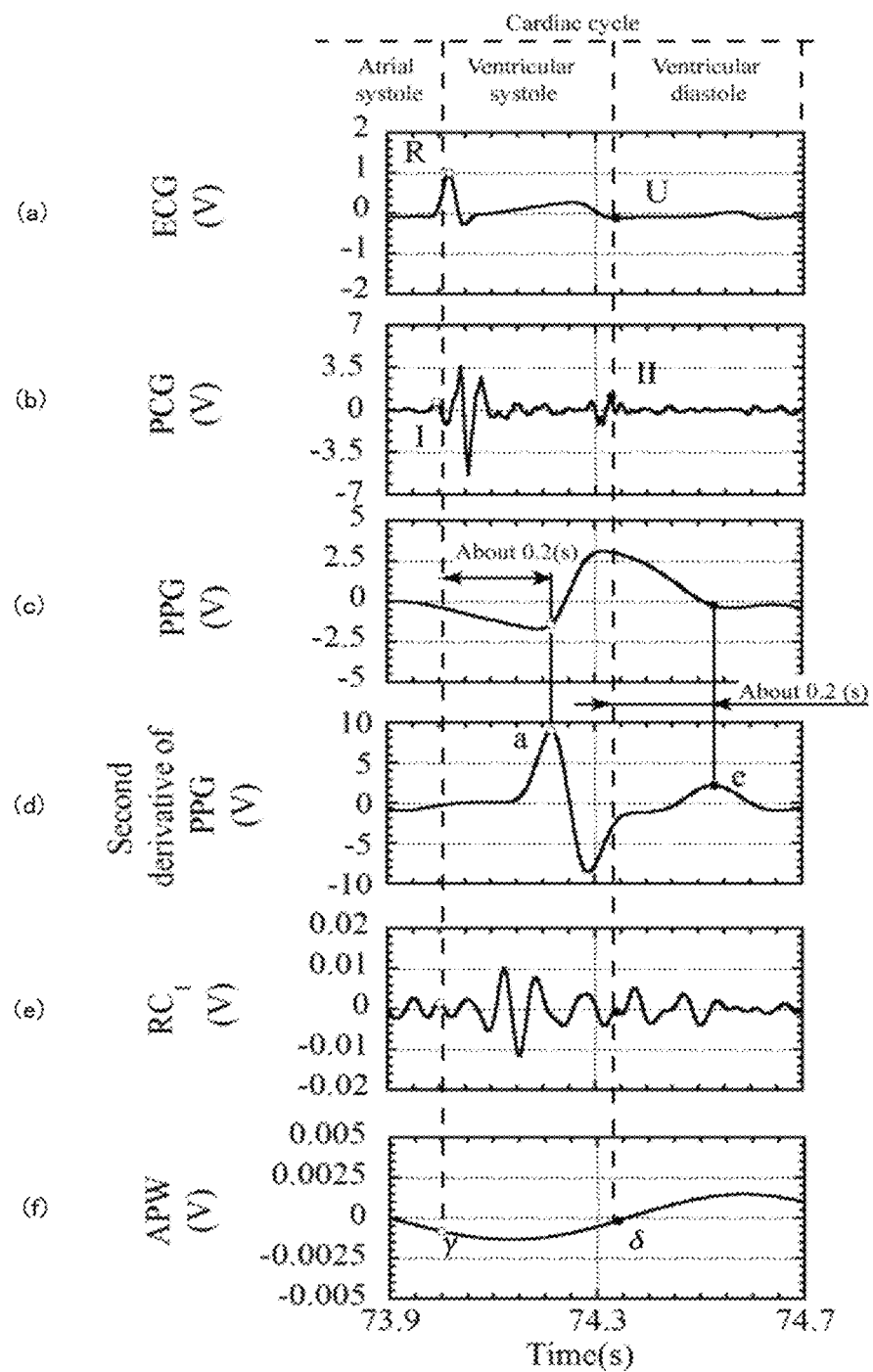
FIG. 26 illustrate results of the experiments at the time of the supine posture, (a), (b), (c), (d), (e), and (f) being charts illustrating data of an electrocardiogram, heart sound, a finger plethysmogram, an acceleration pulse wave, RC1, and APW respectively.
Figure 27:
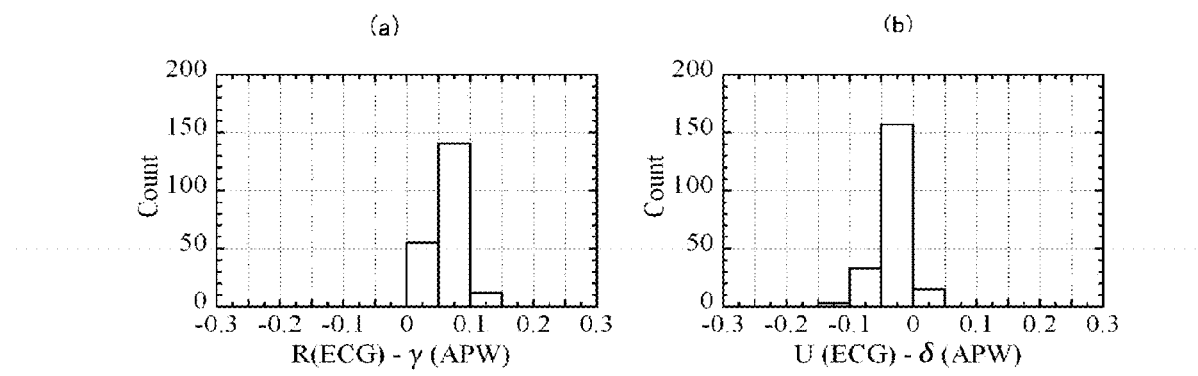
FIGS. 27(a), (b) are charts illustrating lag times in a time base between related phenomena in the whole heart stroke cycle covering the atrial systole, the ventricular systole, and the ventricular diastole, and APW obtained from a resonance carrier.
Figure 28:
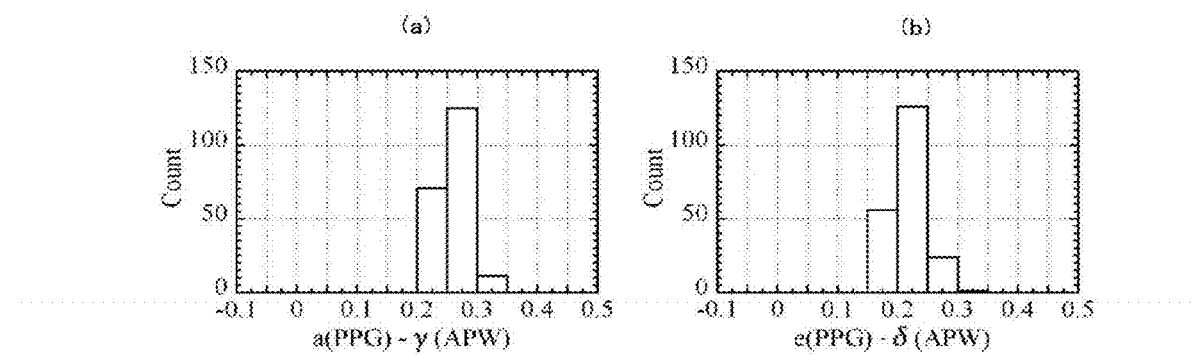
FIGS. 28(a), (b) are comparative charts of variance degrees of the lag time between the acceleration pulse wave found from an acceleration which is the time for the transmission to a periphery and APW.

FIG. 26 to FIG. 28 illustrate typical cases of the experiment results. Among these, FIG. 26 are charts comparing an electrocardiogram (a), heart sound (b), a finger plethysmogram (c), a second derivative waveform of the finger plethysmogram (d), a waveform of RC1 (e), and a waveform of APW (f) in phases of the cardiac cycle in the resting supine state where disturbance is not easily enter. In this case, a heart rate is 61 times/minute. The output waveform of RC1 is synchronous with the first and second heart sounds captured by the heart sound sensor, and this output waveform is converted to APW, which is a low-frequency vibration waveform with around 1 Hz, through the full rectification and detection. The finger plethysmogram coincided with APW, only with a 0.2 second lag corresponding to the pulse wave propagation time of a healthy young person.

FIG. 27 illustrate results of studies on lag time in a time base between related phenomena in the whole heart stroke cycle covering the atrial systole, the ventricular systole, and the ventricular diastole, and APW obtained from the waveform of the resonance carrier (RC1), (a) illustrating a lag time (R–γ) between an R point in the electrocardiogram and a γ point in the waveform of APW, corresponding to the R point, (b) illustrating a lag time (U–δ) between a U point in the electrocardiogram and a δ point in the waveform of APW, corresponding to the U point. From FIG. 27, the lag times are both 0.1 seconds, which corresponds to a ½ waveform of the resonance carrier and is within a range of an error by mechanical determination.

In FIG. 28, variance degrees of the lag time between the acceleration pulse wave found from an acceleration which is the time for the transmission to a periphery and APW are compared. (a) illustrates the variance degree of the lag time (a–γ) between an "a" point of the second derivative and the γ point of APW, and (b) illustrates the variance degree of the lag time (e–δ) between an e point of the acceleration pulse wave and the δ point of APW. The pulse touched by the artery of a fingertip delayed from the peak of blood ejection from the left ventricle to the aorta by about 0.2 to 0.3 seconds in almost all the data, and the data of this subject was data that can be said as being a pulse wave propagation rate of a healthy young person.

Figure 29:
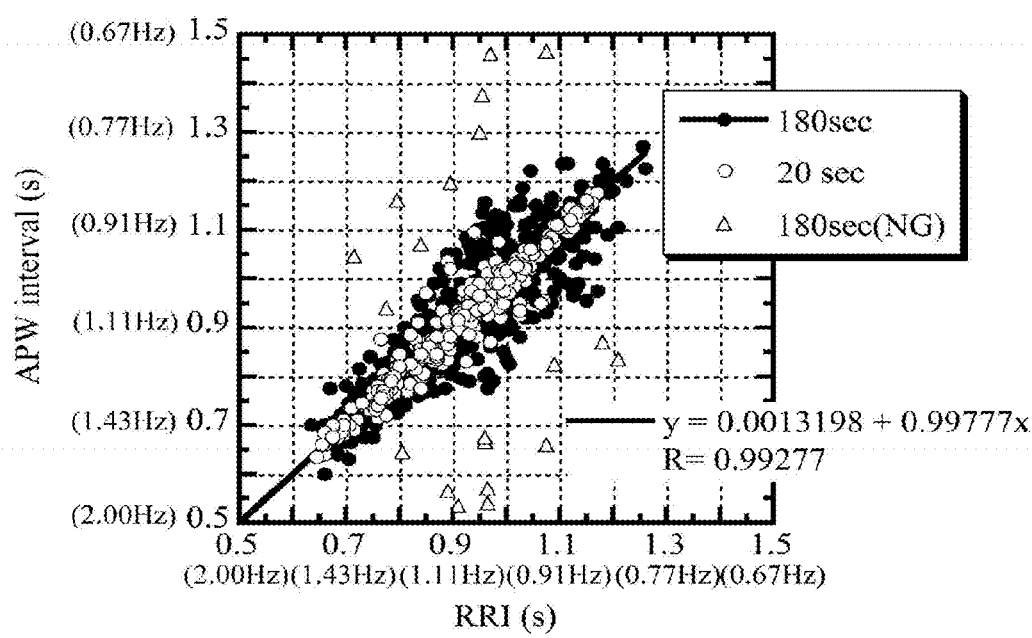
FIG. 29 is a comparative chart of analysis results of data of all fifteen subjects during a 20 or 180 second analysis time on RRI of an electrocardiogram and an interval of APW.

FIG. 29 is a comparative chart of analysis results of data of all the fifteen subjects during a 20 or 180 second analysis time on RRI of the electrocardiogram and the interval of APW. Average values of correlation coefficients for the 20 second or 180 second measurement time in the data of the fifteen subjects were $R_{20}=0.9$, $p_{20}=0.0026$, $R_{180}=0.89$, and $p_{180}=3.6\times10^{-39}$. An S/N ratio obtained under the environment of this experiment was 19 dB.

When the subjects are healthy and in the resting supine state, the number of data having no correlation between RRI and the interval of APW is as in the group of data indicated by the "outline triangles" in the drawing, one to two strokes of such data occurring per person during 180 seconds. When the correlation coefficient was found in the data exclusive of the group, the result was $R_{180}=0.99$. Hence, it is thought that the 20 second measurement time ensures reliability. Further, BMI values of the fifteen subjects were within a range from 19.0 to 27.5, and APW and RRI of the subjects in this range had a significant correlation. That is, it has been found out that APW, when measured in the resting supine state where a stress by the measurement is not likely to be felt, can have an interval characteristic close to that of RRI of the electrocardiogram, and enables to quickly obtain the information on the cardiac cycle by the 20 second measurement.

From the above experiment results, it follows that the sound and vibration information with around 25 to 50 Hz emanating from the cardio-vascular system can be obtained as the sound and vibration information whose center frequency is around 20 Hz, from the back of the trunk, as a result of passing through the esophagus, pulmonary artery, muscle of the trunk, bones, skin, and clothes, and by using the sound and vibration information collecting mechanism 10 using the natural oscillators 122 whose natural frequency is set so as to correspond to the center frequency of the sound and vibration information, and by using the sound and vibration information sensing system 1 including this sound and vibration information collecting mechanism 10 and the arithmetic means 20 whose pass band width for the filtering includes around 20 Hz being the center frequency, it is possible to accurately capture the cardiac cycle information represented by the first and second heart sounds, and to accurately capture the information regarding the autonomic nervous function, such as APW which has the low-frequency vibration waveform with around 1 Hz. Further, under the dynamic environment where the external vibration is inputted, the amplitude of the natural oscillators increases due to the external vibration, resulting in an increase of the amplitude of the composite wave of the sound and vibration information of the cardio-vascular system and the vibration of the natural oscillators. Accordingly, this composite wave has high toughness against noise, enabling to capture the accurate cardiac cycle information even under the dynamic environment. Therefore, APW obtained by the present invention serves as a substitute index for the interval characteristics of the electrocardiogram and the phonocardiogram and can be said as being suitable for the measurement in the unconstrained state while the vehicle is traveling and in particular, as being useful for analyzing a biological state of the driver of the vehicle during the driving. Further, in the present invention, weak sound and vibration information of the cardio-vascular system, which normally cannot be collected unless a doctor brings a stethoscope into direct contact with the body surface at a position near the heart at the time of medical checkup in a hospital or the like, can be captured as the resonance carrier (RC) and APW from the back side of a person in a non-invasive and unconstrained state while the person is supported on bedding such as a bed and a chair such as an automobile seat.

C. Experiment at the Time of the Sitting Posture Under a Dynamic Environment Having a Different Condition For comparison with the above-described "experiments at the time of the sitting posture under the static and dynamic environments (active state)", an experiment in which an excitation condition of the vibrator under the dynamic environment was changed from the above was conducted. Specifically, driving on a freeway in Michigan State, USA, was simulated. An excitation waveform with a high vibration acceleration level generated from impact vibration was reproduced by the vibrator. FIG. 30 are comparative charts of results of the experiments under the static environment and the two dynamic environments, and in all of FIGS. 30(*a*) to (*d*), the left graphs illustrate the results of the experiments under the static environment (Static), the middle graphs illustrate the results of the experiments at the time of the excitation with the up-down direction acceleration waveform which is generated in the floor being the seat attachment part of the standard-sized car when the car travels on the Sanyo Expressway at 80 to 100 km/h (State 1), and the right graphs illustrate the results of the experiments at the time of the excitation with the waveform when the driving on the freeway in Michigan State, USA is simulated (State 2).

Further, FIG. 30(*a*) illustrates accelerations acting on an attachment surface of the seat back part in response to the up-down vibration input, and FIG. 30(*b*) illustrates sound waveforms originating in the accelerations on the attachment surface of the seat back part which waveforms are inputted to the microphone sensor. FIG. 30(*c*) illustrates waveforms Generated as a result of the combination of the sound and vibration information of the cardio-vascular system of the subject with the waveforms in FIG. 30(*b*), that is, illustrates waveforms of the resonance carriers (RC1) generated as a result of the filtering processing with the 10 to 30 Hz frequency band by the filtering means 210 of the arithmetic means 20, and (d) illustrates waveform data of APWs that the state analyzing means 220 outputs after subjecting the waveforms in (c) to the detection.

From FIG. 30, it is seen that the composite waveform of the 20 to 30 Hz power spectrum of the external vibration input and the sound and vibration information of the cardio-vascular system, and APW generated as a result of the processing of the composite waveform capture the cardiac cycle characteristic, and the power spectrum of the external vibration is superimposed on APW, so that the amplified output can be obtained. Thus, it is seen also from FIG. 30 that the composite wave of the sound and vibration information of the cardio-vascular system and the vibration of the natural oscillators has a high robustness against disturbance. Further, when the 20 to 30 Hz external vibration with the high vibration acceleration level of State 2 was taken, the interval characteristic of APW could be captured with a larger amplitude than when the external vibration with the low vibration acceleration level of the State 1 was taken.

Figure 31:
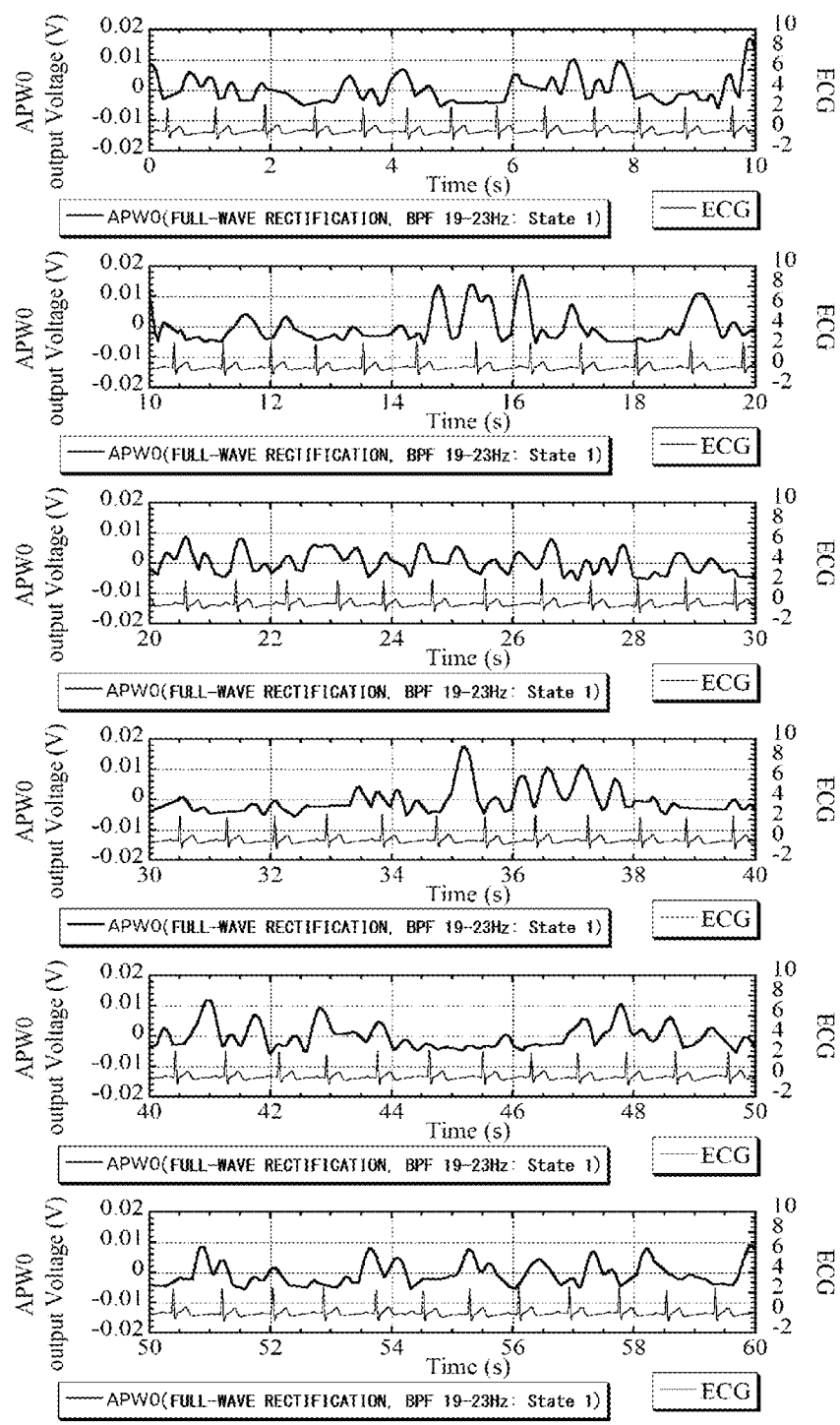
FIG. 31 are charts illustrating examples of a time series waveform of APW that a state analyzing means finds by using a resonance carrier RC2 generated as a result of filtering by a 19 to 23 Hz band pass filter in a filtering means.
Figure 32:
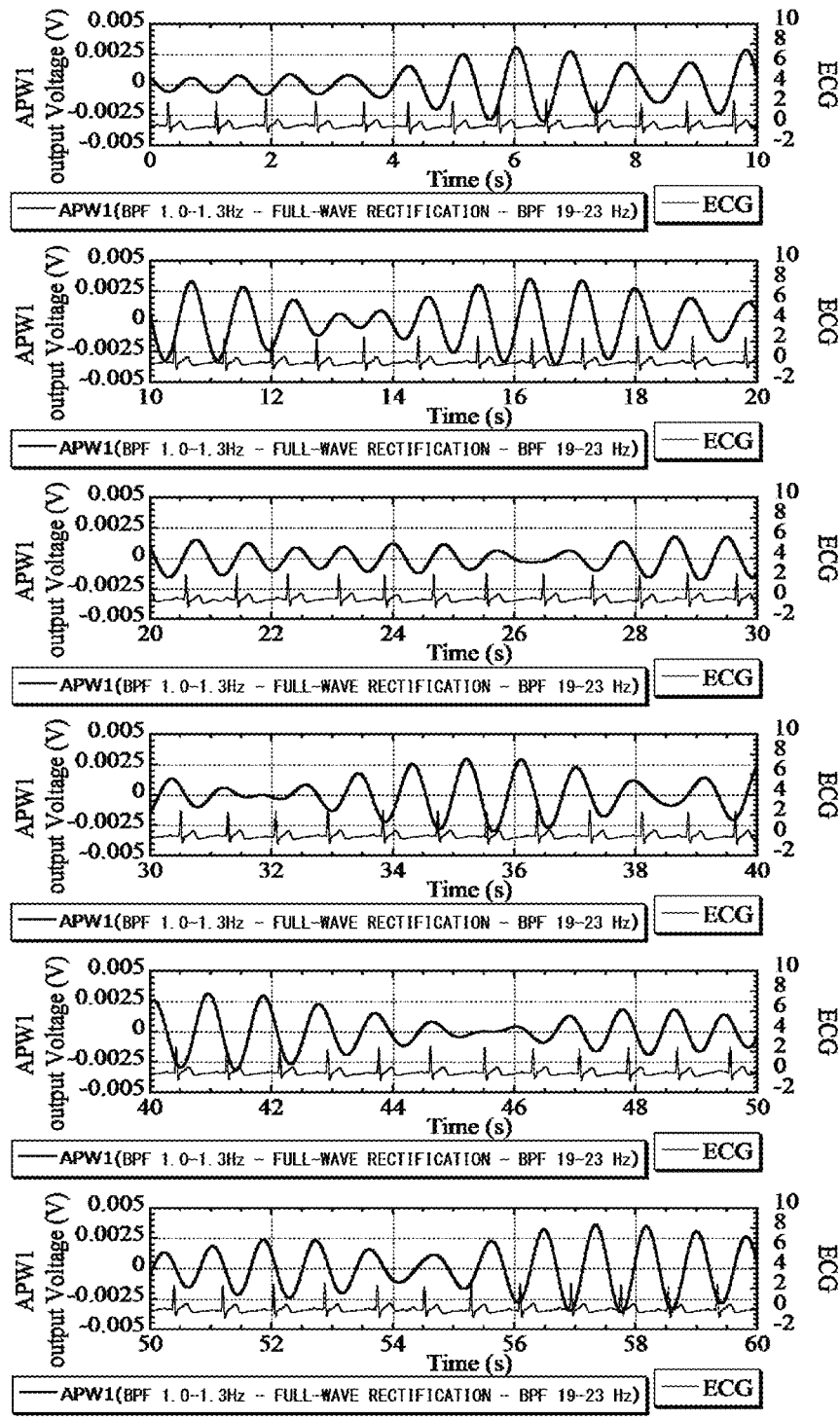
FIG. 32 are charts illustrating time series waveforms generated as a result of further filtering of the time series waveforms of APW found in FIG. 31 by a 1.0 to 1.30 Hz band pass filter.

Here, FIG. 31 illustrate examples of a time series waveform of APW ("APW0") that the state analyzing means 220 finds by using the resonance carrier RC2 generated as a result of the filtering by the 19 to 23 Hz band pass filter in the filtering means 210. FIG. 32 illustrate time series waveforms ("APW1") generated as a result of the further filtering of the time series waveforms of APW0 by a 1.0 to 1.30 Hz band pass filter. The cutoff frequency of the band pass filter is not limited to this, and can be, for example, 1.17 to 1.30 Hz. In any case, APW1 generated as a result of the filtering of APW0 by the band pass filter with a 0.1 to 1 Hz pass band width has a waveform reflecting the cardiac cycle information more accurately. That is, the state analyzing means 220 is preferably structured to have such a means for finding APW1 by filtering APW0 by the band pass filter with the 0.1 to 1 Hz pass band width after APW0 is found from the resonance carrier.

The sound and vibration information collecting mechanism of the present invention, when used, can be assembled in an area corresponding to the back of a person on bedding (bed, futon, or the like) or a seat (vehicle seat, office chair, massage chair, sofa, or the like) which is the body support means. The body support means can also be provided in a state where the sound and vibration information collecting mechanism has been assembled therein.

Figure 2:
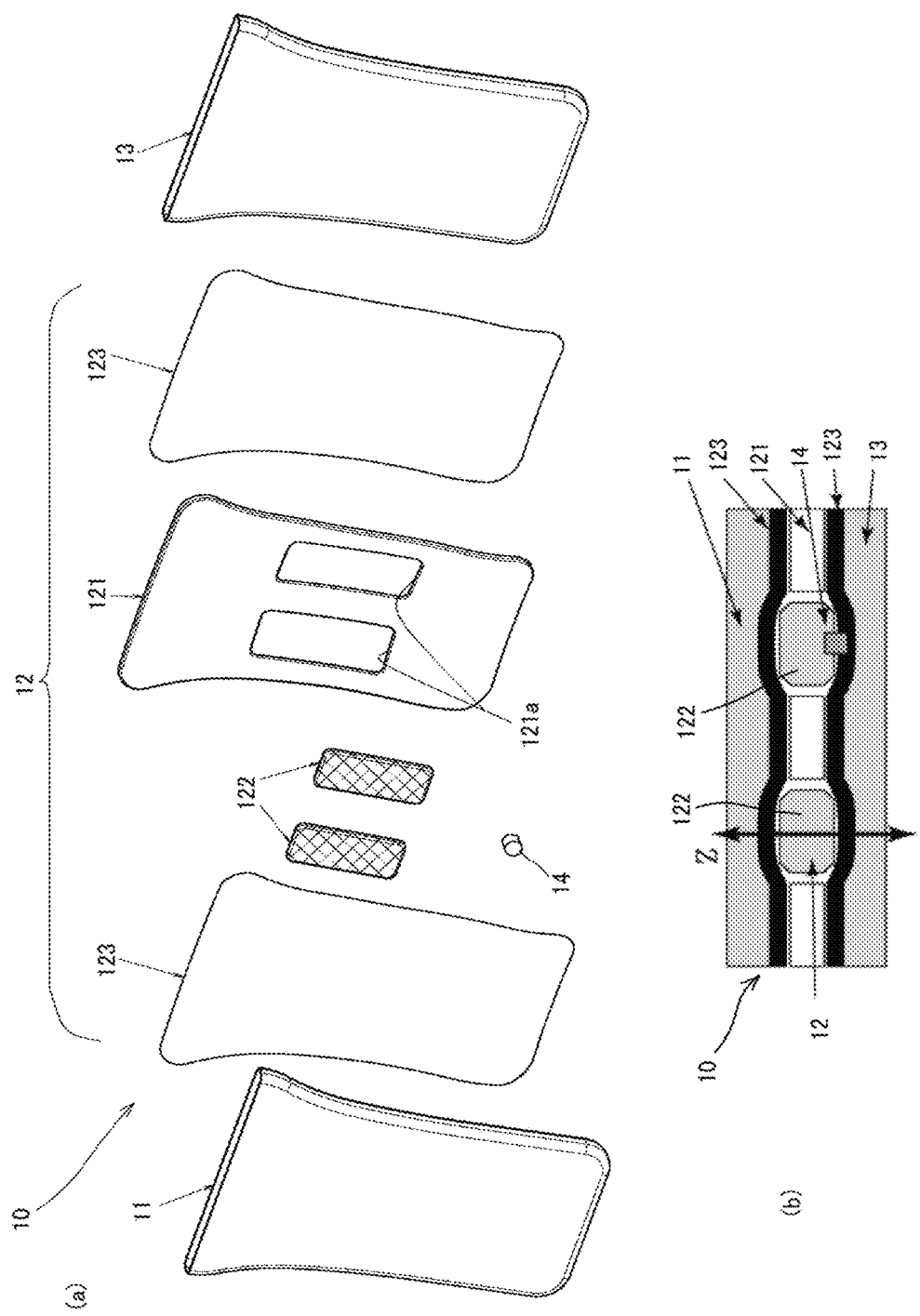
FIG. 2(a) is an explanatory perspective view of the structure of a sound and vibration information collecting mechanism.
FIG. 2(b) is a cross-sectional view thereof.
Figure 33:
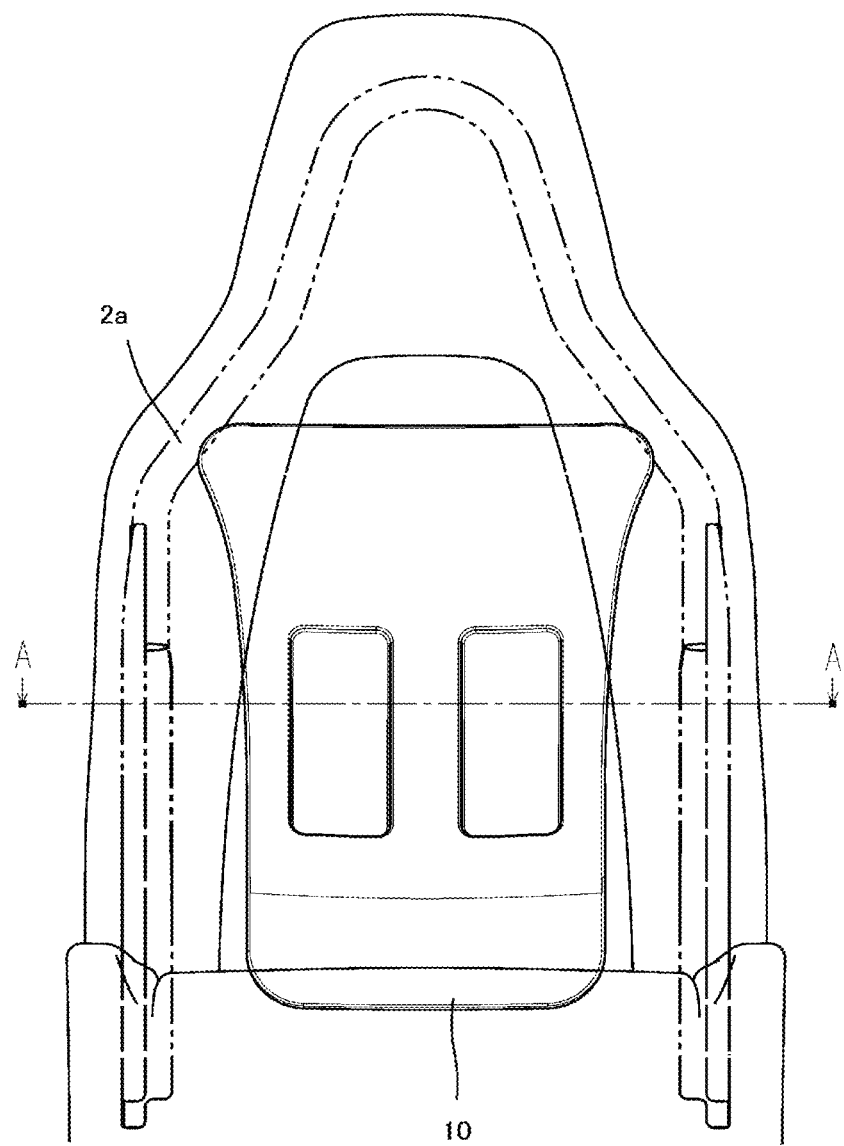
FIG. 33 is a schematic front view illustrating a state where the sound and vibration information collecting mechanism is assembled in an automobile seat.
Figure 34:
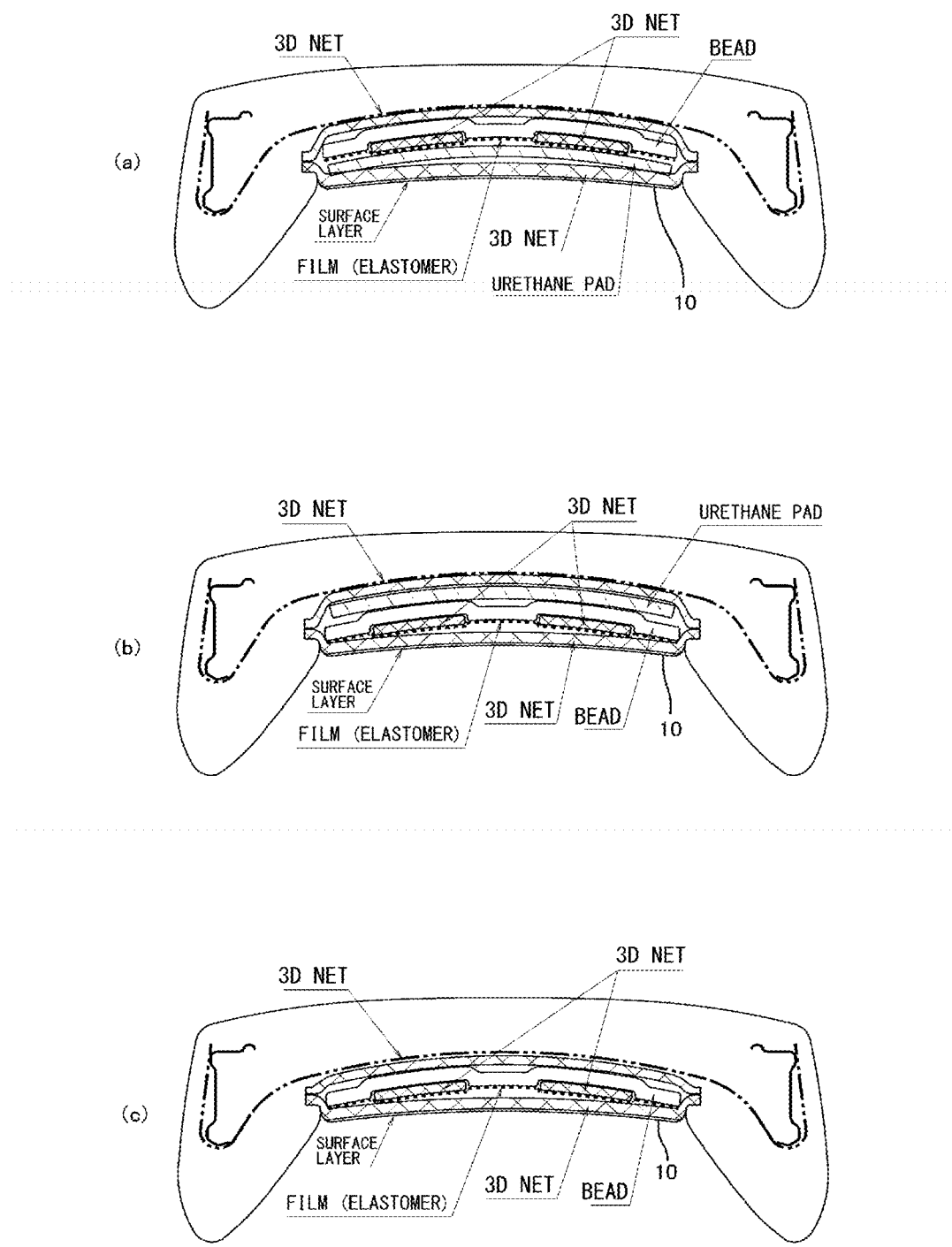
FIGS. 34(a) to (c) are views illustrating variations of the sound and vibration information collecting mechanism.
Figure 35:
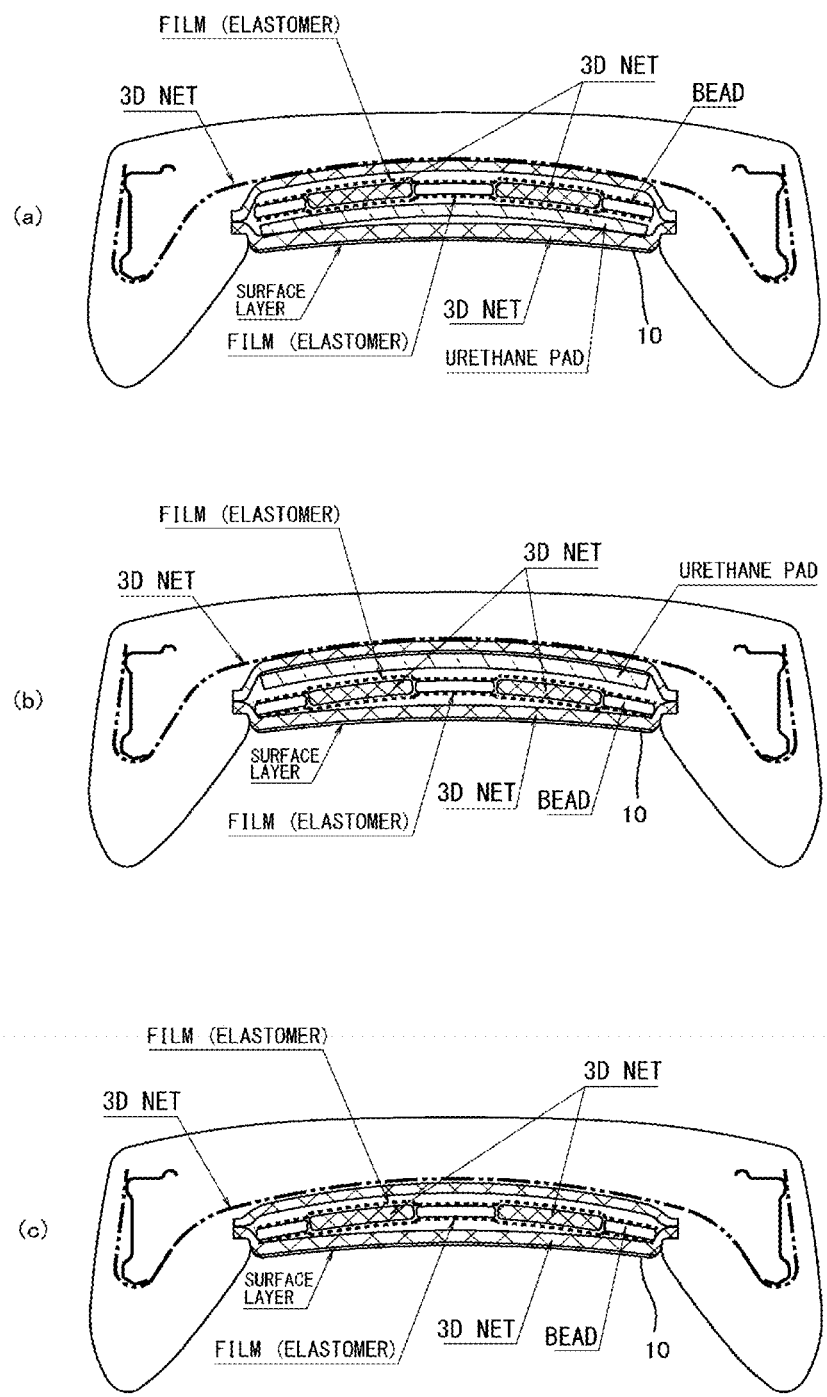
FIGS. 35(a) to (c) are views illustrating variations of the sound and vibration information collecting mechanism.

In the above description, in the sound and vibration information collecting mechanism 10, the natural oscillators 122, 122 are disposed in the casing 121 of the second layer 12, the films 123, 123 are stacked on the natural oscillators 122, 122, and on the outer sides thereof, the first layer 11 and the third layer 13 each formed of the three-dimensional knitted fabric are stacked respectively (refer to FIG. 1 and FIG. 2). The sound and vibration information collecting mechanism 10, however, can be variously modified within a range not impairing its functions described above. For example, a bead foam may be stacked or a urethane pad may be stacked on the second layer 12 as illustrated in FIGS. 34(a) to (c) and FIGS. 35(a) to (c). Note that FIG. 34 and FIG. 35 are sectional views corresponding to the A-A line in FIG. 33. Specifically, FIG. 34(a) illustrates an example where a urethane pad is stacked and disposed between a second layer, which includes: a bead foam (denoted as "bead" in the drawing) forming a casing; three-dimensional knitted fabrics (denoted as "3D net" in the drawing) forming natural oscillators; and a film (denoted as "film (elastomer)" in the drawing) covering the three-dimensional knitted fabrics, and a first layer formed of a three-dimensional knitted fabric (denoted as "3D net" in the drawing) and disposed on a person's body side. FIG. 34(b) illustrates an example where a urethane pad is stacked and disposed between a second layer and a third layer formed of a three-dimensional knitted fabric (denoted as "3D net" in the drawing), and FIG. 34(c) illustrates an example where a urethane pad is not disposed. Note that the bead foam used in FIGS. 34(a) to (c) has a shape in which its portions where to insert three-dimensional knitted fabrics forming natural oscillators are not the through holes (arrangement holes 121a) illustrated in FIG. 2 but are formed in a groove shape, and its rear portions corresponding to these portions project rearward.

In each of FIGS. 35(a) to (c), in a bead foam (denoted as "bead" in the drawings), its portions where to insert three-dimensional knitted fabrics (denoted as "3D net" in the drawings) forming natural oscillators are formed as the same through holes as those (arrangement through holes 121a) illustrated in FIG. 2, and films (denoted as "film (elastomer)" in the drawings) are provided on both surfaces of the bead foam. FIG. 35(a) illustrates an example where a urethane pad is disposed between a second layer and a first layer. FIG. 35(b) illustrates an example where a urethane pad is disposed between a second layer and a third layer. FIG. 35(c) illustrates an example where a urethane pad is not disposed, which is substantially the same structure as that illustrated in FIG. 2. Note that, in any of the forms illustrated in FIG. 2, FIG. 34, and FIG. 35, the film covering the three-dimensional knitted fabrics forming the natural oscillators can also be formed of the film formed on the surfaces of the bead foam.

Figure 36:
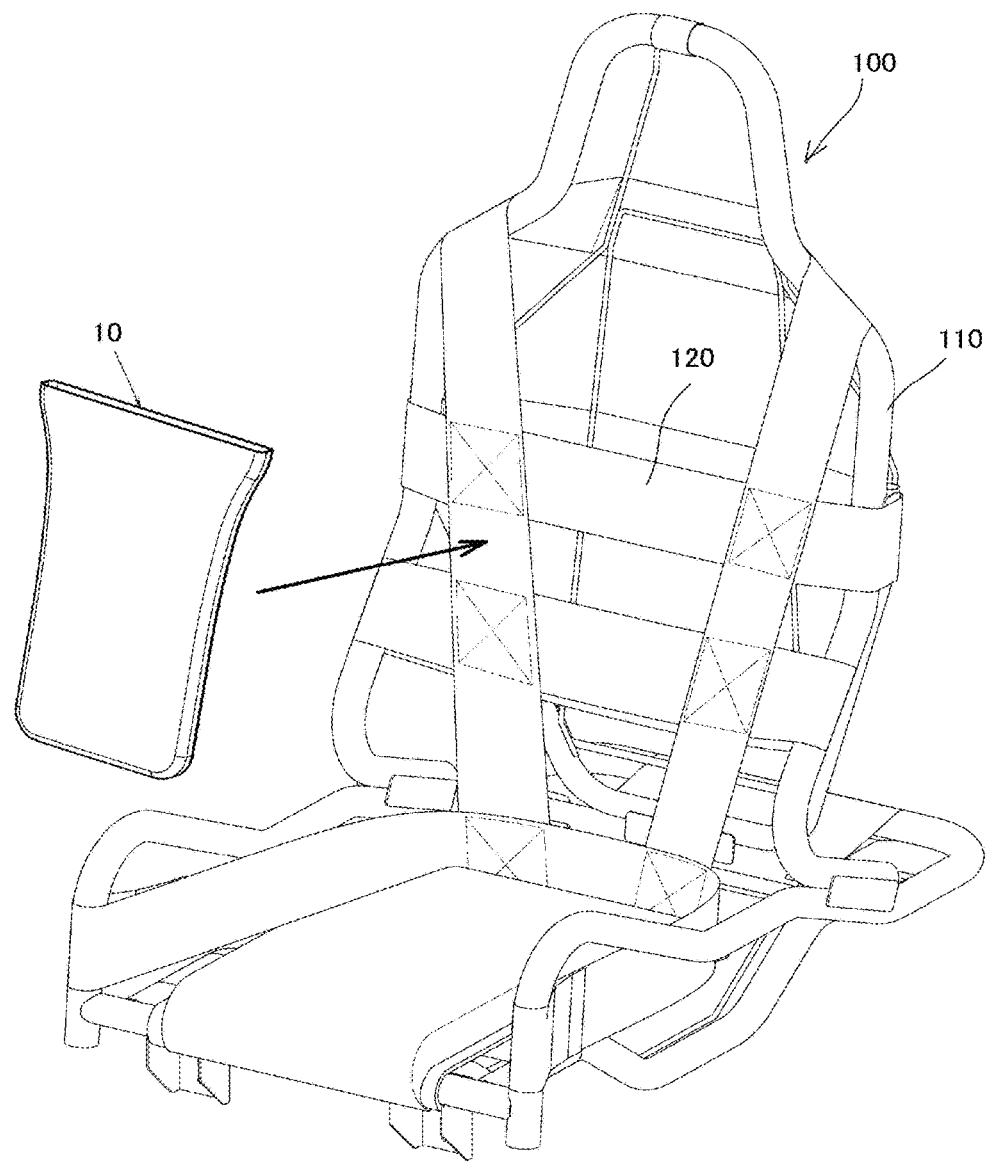
FIG. 36 is a view illustrating an example of a seat in which the sound and vibration information collecting mechanism is suitably assembled.

It is also possible to dispose the sound and vibration information collecting mechanism 10 on a metal spring such as a coil spring or an S spring in the body support means, but an example of another possible structure is that, as illustrated in FIG. 36, a belt-shaped support member 120 formed of woven polyester fibers used in automobile seat belts is disposed on a seat back frame 110 forming the seat back part 100, and this belt-shaped support member 120 supports the sound and vibration information collecting mechanism 10. Another possible structure is that a three-dimensional knitted fabric instead of this belt-shaped support member 120 is stretched on the seat back frame 110 and the three-dimensional knitted fabric supports the sound and vibration information collecting mechanism 10, or a three-dimensional knitted fabric is stacked on the surface of the belt-shaped support member 120 to support the sound and vibration information collecting mechanism 10.

Such support layers of the sound and vibration information collecting mechanism 10, such as the metal spring, the belt-shaped support member, and the three-dimensional knitted fabric each have a function of damping sound and vibration inputted from the outside. By the spring constants being adjusted, these support layers can have a function of cutting off high-frequency vibration with 100 Hz or higher, preferably 40 Hz or higher which causes the biosignal to be buried. Accordingly, in the case where the body support mechanism where to dispose the sound and vibration information collecting mechanism 10 includes such a support layer, the sound and vibration information collecting mechanism 10 can be structured not to have the third layer 13 which damps the high-frequency external vibration.

Hereinafter, various analysis cases using the sound and vibration information collecting mechanism and the sound and vibration information sensing system of the present invention will be described.

Analysis Case 1

(Analysis Regarding the Detection of APW Using a Resonance Carrier at the Time of a Supine State, and a Correlation of APW with Heart Sound)

Regarding thirteen healthy male subjects in their twenties to thirties, measurement was conducted for fifteen minutes while they were supine. The sound and vibration information collecting mechanism 10 was made to abut on the back, and as a comparative index, heart sound was measured from the chest of each of the subjects. A heart sound sensor and a heart sound/pulse wave amplifier are TA-701T and AS-101D manufactured by Nihon Kohden Corporation.

Figure 37:
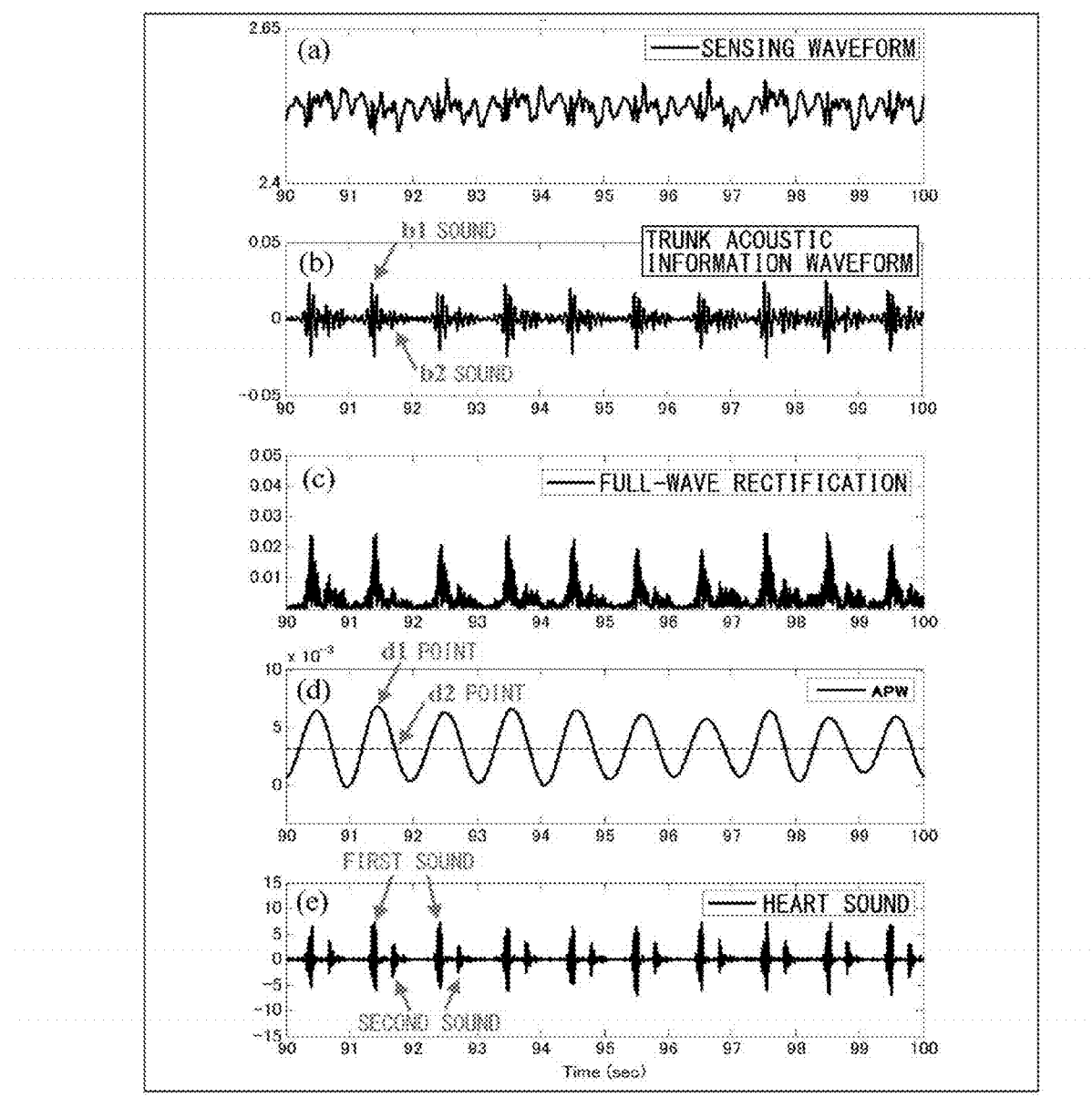
FIG. 37 are charts illustrating waveforms from a sensing waveform to an APW waveform in an analysis case 1.

FIG. 37 illustrate measurement results, (a) illustrating a sensing waveform of the microphone sensor 14, (b) illustrating data of a resonance carrier RC1 generated as a result of the filtering by the 10 to 30 Hz band pass filter forming the filtering means 210, (c) illustrating a waveform generated as a result of full rectification, and (d) illustrating a waveform of APW outputted from the state analyzing means 220. (e) illustrates a waveform of a phonocardiograph.

The waveforms indicated by the arrows in the phonocardiogram in FIG. 37(e) represent the first sound and the second sound. The first sound and the second sound are synchronous with b1 sound and b2 sound of the output data of RC1 in FIG. 37(b). Similarly, the first sound and the second sound are synchronous with a d1 point and a d2 point (direct-current components) of the waveform of APW in FIG. 37(d).

Figure 38:
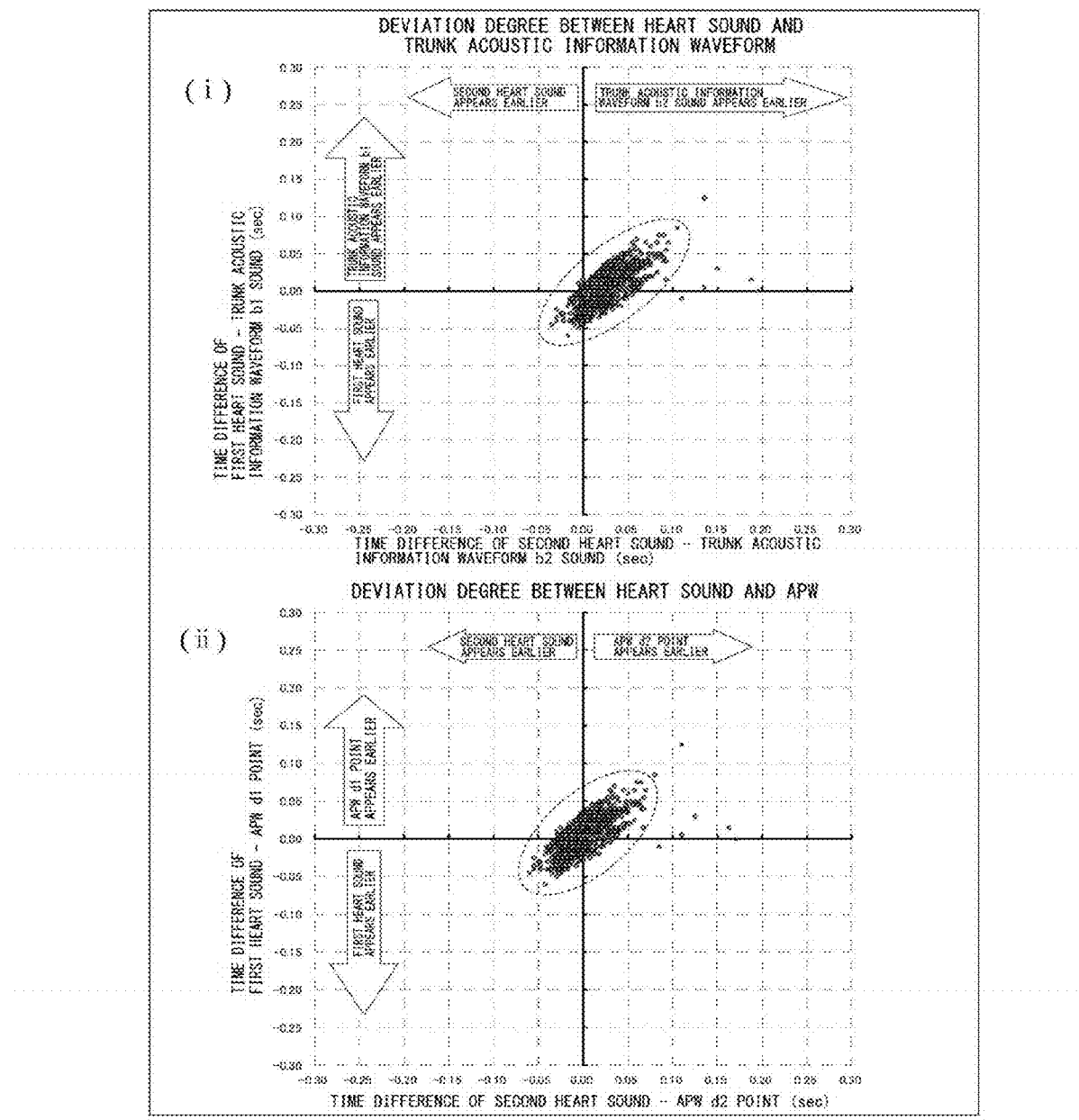
FIG. 38 are charts illustrating deviation distribution from a phonocardiogram in the analysis case 1.

FIG. 38(i) is a chart illustrating the distribution of lag time of the b1 sound and the b2 sound from the first sound and the second sound in the phonocardiogram, FIG. 38(ii) is a chart illustrating the distribution of lag time of the d1 point and the d2 point from the first sound and the second sound in the phonocardiogram. In both of the drawings, the horizontal axis represents deviation from the second heart sound and the vertical axis represents derivation from the first heart sound.

Figure 39:
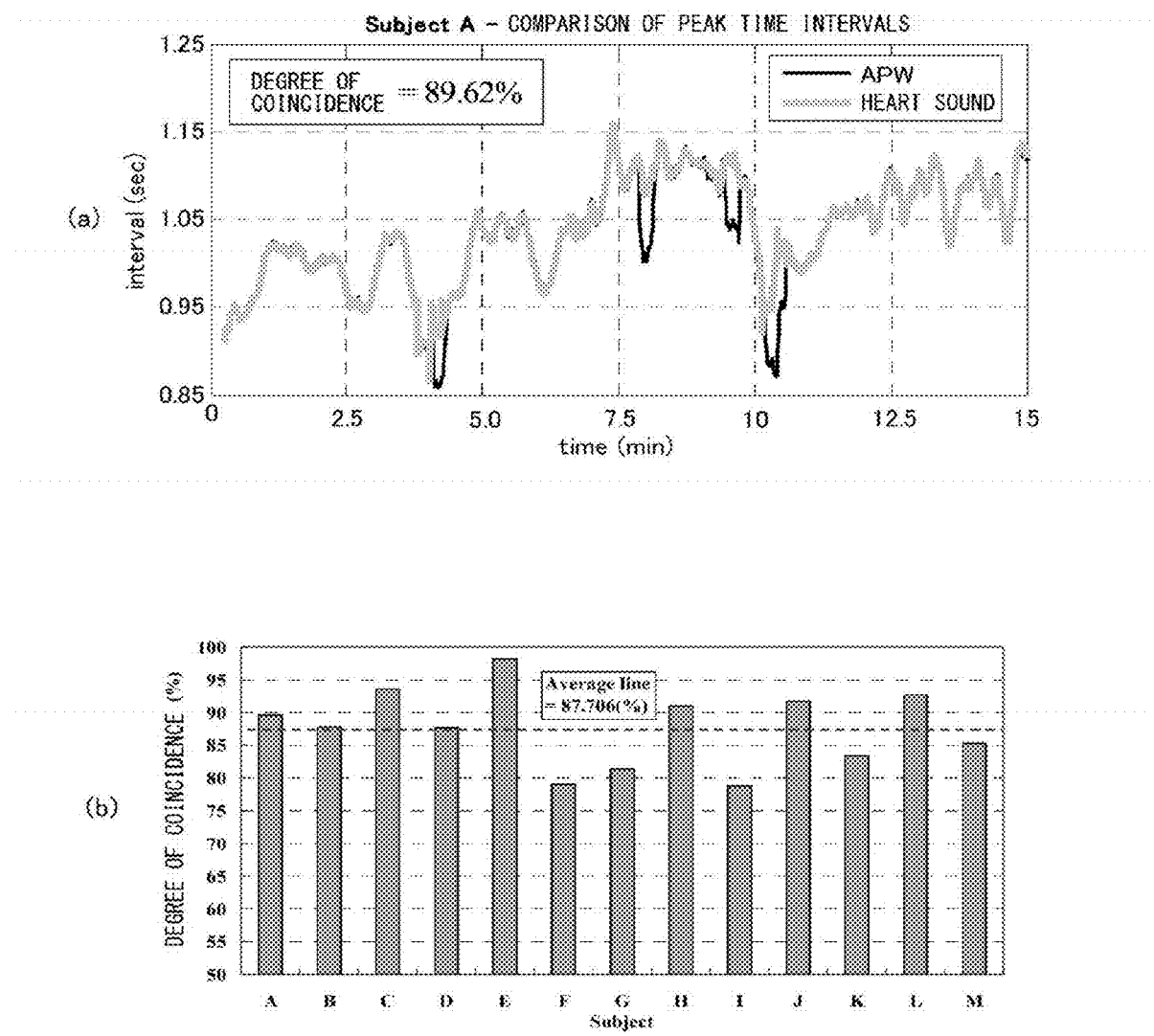
FIG. 39(a) is a comparative chart of peak time intervals of APW and the first heart sound.
FIG. 39(b) is a chart illustrating distribution of a degree of coincidence of the peak time intervals.

FIG. 39(a) illustrates comparison between a peak time interval of APW and a time interval of peak values of the first heart sound of the subject A, the horizontal axis representing the measurement time (minute) and the vertical axis representing the time (second) between the peaks. A degree of coincidence of the peak time interval found using a normalized cross-correlation function expressed by the expression 6 was 89.62%.

FIG. 39(b) is a chart illustrating degrees of coincidence of normalized cross-correlation functions of thirteen subjects. The highest value was 98%, the lowest value was 78.8%, and an average value was 87.7%.

From the above, RC1 generated as a result of the filtering by the 10 to 30 Hz band pass filter forming the filtering means 210 and APW calculated using RC1 had a high degree of coincidence with the first heart sound in terms of their intervals.

[expression 6]

$$R_{zNcc} = \frac{\sum_{j=0}^{N-1}\sum_{i=0}^{M-1}(I(i,j)-\bar{I})(T(i,j)-\bar{T})}{\sqrt{\sum_{j=0}^{N-1}\sum_{i=0}^{M-1}(I(i,j)-\bar{I})^2 \times \sum_{j=0}^{N-1}\sum_{i=0}^{M-1}(T(i,j)-\bar{T})^2}} \quad (6)$$

(I (i,j)=inter-peak time of APW, T (i,j)=inter-peak time of the first heart sound)

Analysis Case 2

(Analysis Case Using a Resonance Carrier, Regarding a Nearly Missed Accident)

First, regarding seventeen male subjects in their twenties to thirties, while they are in a resting supine state, a waveform of APW was found from data of a resonance carrier RC1 generated as a result of the filtering by the 10 to 30 Hz band pass filter forming the filtering means 210 as in the analysis case 1, and a correlation of this with an R-R interval (hereinafter, "RRI") calculated from an electrocardiogram (BSM-2301 manufactured by Nihon Kohden Corporation) was checked.

Figure 40:
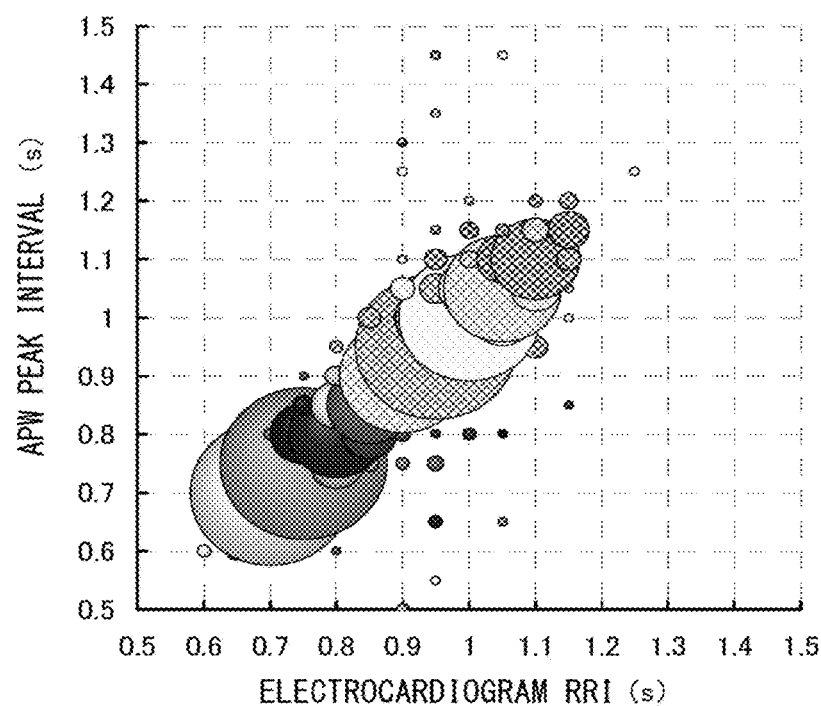
FIG. 40 is a chart illustrating comparison between an APW peak point interval and an electrocardiogram in an analysis case 2.

FIG. 40 illustrates comparison results on the seventeen subjects, the vertical axis representing an interval between peak points of APW and the horizontal axis representing RRI. Note that the size of each plot point indicates a degree. Then, a correlation function regarding a relation between the interval of the peak points of APW and RRI was calculated for each of the subjects, and the result was: correlation coefficient r=0.874±0.075 (Mean±SD). Further, when the correlation was examined for each of the subjects, the result was p<0.05 in all the subjects; therefore it can be said that the both have a correlation.

Next, the sound and vibration information collecting mechanism 10 was installed on an automobile seat, and a driving experiment regarding a nearly missed accident was conducted. Subjects are six healthy males in their thirties to fifties. Incidentally, in order to record the history of the occurrence time of a nearly missed state, Sleep Buster (registered trademark) manufactured by DELTA TOOLING Co., Ltd. was installed on an instrument panel beside a steering wheel. The driver was prohibited from gazing at Sleep Buster (registered trademark) during the driving.

The analysis was conducted on 22 cases where a nearly missed accident occurred. An analysis target range was up to the time when the nearly missed accident occurred. Sound information collected from the sound and vibration information collecting mechanism 10 was signal-processed to be converted to APW. By using peak points of APW or its down-cross points with a base line, each pulse rate was found to be converted to a frequency, and its change degree during three minutes was calculated with 90% lap, that is, every eighteen seconds, and a time series waveform was calculated (hereinafter, the waveform found using the peak points will be called a peak gradient time series waveform, and the waveform found using the down-cross points will be called a zero-cross gradient time series waveform). Next, amplitudes of the zero-cross/peak gradient time series waveforms in the state where the nearly missed accident occurred and the state before this were calculated, and an occurrence probability of the nearly missed accident based on a variable ratio of the amplitudes before and after the nearly missed accident was calculated using Bayes estimation. To calculate the variable ratio, the method of Fujita et. al. using a finger plethysmogram (FUJITA Etsunori et. al.: Development of Measurement Method of Prediction of Sleep by Finger Plethysmogram Data", The Japanese Journal of Ergonomics, Vol. 41, No. 4, 203-212, 2005) was used. The following expression 7 is used in the calculation by the Bayes estimation. Note that H2: nearly missed accident state, H1: wakeful state, and D: target data. Further, "H2: nearly missed accident state" was defined as a "fifteen-minute period immediately before the occurrence of the nearly missed accident state".

[expression 7]

$$P(H_2 | D) = \frac{P(D|H_2)P(H_2)}{P(D|H_1)P(H_1) + P(D|H_2)P(H_2)} \quad (7)$$

Figure 41:
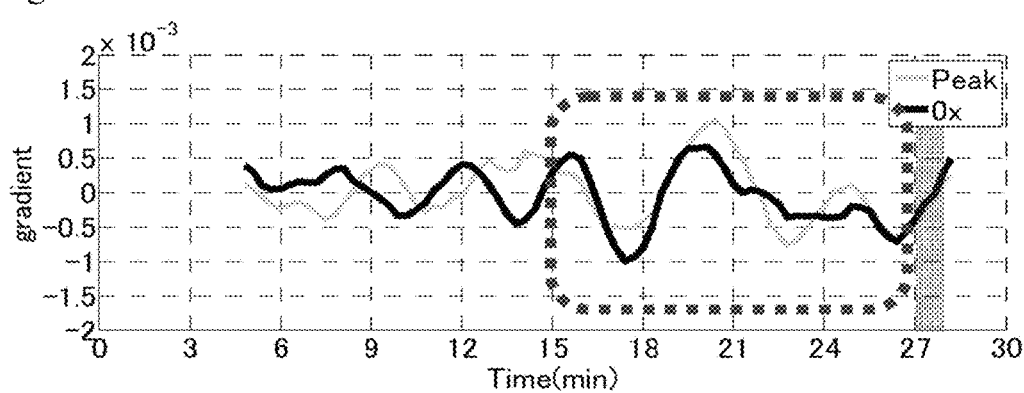
FIG. 41 is a chart illustrating data regarding a typical case when a nearly missed accident occurs, in the analysis case 2.

FIG. 41 illustrates typical examples of the zero-cross gradient time series waveform and the peak gradient time series waveform during a thirty minute period including the time when the nearly missed accident occurs. Note that the hatched part is when the nearly missed accident occurred, and this example is a case where the subject declared that he slept momentarily during this part. In this example, it is seen that, from twelve minutes prior to the occurrence of the nearly missed accident to one minute prior to the occurrence, the amplitude of the zero-cross gradient time series waveform reduces and the amplitude of the peak gradient time series waveform becomes larger than that in the former half. It is indicated that a waveform generated as a result of absolute value processing of the zero-cross gradient time series waveform is close to a change of LF/HF which is said to be an index of sympathetic nerve activity, and a waveform generated as a result of absolute value processing of the peak gradient time series waveform is close to a change of HF which is said to be an index of parasympathetic nerve activity (MAEDA Shinichiro et. al.: "Development of State Estimation Technology for Driver by Sensor of Unconstrained Type", Proceedings from the 11th Symposium on "Motion and Vibration Control" of The Japan Society of Mechanical Engineers, No. 09-30, 2009).

The above indicates a possibility that, during several minutes immediately before the nearly missed accident, the sympathetic nerve activity degenerated and the parasympathetic nerve activity was activated in the driver, and there was no fluctuation causing a change of the state, and thus the driver was in a state where he could not resist sleepiness. When the attenuating and strengthening tendencies of the gradient time series waveforms immediately before the occurrence of the nearly missed accident were studied in the 22 cases where the nearly missed accident occurred, the results were as follows.

(1) Case where the Peak Gradient Time Series Waveform Presents the Tendency of "Strengthening or No Change"

The zero-cross gradient time series waveform presents the tendency of "attenuation": 18 cases The zero-cross gradient time series waveform presents "strengthening or no change": one case (2) Case where the Peak Gradient Time Series Waveform Presents the Tendency of "Attenuation"

The zero-cross gradient time series waveform presents the tendency of "attenuation": three cases The zero-cross gradient time series waveform presents "strengthening or no change": 0

Figure 42:
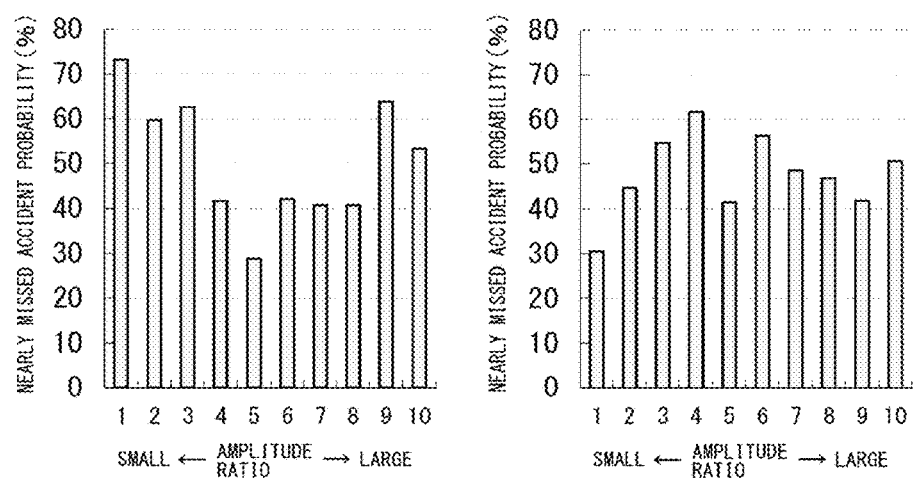
FIG. 42 is a chart illustrating occurrence probabilities of a nearly missed accident based on Bayes estimation, in the analysis case 2.
Figure 43:
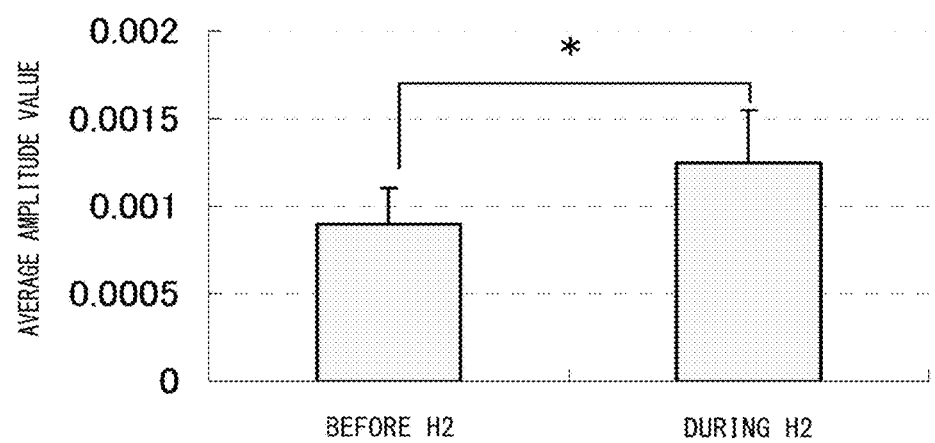
FIG. 43 is a chart illustrating comparison of average amplitude values of a peak gradient time series waveform.

Next, the occurrence probability was found, using the Bayes estimation. FIG. 42 illustrate the occurrence probability of the nearly missed accident which was found with amplitude variation ratios of both the zero-cross (left drawing) and peak (right drawing) gradient time series waveforms being used as parameters. The amplitude variation ratio that is large in an increasing direction is defined as 10 and the amplitude variation ratio that is large in a decreasing direction is defined as 1. From the left drawing in FIG. 42, it has been found out that the occurrence probability of the nearly missed accident is high when a change occurs so that the amplitude variation of the zero-cross gradient time series waveform rapidly increases or rapidly decreases. From the right drawing in FIG. 42, it has been found out that the occurrence probability of the nearly missed accident is high when the variation ratio of the peak gradient time series waveform is small. This is thought to be because, as is seen from FIG. 43 which is "the drawing in which average amplitude values of the peak gradient time series waveform before the nearly missed accident state (before H2) and during the nearly missed accident state (during H2) are compared", the amplitude during H2 (during the nearly missed accident state=during "fifteen minutes immediately before the occurrence of the nearly missed accident") is larger than the amplitude before H2 (before the nearly missed accident state=during a time zone before the fifteen minute period immediately before the nearly missed accident state), and the time zone of H2 is after the amplitude increase has already occurred, and thus the amplitude variation during H2 becomes small. From these points, it can be said that the above-described study results of the attenuating and strengthening tendencies of the gradient time series waveforms immediately before the occurrence of the nearly missed accident are reasonable.

From this analysis case, it is seen that the occurrence probability of the nearly missed accident becomes high when the zero-cross gradient time series waveform of APW using the resonance carrier is rapidly strengthening or rapidly attenuating. Therefore, it is possible to output a detection warning of the nearly missed accident based on the time when the zero-cross gradient time series waveform of APW is rapidly strengthening or rapidly attenuating.

Analysis Case 3

(Analysis Case Regarding a Method of Discriminating the Wakeful State and the Sleep State Using the Resonance Carrier)

Figure 44:
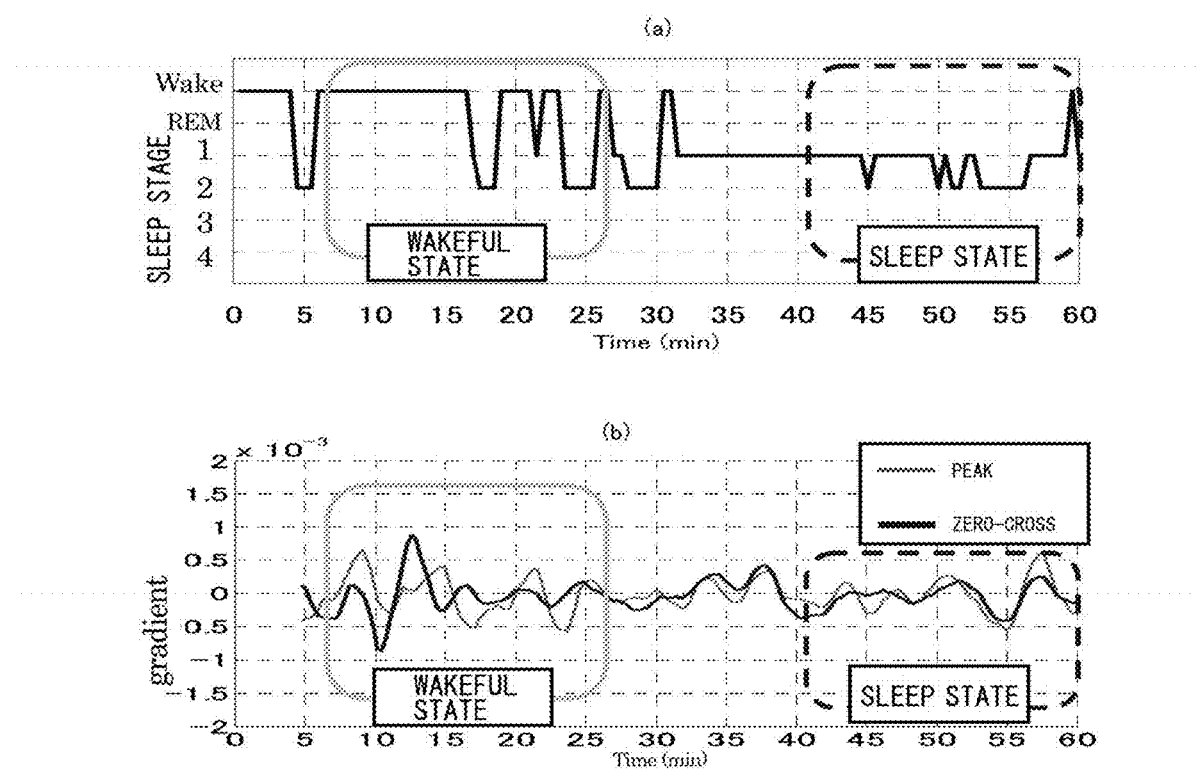
FIG. 44(a) and FIG. 44(b) are charts illustrating a sleep stage and a gradient time series waveform in an analysis case 3, respectively.

In order to measure biosignals in the wakeful state and the sleep state, a sleep experiment was conducted in the resting supine state for one hour. The sound and vibration information collecting mechanism 10 was installed on the back of each subject and the waveform of APW was found from the resonance carrier RC1. At the same time, a brain wave and subjective assessment were measured. The subjects were instructed not to sleep for thirty minutes from the start of the measurement and were instructed that they may sleep after thirty minutes passed. The subjective assessment was conducted during thirty minutes from the start of the measurement to assess a degree of sleepiness every time five minutes passed. The subjects are thirteen healthy males in their twenties to thirties (age 28.31±2.81). Further, based on the sleep stage determination method standardized by Rechtschaffen & Kales, the wakeful stage was defined as 18.9 minutes in which a ratio of the wakeful state is totally 70% and is the largest, and the sleep stage was defined as 18.9 minutes in which a ratio of the first to fourth stages of non-REM sleep is 60% or more and is the largest. Regarding APW obtained from the resonance carrier RC1, pulse rates at zero-cross points and peak points were calculated using the peak detection method and the zero-cross detection method (MAEDA Shinichiro et. al.: "Development of State Estimation Technology for Driver by Sensor of Unconstrained Type", Proceedings from the 11th Symposium on "Motion and Vibration Control" of The Japan Society of Mechanical Engineers, No. 09-30, 2009). Time series waveforms of change degrees of the heart rates during three minutes were calculated as a gradient time series waveform of the zero-cross points and a gradient time series waveform of the peak points respectively. FIG. 44 illustrate the results.

FIG. 44(*a*) illustrates the sleep stage of a male subject in his thirties (hereinafter, "subject A") found by the sleep stage determination method, and FIG. 44(*b*) illustrates the gradient time series waveforms of the zero-cross points and the peak points based on APW obtained from the resonance carrier RC1 of the subject A.

The subjective assessment of the subject A indicates that he was wakeful up to 25 minutes from the start of the measurement and was sleeping all through a period after thirty minutes from the start of the measurement. From FIG. 44(*a*), it is seen that the wakeful state continues for the first half thirty minutes, and a state of REM sleep and the first stage to the second stage of non-REM sleep continues during the latter half thirty minutes. Accordingly, based on the aforesaid definition of the wakeful state and the sleep state, it was determined that the state during 7.2 to 26.1 minutes was the wakeful state and the state during 41.1 to 60 minutes was the sleep state. As for changes of the amplitudes of the gradient time series waveform of the zero-cross point in the time zones of the wakeful state and the sleep state in FIG. 44(b), the amplitude once increased and thereafter decreased in the wakeful state. In the sleep state, the amplitude gradually increased, but it is recognized that the length of the interval has the same tendency as that in the wakeful state. From the above, it has been found out that large and small amplitudes are mixed and long and short intervals are mixed both in the wakeful state and the sleep state.

Figure 45:
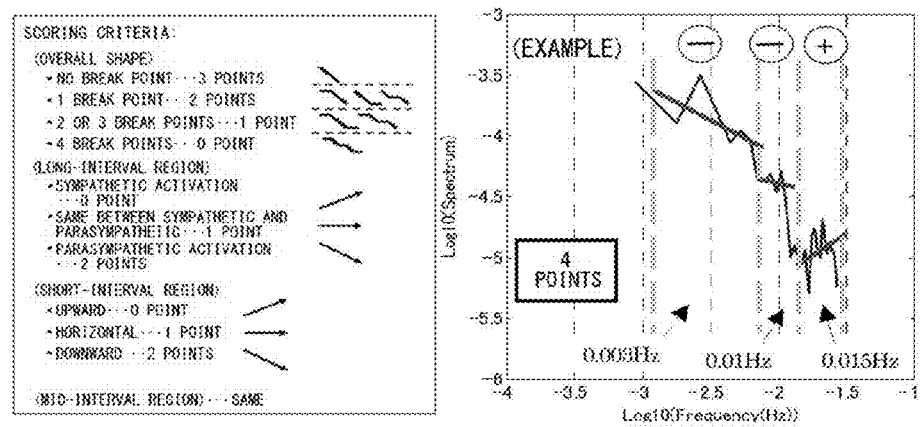
FIG. 45 is a chart illustrating an example of APW quantification criteria.

Here, a frequency analysis (fast Fourier transformation, hereinafter referred to as FFT) was conducted on the gradient time series waveform of the zero-cross point in order to discriminate the wakeful state and the sleep state. By using the quantification scoring method (UCHIKAWA Ryuichi et. al.: "Quantification of Ride Comfort by Physiological Index (APW)", Research Presentation Conference of Chugoku Branch of Japan Society for Design Engineering, No. 28 P46-51 2011) on the result of the frequency analysis, it was attempted to discriminate the wakeful state and the sleep state. In this quantification scoring, FFT is applied to a frequency gradient time series waveform, a logarithmically represented waveform is divided into three sections whose centers are 0.003 Hz, 0.01 Hz, and 0.015 Hz and their approximate lines are drawn, and these sections are scored using the quantification criteria illustrated in FIG. 45.

Figure 46:
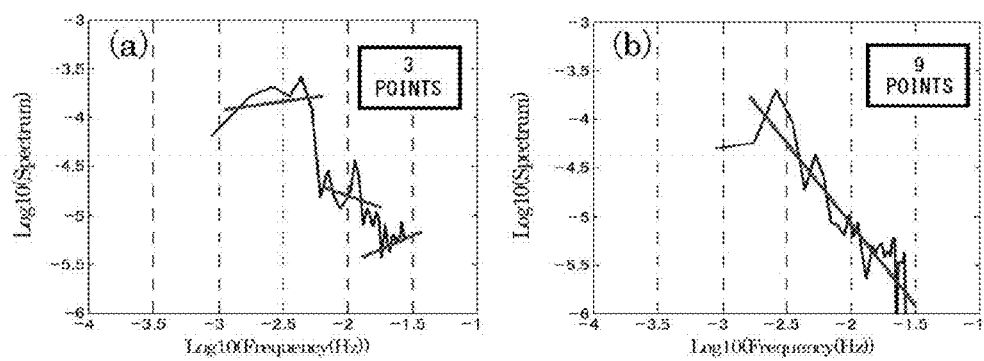
FIG. 46 are charts illustrating frequency analysis results of zero-cross gradient time series waveforms.

FIG. 46 illustrate results obtained when FFT (log-log representation) is conducted on the gradient time series waveforms of the zero-cross points of APW during the time zones of the wakeful state and the sleep state of the subject A, and as a result of the scoring based on the above quantification criteria, the wakeful state scored three points and the sleep state scored nine points. From the above, it is seen that the way the amplitude of the gradient time series waveform of the zero-cross point changes in the wakeful state differs from that in the sleep state, and the use of the quantification scoring method enables the state discrimination.

Figure 47:
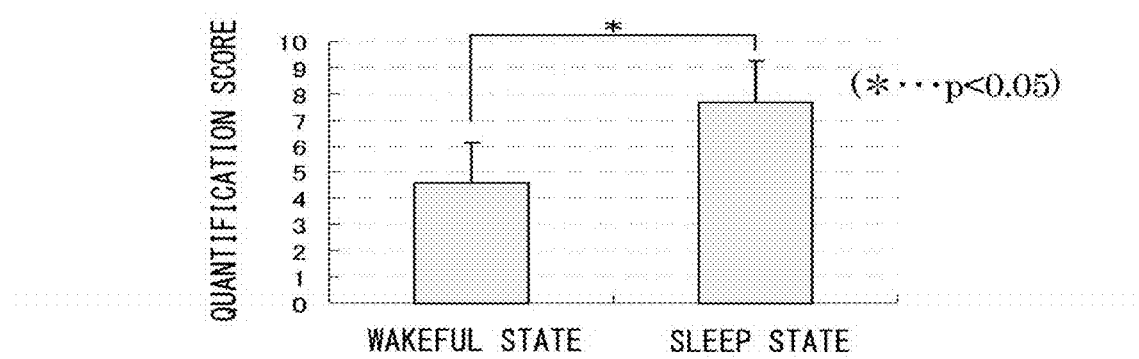
FIG. 47 is a chart illustrating average values and a standard deviation of quantification scores.

FIG. 47 illustrates average values of the quantification scores of the wakeful state and the sleep state of the subjects. When a t-test was conducted on these, the result was $p=2.89 \times 10^{-5}$ and thus $p<0.05$, and there was a significant difference between the quantification scores of the wakeful state and the sleep state.

In the above-described embodiments, the present invention is used for detecting the sound and vibration information from a living body. As is understood from the fact that the present invention is capable of the high-sensitivity collection of the biosignal mainly including the low-frequency sound and vibration information with 100 Hz or lower, it is also advantageous to apply the present invention to detection and analysis of sound and vibration information with a predetermined frequency or lower, for example, several hundred Hz or lower, in particular 200 Hz or lower, and further, 100 Hz or lower in various kinds of machines and devices, for example, low-frequency sound and vibration information such as engine sound of a diesel engine of an automobile. By obtaining and analyzing sound and vibration information of these, it is possible to easily and more accurately determine their states (presence/absence of abnormality). In this case, by disposing the first layer of the sound and vibration information collecting mechanism so as to be in contact with an engine side being a detection target and detecting a resonance carrier from the second layer forming the resonance layer similarly to the above, it is possible to detect the target sound and vibration information. Incidentally, the third layer can be provided as required for the purpose of regulating external vibration.

EXPLANATION OF REFERENCE SIGNS

1 sound and vibration information sensing system
10 sound and vibration information collecting mechanism
11 first layer
12 second layer
121 bead foam
122 three-dimensional knitted fabric
123 film
13 external vibration propagation layer
14 microphone sensor
20 arithmetic means
210 filtering means
220 state analyzing means

The invention claimed is:

1. A sound and vibration information collecting mechanism, which collects low-frequency sound and vibration information with a predetermined frequency or lower from a detection target, the mechanism comprising:
   a resonance layer, which includes a natural oscillator having a natural frequency within a frequency band of the sound and vibration information being a collection target, and generates a resonance carrier by the natural oscillator emphasizing the sound and vibration information;
   a sensor, which detects the resonance carrier,
   wherein the sound and vibration information is a biosignal, the biosignal is sound and vibration information of a cardio-vascular system, and the natural frequency of the natural oscillator is within a frequency band including a frequency of first heart sound or a second heart sound included in the sound and vibration information of the cardio-vascular system;
   a first layer, which is disposed on a back side of a trunk of a living body and to which the sound and vibration information of the cardio-vascular system propagates; and
   a second layer, which includes:
      a casing for resonance having an arrangement space formed as a hole portion or a groove portion where to arrange the natural oscillator and the sensor, and
      a film covering the arrangement space, and which functions as the resonance layer,
   wherein the second layer side is supported by a support layer, which is provided in a body support means to damp externally inputted sound and vibration, and
   wherein a cutoff frequency as a mechanical filter of the second layer is set twice as high as a frequency of the biosignal being the collection target or higher.

2. The sound and vibration information collecting mechanism according to claim 1, comprising:
   another first layer, which is disposed on the detection target side and to which the sound and vibration information propagates; and
   another second layer, which includes:
      a casing for resonance having an arrangement space formed as a hole portion or a groove portion where to arrange the natural oscillator and the sensor; and a film covering the arrangement space, and which functions as the resonance layer.

3. The sound and vibration information collecting mechanism according to claim 1, the mechanism being disposed on the back side of the trunk of the living body and detecting the first heart sound or the second heart sound included in the sound and vibration information of the cardio-vascular system, as sound and vibration information attenuated to a 10 to 40 Hz frequency band.

4. The sound and vibration information collecting mechanism according to claim 1, further comprising a third layer which is disposed opposite to the first layer across the second layer to damp the externally inputted sound and vibration and is provided integrally.

5. The sound and vibration information collecting mechanism according to claim 4, wherein the third layer has a property of damping sound and vibration with a frequency not corresponding to the natural frequency of the natural oscillator.

6. The sound and vibration information collecting mechanism according to claim 4, wherein the third layer is formed of a three-dimensional fabric.

7. The sound and vibration information collecting mechanism according to claim 1, wherein the casing for resonance of the second layer is formed of a bead foam.

8. The sound and vibration information collecting mechanism according to claim 1, wherein the natural oscillator of the second layer and the first layer are each formed of a three-dimensional fabric.

9. The sound and vibration information collecting mechanism according to claim 1, wherein a spring constant of the first layer and a spring constant of the natural oscillator of the second layer approximate a spring constant of muscle of a human body.

10. The sound and vibration information collecting mechanism according to claim 1,
wherein a spring constant of the first layer and a spring constant of the natural oscillator of the second layer approximate a spring constant of muscle of a human body, and
wherein a spring constant of the third layer is higher than the spring constants of the first layer and the natural oscillator of the second layer.

11. A computer program causing a computer in a sound and vibration information sensing system which collects and analyzes a biosignal from the trunk, to execute a procedure, the computer receiving the resonance carrier generated in the resonance layer of the sound and vibration information collecting mechanism according to claim 1, via the sensor provided in the sound and vibration information collecting mechanism, and the procedure being
a filtering procedure to filter the received resonance carrier, with a predetermined filtering frequency.

12. The computer program according to claim 11, further causing the computer to execute a state analyzing procedure to analyze a state of the detection target by using a signal waveform of a resonance carrier generated as a result of the filtering of the resonance carrier by the execution of the filtering procedure, wherein, when the detection target by the sound and vibration information collecting mechanism is the living body and the sound and vibration information being the collection target is the sound and vibration information of the cardio-vascular system, in the state analyzing procedure, the computer is caused to execute a procedure to rectify, by detection, a signal waveform of the resonance carrier generated as a result of the filtering by the filtering procedure, and find a low-frequency biosignal with 5 Hz or lower which reflects an autonomic nervous function.

13. A sound and vibration information sensing system which collects and analyzes low-frequency sound and vibration information with a predetermined frequency or lower from a detection target, the system comprising:
the sound and vibration information collecting mechanism according to claim 1; and
an arithmetic means which receives a resonance carrier generated in the resonance layer of the sound and vibration information collecting mechanism, via the sensor provided in the sound and vibration information collecting mechanism and includes a filtering means which filters the received resonance carrier, with a predetermined filtering frequency.

14. The sound and vibration information sensing system according to claim 13, wherein the filtering means is a band pass filter with a predetermined pass band width, and when the detection target by the sound and vibration information collecting mechanism is the living body and the sound and vibration information being the collection target is the sound and vibration information of the cardio-vascular system, a center frequency of the pass band width is set within a 20 to 30 Hz range.

15. The sound and vibration information sensing system according to claim 13, wherein the arithmetic means includes a state analyzing means which analyzes a state of the detection target by using a signal waveform of a resonance carrier generated as a result of the filtering of the resonance carrier by the filtering means, and wherein, when the detection target by the sound and vibration information collecting mechanism is the living body and the sound and vibration information being the collection target is the sound and vibration information of the cardio-vascular system, the state analyzing means includes a means which rectifies, by detection, a signal waveform of the resonance carrier generated as a result of the filtering by the filtering means, and finds a low-frequency biosignal with 5 Hz or lower which reflects an autonomic nervous function.

16. The sound and vibration information sensing system according to claim 13, further comprising an audible sound reproduction part which reproduces, as audible sound, the resonance carrier generated in the resonance layer of the sound and vibration information collecting mechanism or the resonance carrier generated as a result of the filtering by the filtering means.

17. The sound and vibration information sensing system according to claim 16, wherein a predetermined amplitude threshold is set in the resonance carrier, shaping processing to cut a waveform component at or exceeding the threshold is applied to the resonance carrier, a waveform generated as a result of the shaping processing is filtered by a high pass filter, and the audible sound reproduction part uses a waveform generated as a result of the filtering by the high pass filter, for the reproduction.

* * * * *